US006746848B2

(12) United States Patent
Smith

(10) Patent No.: US 6,746,848 B2
(45) Date of Patent: Jun. 8, 2004

(54) PROTEIN QUANTITATION WITH CELL IMAGING DENSITOMETRY

(75) Inventor: Steven Jay Smith, 3855 Orloff Ave. Apt. 7H, Bronx, NY (US) 10463

(73) Assignee: Steven Jay Smith, Brooklyn, NY (US)

( * ) Notice: Subject to any disclaimer, the term of this patent is extended or adjusted under 35 U.S.C. 154(b) by 0 days.

(21) Appl. No.: 09/840,404

(22) Filed: Apr. 24, 2001

(65) Prior Publication Data

US 2003/0059851 A1 Mar. 27, 2003

Related U.S. Application Data

(63) Continuation-in-part of application No. PCT/US99/15743, filed on Jul. 13, 1999.
(60) Provisional application No. 60/105,163, filed on Oct. 21, 1998.

(51) Int. Cl.[7] ............................................. G01N 33/53
(52) U.S. Cl. .................. 435/7.23; 435/7.21; 435/960; 435/967; 436/63; 436/64; 436/518
(58) Field of Search .............................. 435/7.21, 7.23, 435/960, 967; 436/63, 64, 518

(56) References Cited

U.S. PATENT DOCUMENTS

| | | | |
|---|---|---|---|
| 4,968,603 A | | 11/1990 | Slamon et al. |
| 5,008,185 A | | 4/1991 | Bacus |
| 5,143,714 A | | 9/1992 | Cosgrove et al. |
| 5,252,487 A | | 10/1993 | Bacus et al. |
| 5,610,022 A | * | 3/1997 | Battifora ..................... 435/7.23 |
| 5,733,721 A | | 3/1998 | Hemstreet, III et al. |
| 5,741,648 A | | 4/1998 | Hemstreet, III et al. |
| 5,817,032 A | * | 10/1998 | Williamson .................. 600/562 |
| 5,846,749 A | | 12/1998 | Slamon et al. |

OTHER PUBLICATIONS

Jose Riera, et al, 1999, "Use of Cultured Cells as a Control for Quantitative Immunocytochemical Analysis of Estrogen Receptor in Breast Cancer," *Am. J. Clin Pathol,*111: 329–335.
Anthony Rhodes, et al., 2002, "A Formalin –Fixed, Paraffin–Processed Cell Line Standard for Quality Control of Immunohistochemical Assay of HER–2/neu Expression in Breast Cancer," *Am. J. Clin Pathol,* 117: 81–89.
Jose M. Esteban, et al., 1993, "Improvement of the Quantification of Estrogen and Progesterone Receptors in Paraffin–Embedded Tumors by Image Analysis," *Am. J. Clin Pathol*99: 32–38.
Jose M. Esterban, et al., 1994, "Biologic Significance of Quantitative Estrogen Receptor Immunohistochemical Assay by Image Analysis in Breast Cancer," *Am J Clin Pathol*99:102: 158–162.
Karen Z. Walker, et al, 1989, "Detection of Malignant Cells in Voided Urine From Patients with Bladder Cancer, A Novel, Monoclonal Assay," *J Urol.* 142:1578–1583.

P. Fritz, et al, 1989, "Quantitative Immunohistochemistry: Standardization and Possible Application in Research and Surgical Pathology," *Acta Histochemica, Suppl–Band,* XXXVII, S:213–219.
M.F. Press, et al., 1993, "Her–2/neu Expression in Node–Negative Breast Cancer Direct Tissue Quantitation by Computerized Image Analysis and Association of Overexpression with Increased Risk of Recurrent Disease," *Cancer Research,* 53:4960–4970.
Michael F. Press, et al., 1994, Sensitivity of Her–2/neu Antibodies in Archival Tissue Samples: Potential Source of Error in Immunohistochemical Studies of Oncogene Expression,: *Cancer Research,* 54:2771–2777.
J.M. Esteban, et al., 1991, "Quantification of Estrogen Receptors on Paraffin–Embedded Tumors by Image Analysis," *Modern Pathology,* 4:53–57.
C.J. Fisher, et al., 1994, "Problems with p.53 Immunohistochemical Staining: The Effect of Fixation and Variation in the Methods of Evaluation," *Br. J. Cancer,* 69:26–31.
O. Baas, et al, 1994, "An Evaluation of Six Antibodies for Immunohistochemistry of Mutant p.53 Gene Product in Archival Colorectal Neoplasms," *Journal of Pathology,* 172:5–12.
Clive Roy Taylor, 1986, "Immunomicroscopy: A Diagnostic Tool for the Surgical Pathologist," *Major Problems in Pathology, vol. 19*(W.B. Saunders Company), pp. 43–53 and pp.248–251.
Michael D. Linden, 1994, "Evaluation of Anti–P53 Antibody Staining. Quality Control and Technical Considerations," *Applied Immunohistochemistry,* 2:218–224.
R. Ranney Mize, et al., 1988, "Quantitative Immunocytochemistry Using an Image Analyzer. I. Hardware Evaluation, Image Processing, and Data Analysis," *Journal of Neuroscience Methods,* 26:1–24.

(List continued on next page.)

Primary Examiner—Christopher R. Tate
Assistant Examiner—Roy Teller
(74) *Attorney, Agent, or Firm*—Morgan & Finnegan, LLP

(57) ABSTRACT

A method for quantitating cellular proteins in tissue, by means of a cell imaging densitometer in conjunction with immunohistological staining and a reference standard, is provided. Unlike prior art methods, which provide ordinal measures of relative amounts of protein among different cells, the method enables the quantitation of antigenic proteins in terms of absolute mass of protein/tumor or protein/patient, molecules of protein per cell, and volume or fraction of a tissue sample expressing the protein of interest. The method is useful for research purposes in the study of protein expression, and is shown to improve the accuracy of clinical histopathological analysis of tumor tissue sections for diagnosis and prognosis. The method is expected to be useful for prescribing in situ treatment dosages. The demonstrated resulting improvement in the correlation between tissue levels and blood levels of tumor-associated proteins should facilitate minimally-invasive monitoring of cancer progression and therapeutic response.

21 Claims, 17 Drawing Sheets

OTHER PUBLICATIONS

L. Burt Nabors, et al., 1988, "Quantitative Immunocytochemistry Using an Image Analyzer. II. Concentration Standards for Transmitter Immunocytochemistry," *Journal of Neuroscience Methods*, 26:25–34.

Frode Varidal, et al., 1986, "Immunofluorescence Staining of Agarose–Embedded Cell, a New Technique Developed for Immunological Characterization of Markers on a Small Number of Cells," *Journal of Immunological Methods*, 92:125–129.

Per Brandizaeg, 1982, "Techniques in Immunocytochemistry," vol. 1 (Gillian R. Bullock, Peter Petrusz, Eds.), (Academic Press, Inc.), pp. 1–75.

Massimo Derenzini and Davide Trere, 1991, Standardization of Interphase Ag–NOR Measurement by Means of an Automated Image Analysis System Using Lymphocytes as an Internal Control, *Journal Pathology*, 165:337–342.

Ranefall, P., Bengisson, E., 1998, "Automatic Quantification of Immunohistochemically Stained Cell Nuclei Using Unsupervised Image Analysis." *Anal. Cell Pathol.* 16:29–43.

Petter Ranefall, et al, 1998, "Automatic Quantification of Immunohistochemically Stained Cell Nuclei Based on Standard Reference Cells," *Anal. Cell. Pathol.* 17:111–123.

Kenneth Wester, et al., 2000, "Cultured Human Fibroblasts in Agarose Gel as a Multi–Functional Control for Immunohistochemistry Standardization of K167 (MIBI) Assessment in Routinely Processed Urinary Bladder Carcinoma Tissue," *J Pathol*, 190:503–511.

"*Quantitative Oncogene Product Users Manual*," 1990 (Cell Analysis Systems, Inc., Catalog No. 201725) pp.1–51.

* cited by examiner

| $R^2$ | F-test | Statistical Significance | α | $\beta_x$ |
|---|---|---|---|---|
| 0.820 | 4.55 | 0.279 | 10.8345 | 0.8666 |

PROTEIN QUANTITATION WITH CELL IMAGING DENSITOMETRY

RELATED APPLICATIONS

This is a continuation-in-part of international application PCT/US99/15743, filed Jul. 13, 1999, which claims priority from U.S. provisional application No. 60/105,163, filed Oct. 21, 1998.

FIELD OF THE INVENTION

The invention relates to the fields of microscopy, computerized cell imaging, immunohistochemistry, histopathology, oncology, protein quantitation, and diagnosis and prognosis of cancer and other diseases.

BACKGROUND OF THE INVENTION

1. Immunohistology

The presently universally-accepted method for the diagnosis of all types of solid cancer is the histologic determination of abnormal cellular morphology in surgically biopsied or resected tissue. Once removed, the tissue is preserved in a fixative, embedded in paraffin wax, cut into 5 μm-thick sections, and stained with two dyes: hematoxylin for the nucleus and eosin for the cytoplasm ("H&E staining").[1, 2] This approach is simple, fast, reliable, and inexpensive.

Histopathology allows the diagnosis of a variety of tissue and cell types. By providing an estimation of tumor "Grade" (cellular differentiation/tissue architecture) and "Stage" (depth of organ penetration) it also makes prognosis possible.[3, 4] In the Surgical Pathology Departments of larger hospitals histologic H&E staining is generally automated, tissue-processing technique is standardized, and histologic interpretation is well established.

Aside from crude measurements of the tumor diameter, pathologists do not attempt to quantify the area or volume of dysplastic tissue, nor do they perform absolute quantification of the cancer-related proteins present in such specimens. When antibody staining is attempted—commonly called immunohistochemistry (IHC)—the intensity and area of its visible or fluorescent color is ranked in an ordinal fashion. This ordinal ranking by the pathologist is accomplished by to the subjective impression of both the extent (area) and the darkness of the stain, compared to adjacent, morphologically normal tissue. The number of ranked categories and the cutoff points for each is arbitrary and inconsistent among observers. Also, for some organs and cancer proteins, there has been observed a "field-effect" in which abnormal proteins are expressed in adjacent, supposedly negatively-stained, morphologically normal tissue.[5] Furthermore, since there is no matching of cells between the H&E histology slide and the immunostained slide, it is difficult to segregate the immuno-scoring for different histologic classes, e.g., cancer and pre-cancer, within the same section and it is impossible to accurately correlate total immunostaining with histologic area for each tissue class.

The currently available optical techniques of microscope-based cell imaging provide a partial solution to the problem of performing these cellular measurements. This approach uses conventional light microscopy combined with monochromatic light filters and computer software programs. The wavelengths of the light filters are matched to the colors of the antibody stain and the cell counterstain. The filters allow the microscopist to identify, classify and then measure differences in the optical density of specific colors of light transmitted through immunostained portions of tissue sections. See U.S. Pat. Nos. 5,235,522 and 5,252,487, both of which are incorporated herein by reference, for applications of these methods to tumor protein measurement.

More advanced cell imaging systems (image cytometers) permit automated recognition of features, and combine this with automated calculation of feature areas, automated calibration, and automatic calculation of average and integrated (ΣOD) optical density. (See, e.g., U.S. Pat. Nos. 5,548,661, 5,787,189, both of which are incorporated herein by reference, and references therein.) Merely scoring patient tissue immunostaining by ordinal rank, however, even by incorporating the more objective and uniform optical estimation techniques provided by Cell Imaging Densitometry (CID), provides limited information for patient and tissue evaluation. By translating such scoring into common biological units of measurement, oncologists and pathologists can refer to the patient's particular "profile" of tumor suppressor and oncogene protein levels. Thus, the clinician will be able to numerically predict a patient's "relative risk" of relapse or death, probability of chromosomal instability, metastases, response to therapy, or even probable survival duration. The suggested method should also make it possible to sum up a patient's total "body burden" of such proteins, where there are multiple lesions. A fraction of this tissue burden escapes the porous membrane of the cancer cells into the blood stream perfusing the tumor(s), achieving a steady-state concentration over time. Immunoassays e.g., ELISA, can accurately and sensitively measure these volumetric concentrations. Knowing the typical quantitative correlation between blood levels and tissue expression will allow us to more effectively (and less invasively) indirectly monitor residual/recurrent disease.

One reported attempt to improve the accuracy of the measurement of cancer protein in tissue used Western Blotting in combination with CID to create immunohistochemical rankings when measuring HER-2/c-erbβ-2 oncogene protein expression in breast cancer patients.[6] In this attempt, cultured human breast cancer cells were genetically-engineered in order to express different levels of the oncogene protein. HER-2 protein levels (pg/cell) in the cell lysates of these reference cells were estimated with dilutions of a fragment of recombinant purified HER-2, using the Western blot assay and laser densitometry. Cultured cell pellets were snap-frozen in "OCT" (polyethylene glycol-polyvinyl alchohol-trimethylbenzylammonium chloride) embedding media, cut into 4 μm sections with a cryostat, and then attached to microscope slides, presumably by air drying. Breast cancer tissue was fixed in 95% ethanol, followed by buffered formalin. Alternatively, tissue from the same tumors was either frozen in OCT and cryosectioned, or paraffin-embedded and sectioned with a microtome. A CID/Western blot "standard curve" on the cultured cells was created with a single immunostained CID standard, which was assumed (without testing or reference) to be 1 pg/cell. This "curve" from the frozen reference cells was then applied to the immunostained breast tissue by using a single "correction factor" (~40%) in order to boost the actual optical density scores for the paraffin tissue sections. In the eventual correlation of tumor recurrence with HER-2 overexpression these "quantitative" immunostaining scores were, once again, reduced to ordinal ranks, "Low", "Medium", and "High", which reflected increasing degrees of amplification of the gene's DNA. The authors were able to predict relative differences among the women in their risk of tumor recurrence.

However, fixation conditions of the reference cells and the tissue were different, there were no immunostained paraffin sections for the reference cells, and the frozen tissue stained more intensely than the paraffinized tissue (disproportionately so, depending upon the level of HER-2 protein overexpression). This approach provides no method to summarize the total HER-2 tumor burden per patient or tumor. The reliance upon Western blot for quantitation of the oncoprotein cell is a disadvantage, due to the complexity and slowness of the procedure, plus its modest quantitative accuracy, precision and reproducibility.[7–9] Another approach employs simultaneous measurement of nuclear DNA by cell imaging to provide an internal calibration reference (U.S. Pat. No. 5,252,487). This method is subject to variations in the intensity of the DNA staining and derives its calibration "curves" for staining intensity×pg DNA/cell from a single DNA value.

Another attempted to solve the problem was the Quicgel™ method, described in U.S. Pat. No. 5,610,022, which used immobilized cultured cells as "internal controls" in order to estimate the "pre-processing immunoreactivity level" of individual paraffin tissue sections.[124] The stated goal was to compensate for unpredictable and/or excessive loss of antigenicity due to fixation, which often alters the chemical structure of antigens. The internal controls were intended to provide a correction factor, allowing an estimation of the IHC staining intensity that would have been obtained with fresh, unfixed tissue. These internal controls ("pseudo-tissue") were treated as though they were tissue, and were subjected to the same processing conditions experienced by a clinical tissue sample sharing the same paraffin block.

In this approach, the "pseudo-tissue" control cells were fixed twice. The first fixation, prior to immobilization of the cells in a matrix, was in paraformaldehyde for less than ten minutes at room temperature. This level of fixation has previously been shown to be sufficient to maintain the structure of the cultured cells while minimizing antigen diffusion and loss of immunoreactivity.[125, 126] The fixed cells were then encased in a thick, 3 mm slice of agar gel, and this "pseudo-tissue" underwent a second fixation in 10% neutral buffered formalin, duplicating precisely the conditions under which the tissue sample was fixed. The patent describes a test of the Quicgel™ method, wherein the pseudo-tissue and tissue samples were exposed to formalin for four fixation times ranging from 4 to 72 hours, in order to determine the rate at which immunoreactivity was lost over time for both the pseudo-tissue controls and the adjacent tissue samples.

Typically, formalin fixation of patient tissue lasts 6–12 hours; the time must be adjusted for the size of the tissue specimen and the density of its tissue type (e.g., lung tissue is penetrated very quickly, while breast tissue is penetrated much more slowly).[127] The Quicgel™ method attempted to correct for the resulting variations in immunostaining level by using a cell imaging densitometry program to measure overall staining area, or intensity in pixels, but did so without a standard curve. Rather, the method assumed the existence of an inverse proportionality between fixation duration and cell staining that was linear back to zero fixation time, and also assumed an equal rate of loss of immunostaining for the "pseudotissue" and the specimen tissue, regardless of the identity or size of the specimen. As discussed below, both assumptions are incorrect.

For these reasons, there has never been a demonstration of the Quicgel™ method for correlation of protein levels with patient survival or matched blood levels, no incorporation of histologic tissue class, and no calculation of tumor burden. Others have subsequently used reference cells to standardize microscope settings and automate cell imaging scoring via gray scale tables to maximize optical density contrasts. These workers also conducted extensive fixation of the pseudotissue.[128] More recently, this same group has extended the Quicgel™ approach for fixation artifact correction, testing the method with both internal controls (same paraffin block as the tissue sample) and external controls (separate paraffin block, but stained simultaneously) for the effects of fixation duration and tissue sample storage conditions. They also found fixation artifacts in cells and tissue to be subject to discontinuities.[129]

The approaches just described have deficiencies which make it impossible to standardize IHC scoring and to translate optical density pixels into absolute quantities of protein. FIGS. 19 and 20 present the data given in the description and figures of U.S. Pat. No. 5,610,022. It is apparent that the degree of loss of immunoreactivity in the pseudotissue and in the specimen tissue at different fixation times is not the same, regardless which cell imaging measurement is used. Because the loss of staining is not proportional, the pseudotissue controls cannot be used to estimate pre-processing immunoreactivity level in the breast tissue samples. This is true even within the observed range of fixation times; reliable extrapolation back to time zero is therefore not possible. This is indicated by the lack of statistical significance of the implied linear regression equations, suggested by the model used in U.S. Pat. No. 5,610,022. This is not surprising, given the relative rates of fixative penetration in the trypsinized reference cells versus the dense, stroma- and lymphocyte-laden, high-fat breast tissue samples.

To create a valid standard curve for protein quantitation, both calibration cells and specimen tissue should be subjected to the same fixative and IHC reagents, the treatments of each must be optimized with respect to such things as fixation duration and temperature, antibody concentration, and substrate incubation time. The goal is identical staining of the calibration cells and the tissue samples, not identical treatment. If the former condition can be met, the amount of target protein can be read off the cell imaging calibration cell staining curve for each IHC batch. Whether the staining of the calibration cells and the tissue is, in fact, identical, will be revealed from the similarity of their respective cell imaging:

1. signal/noise ratios;
2. frequency distributions;
3. dynamic range of protein expression; and
4. definitions of positive staining.

Fixation and staining conditions may vary with the tissue type, fixative, antibody, and IHC materials and methods used, but if identical staining between standards and specimens can be achieved, inter-laboratory results for any protein will be commensurate. The present invention, by eliminating fixation of the pseudotissue (a step heretofore assumed to be essential to the use of pseudotissue controls), provides a quantitation method that satisfies all the above criteria, and which is demonstrably superior to subjective IHC scoring in its ability to generate histologic diagnoses and target protein concentrations in blood, and to correlate them with cancer patient survival.

As recently as May 17, 1996, the *American Society of Clinical Oncology* summarized the current state-of-the-art in the use of tumor marker tests in prevention, screening treatment and surveillance of breast and colorectal cancers. [10] It assessed a variety of tumor markers, such as p53, CEA, and DNA flow cytometry [HER-2 was not considered]. The consensus report concluded that such markers continued to have limited prognostic or predictive value. When DNA mutations are assessed, it is often not clear which mutations have an impact upon gene function. With respect to IHC the problem is the inability to generalize among the results from different clinical trials; this is due to the variety of antibodies and lab methods used as well as the absence of a common objective criterion for "abnormal" staining.

There remains, therefore, a need to standardize the current method of scoring immunohistologic staining of paraffin-embedded tissue sections. This would to allow valid comparisons of results among different laboratories or among different staining batches within the same lab for any disease-related protein for which there are adequate antibodies and cultured cell lines. Such standardization would also create the conditions for direct quantitation of disease-causing antigens in patient tissue and blood. Such measurement offers the potential for determining in-situ treatment dosages as well as estimated months of patient survival. The present invention provides such a standardization method.

Although over-expression of aberrant proteins is usually multi-focal, it is also clonal in nature: abnormal proliferating cells are contiguous in their staining—due to cell division from a single progenitor cell—and share the same proliferation behavior and a common profile of genetic defects. In the case of p53 this phenomenon distinguishes clonal expression of the mutated protein from a transitory over-expression of wild-type protein in an occasional cell in which the tumor suppressor response has been elicited. The latter mosaic-staining pattern will generally affect a small fraction of the cells present, and can generate false positive data if the tissue sample is heavily labeled. The methods of the present invention make it possible to avoid such false positives, by using appropriate tissue controls and/or cell controls rather than simply a "negative control" antibody.

In the fields of cancer research, diagnosis, and therapy, the morphologic evidence of cancer (or pre-cancer) together with the identification and measurement of specific cancer proteins in the same cells is a powerful combination. In principle, this combination of morphology and protein measurement permits one to know whether it is only the abnormal cells which are expressing specific proteins at particular moments and in known amounts in the natural history of the tumor being studied. Two things have been missing, however, from the set of tools needed to fully exploit this combination: (1) an accurate and reliable way to link individual foci of histologically and immunologically abnormal target cells (glandular crypt cells in the case of colorectal cancer); and (2) an accurate, objective and consistent quantitative method to score both the intensity/cell and the total immunopositive area (nuclear area in the case of p53). The present invention provides these missing elements (FIG. 1).

2. Role of p53 Protein in Cancer

The many roles of p53 in controlling the rate of cell proliferation and DNA repair at the G1/S phase of the cell cycle is widely appreciated. It acts to curb the effect of prior mutations that have occurred in pre-cancerous growths, such as adenomas. Less frequently acknowledged is p53's role in maintaining the body's "back-up" system of DNA-maintenance (diploidy) at both G1/S and the G2/M stages of the cycle [11, 12, 13].

Besides its importance in the rate of DNA replication, DNA repair/chromosome stability, and cell cycle arrest, p53 is one of the primary cellular reactants involved in the induction of programmed cell death: apoptosis. Normal p53 affects cell growth through its interaction, direct and indirect, with the cyclin-dependent kinase (cdk) regulatory pathways. It promotes apoptosis by stimulation of endo-nucleolytic enzyme attack upon chromosomes containing badly damaged DNA.[14] This occurs at the G1/S stage of the cell cycle. While p53's cell growth arrest tumor suppressor function is temporary and reversible, the result of its apoptotic function is permanent. The sacrifice of the damaged/cancerous cells protects the whole organism against the cells' undesirable continued replication and propagation of their heritable abnormalities.

3. Previous Methods for Quantitation of p53 Protein

There has been a great deal of effort expended to make detection and/or measurement of p53 levels simple and reliable. Numerous antibody-based histological reagents are now commercially available for immunohistochemical detection and estimation of p53 protein in tissue samples. A great deal of effort has also gone into attempting to correlate these measurements with tumor status and patient prognoses. The results of these efforts, to date, have been mixed.

At best, immunohistochemistry measurements on human tumor tissue are done in terms of arbitrary ordinal ranks or "percentage of intensely-staining cells" or the like. One review of the biochemical, immunological, and functional aspects of p53 reports that among mammalian cell cultures, transformed cell lines contain 10–100 times greater levels of p53 than non-transformed cells.[15] Studies indicate that this accumulation is due largely to protein accumulation, rather than increased gene dosage or RNA transcription levels. Using radio-labeling and a monoclonal antibody-bound affinity column, the p53 concentration in the lysates from 11 of 15 human tumor-derived or transformed cell lines was >5 times that of normal human cell lines.

Virally transformed cell lines exhibit extreme over-expression. For example, in SV40-transformed human fibroblasts p53 expression exceeded that of normal human cells by a factor of 2,250. In absolute terms, measured concentrations for these cell lines ranged from "undetectable" to 450 ng/mg. Normal cell cultures (human fibroblasts and human foreskin epithelial cells) had $\leq 0.2$ ng p53/mg cellular protein.[16] Another study used two different types of fluorescent sandwich ELISA: a mutant-p53-specific (pAb 240), and a pantropic p53 monoclonal capture antibody (pAb 421) to measure p53 protein in 23 tumor cell lines, breast tissue extracts and 800 breast cancer patients sera. The mutant p53 for the extracts was all in the 0–2 ng p53/mg total protein range; and the sera were all negative. In two colorectal cancer cell lines having p53 mutations combined with deletion of the other allele and one colorectal cancer cell line having neither, the results [17] were as shown in Table 1 (ng p53/mg total cell lysate protein):

TABLE 1 p53 Concentrations in Colorectal Cancer Cell Lines

| Cell Line | PAb 240 (ng/mg) | PAb421 (ng/mg) | p53 |
|---|---|---|---|
| Colo 320 (HSR+) | 62.0 | 39.0 | $p53^{mut}$ |
| Colo 320 (DM+) | 100.0 | 42.0 | $p53^{mut}$ |
| C1 | 2.3 | 3.9 | $p53^{wt}$ |

A similar study measured p53 levels in breast cancer tissue in immunostained paraffin sections and the cytosol extracts from the same tumors, It used the pantropic rabbit polyclonal antibody (CM-1) for the IHC and a sandwich-type ELISA incorporating the pantropic DO-1 monoclonal as the p53 solid-phase capture antibody and CM-1 as the detection antibody. There was a moderate correlation between the IHC and ELISA scores (Pearson $R^2=0.35$, $p<0.00001$). However, IHC scoring [(ordinal rank for "intensity")×(percentage p53$^+$ cells)] is subjective and, therefore, impossible to compare with results from other studies, and it is difficult to use this information for prognosis when evaluating a given tissue sample. The IHC done upon the cancer cells' nuclei was more sensitive than the ELISA, since it can distinguish not only cellular from stromal material, but also cancerous from non-cancerous tumor cells and p53$^+$ from p53$^-$ cancerous (or adenomatous) cells. The ELISA scores for the p53$^+$ tissue sections were in ng p53/mg cytosol protein; the average value was 44 ng/mg protein with individual amounts ranging widely from 2–230 ng/mg.[18]

Another such study examined p53 levels in the soluble extracts of colon and gastric cancer tumors. The two-epitope, sandwich ELISA was employed using the DO-1 pantropic capture antibody for inactivated p53. The IHC was done on frozen fixed tissue with a panel of three different antibodies: one pantropic monoclonal (DO-1), one pantropic polyclonal (CM-1), and one mutant-specific (pAb 240). Again, the p53 range in the cytosol was similar: 0.1–2.3 ng p53/mg protein. Western blots done on the tumor tissue gave perfect+vs.–concordance between the DO-1 and pAb 240 antibodies in the Westerns; there was also 100% concordance by tumor among the assays (Westerns, pantropic ELISA, and IHC). In the same type of scoring as was done on the breast cancer tumors, the correlation was significant (Kendall's r=0.75, p<0.002).[19]

Finally, the manufacturer of the mutant sandwich ELISA kit used herein for the calibration cell lines also reports detecting p53$^{mut}$ concentrations among 9 different mammalian cell lysates in the ng/mg range. Specifically, for the p53$^{mut}$ A431 cell line, also used herein, the reported result was 7 ng p53$^{mut}$/mg.[20] One published study, however, using the same mutant ELISA, reported anomalous findings: 781 µg p53$^{mut}$/mg in the same A431 vulvar squamous carcinoma cell line, and very strong banding with a pantropic MAb Western blot, despite weak bands appearing in a Western blot using the mutant-specific PAb 240 antibody. [21] Clearly, there remain some difficulties with lab-to-lab variations in the execution of these assays.

In addition to measuring p53 quantities in mass and volume per tumor or cell lysate, it is possible to do so in terms of number of p53 molecules per cell, something that has been done very rarely. Measurement of the molecular concentrations of cancer proteins—independently of their respective mass—reveals the true ratios in which they combine in cellular reactions, providing insights into the stoichiometric chemistry of the cancer cell. It has been estimated that in normal cells the expression level is about 5,000 molecules p53/cell.[22] There is one other study of the number of p53 molecules/cell, which used flow cytometry to quantify the amount of p53 protein. These authors examined 10 different strains of bovine papilloma virus-transformed mouse fibroblasts and also one strain of non-transformed mouse fibroblast cells.[23] They found 2,947 molecules p53/cell in the non-transformed cells versus an average of 9,088 molecules p53/cell in the transformed fibroblasts. They also contrasted the levels of 10 cell lines within the transformed category (5 tumorigenic versus 5 non-tumorigenic), finding an average of 11,432 and 6,743, respectively (Mann-Whitney, p=0.0034).

There is a great deal more known about the levels of normal and inactivated p53 expression in human sera and plasma through the use of these same ELISA kits. There are examples of a statistically significant association between serum or plasma p53 ELISA and cancer/normal status. [24–26] There are instances of statistically significant correlations between the concentration of p53 in the blood and a patients diagnostic status for colorectal adenocarcinomas, adenomas, and normal controls, [27, 28] and multiple studies in which those levels decreased following surgical removal of the tumor (e.g., colon and breast, respectively). [29, 30]

There are examples of significant correlations between p53$^+$ and p53$^-$ status in tissue IHC, and "elevated" versus "undetectable" serum/plasma p53 in ELISA, or even continuous variable regression between the levels of p53 in tissue IHC and both mutant and pantropic ELISA analysis of serum.[31, 26] Examination of pancreatic adenocarcinoma paraffin sections stained with the DO-7 pantropic p53 monoclonal, combined with mutant p53 ELISA analysis of these same patients sera, has shown one of the strongest associations yet between blood and tissue p53 expression [32]. Of those people whose serum contained detectable mutant p53, 80% also had over-expressed p53 in their tumor tissue and had significantly greater blood concentrations Of p53$^{mut}$, compared to the serum of those patients whose tissue was immuno-negative. Serum p53 in these cases was significantly greater than in healthy controls or patients with benign pancreatic conditions. Even though serum p53 concentrations did not correlate with those of more conventional markers such as CEA or CA19-9, it was significantly greater in those patients with existing metastases than in those without. Tissue staining appeared to be far more sensitive for p53 inactivation, than was the serum ELISA: 22% of the cancer patients were p53$^+$ in the serum ELISA, while 46% of these patients were p53$^+$ in the IHC. One study of banked lung cancer sera specimens, not only found significant agreement between DNA mutations, elevated p53$^+$ IHC (DO-1), and p53$^{mut}$ serum ELISA (PAb 240) scores, but was able to predict future development of tumors based upon the detection of p53$^{mut}$ in the sera (positive predictive value= 0.67, negative predictive value=0.83) [33]. There is some consistency among the cited studies regarding the ranges and averages of the concentration of inactivated p53 in human plasma or sera: typically, in the pg p53/mL range.

SUMMARY OF THE INVENTION

The invention provides a method for preparing cultured cells for immunostaining, which comprises the step of immobilizing said cells in a hydrophilic matrix that is non-liquid at room temperature (18–25° C.). The matrix may be, for example, an aqueous gel of a polymer chosen from the group consisting of proteins, oligosaccharides, and poly (acrylamide), preferably gelatin, agarose, pectin, or poly (acrylamide). The matrix is more preferably an aqueous gel of "low temperature" agarose. A typical low-melting point agarose, once dissolved in boiling phosphate buffered saline, remains in solution until cooled below 25° C., and once solidified, only remelts above 65° C. Such a matrix allows for convenient handling and avoids destroying any cell culture protein of interest from exposure to temperatures above normal physiologic range (37–40° C.). Prior to immobilization, the cells may optionally be fixed by contacting them with a tissue fixative. Suitable tissue fixatives include formalin and Bouin's.

The invention also provides a method of preparing calibration slides for a cell imaging densitometer. The method comprises the steps of immobilizing cultured cells in a hydrophilic matrix as described above, fixing the hardened matrix in a paraffin block in the usual manner, and sectioning the paraffin block into thin slices. The cultured cells are preferably preserved with formalin fixative prior to immobilization in the hydrophilic matrix. This method may be adapted to cryostat-sectioned frozen cultured cells and tissue, preserved with suitable fixatives e.g., acetone or ethanol, and embedded in a suitable tissue-freezing medium in place of paraffin. It may also be adapted to immunocytology specimens prepared as "smears" from exfoliated patient cells or from clinical cell suspensions centrifuged at low speed, thus attached in either manner to microscope slides.

It was previously stated in PCT/US99/15743 that the embedded calibration cells must be fixed and treated in an identical fashion as the patients' exfoliated cells or surgically-excised tissue. However, identical fixation was not in fact carried out in the examples described, and the superior results obtained with the present invention are due in part to the absence of such post-embedding fixation.

The invention also provides for visualizing a protein of interest on the calibration slide, wherein the slide is contacted with a first antibody. The first antibody may optionally be conjugated with a chromogenic or fluorogenic reagent. Alternatively, the slide may then be contacted with a second antibody, having binding affinity for the first antibody. The second antibody is also optionally conjugated to a chromogenic or fluorogenic reagent.

As an alternative to conjugation with chromogenic or fluorogenic reagents, the above antibodies may be conjugated to one of a pair of auxiliary affinity reagents. This permits binding, in a subsequent operation, of chromogenic or fluorogenic reagents which are conjugated to the other member of the pair. Suitable pairs of auxiliary affinity reagents include biotin-avidin and biotin-streptavidin. In this embodiment, the antibodies are preferably conjugated to avidin or streptavidin, which permits multimeric binding of biotin-conjugated chromogenic or fluorogenic reagents with a corresponding amplification in the signal. In an alternative embodiment, both the antibody and the chromogenic or fluorogenic reagent are conjugated to biotin, and they are contacted with one another in the presence of avidin or streptavidin.

A chromogenic reagent is a reagent that is itself highly colored, or that generates a colored dye or pigment upon exposure to specific chemicals or conditions. Examples of the latter include enzymes such as peroxidase.

A fluorogenic reagent is a reagent that generates light, upon exposure to specific chemicals or conditions, or that fluoresces upon exposure to light. Examples include enzymes which upon exposure to appropriate substrates generate luminescent or fluorescent products, such as peroxidase and luciferase, and fluorescent dyes such as fluorescein, brilliant red, rhodamine, and the like. Numerous such reagents and dyes are well-known in the art, and are anticipated to be useful in practicing this invention.

The particular embodiment described herein employs biotin and avidin as the auxiliary affinity reagents, peroxidase as the chromogenic reagent, hydrogen peroxide and 3,3'diaminobenzidine (DAB) as substrates [see U.S. Pat. No. 4,684,609], and image densitometry as the measurement method. It will be readily understood by those skilled in the art that fluorometric (e.g. photon-counting) methods with a fluorescence microscope (e.g. a CCD camera-equipped microscope) will be equally operative if the conjugated reagent generates rather than absorbs light. The chromogenic or fluorogenic reagent (or reaction product) will preferably absorb or emit light within a narrow enough wavelength range that a second chromogenic or fluorogenic reagent or product, emitting or absorbing in another wavelength range, will be usable without interference. Many such reagents are known in the art, and most are anticipated to be useful in practicing the present invention.

The invention further provides a method for measuring the amount of a protein of interest in a cell or a cell organelle. The method comprises the steps of affixing the cell to a microscope slide, optionally in the form of a paraffin block section, staining the cell with an immunohistochemical stain such as the conjugated antibodies described above, and measuring with a cell imaging densitometer (or fluorimeter) the area and density of the stain within the cell or cell organelle. The amount of stain within the cell or cell organelle is proportional to the summed optical density, which is most conveniently calculated with the software associated with the instrument. The summed optical density is then converted into the amount of protein of interest by reference to a calibration slide prepared as described above and stained concurrently with the same immunohistochemical stain. The amount of protein of interest actually in the cells on the calibration slide is measured by an independent assay of said protein in a sample of the calibration cells. The independent assay method may be any assay that is quantitative and specific for the protein of interest, such as an ELISA or Western blotting assay, preferably an ELISA. Provided that the molecular weight of the protein of interest and its molecular concentration in the calibration cells has been determined, measurement of the average volume of the diseased cells expressing the protein in the body allows for the estimation of the number of such molecules per cell. The phrase "amount of protein of interest" is intended to encompass amounts measured in mass units, moles, or numbers of molecules; this amount may be expressed relative to any convenient measure, such as per cell, per cell organelle, per patient, per tumor, or per unit volume of tissue or body fluid.

The protein of interest may be a tumor-associated protein, and the cell may be a tumor cell, as in the examples below. Other proteins of interest, which may be associated with disease states, which may be expressed in recombinant, gene-activated, or endogenous cells for a therapeutic purpose, or which may be of research interest, may be quantitated as well, provided only that appropriate cell lines and specific antibodies are available to the practitioner, or can be prepared.

The invention also provides a method of calculating a patient's body burden of a protein of interest. This method comprises the steps of measuring the amount of the protein of interest in one or more cells taken from one or more of the patient's tumors, by the method described above, and converting the amount of protein so determined into the amount of protein in the tumor itself. This is readily done by estimation of tissue or tumor volume from measured tissue or tumor dimensions. By adding together the amount of protein in each tissue or tumor, the total amount of protein in all the patient's tissue or tumors is obtained, and this is the patient's body burden of the protein.

The invention also provides a simple and inexpensive method for measuring the area of a feature of interest that is visible in the field of view of a microscope equipped with a video camera, where software providing this function is either not available or unsuitable. A field finder (a microscopic printed grid) is placed over the microscope slide, which, with appropriate magnification, results in the appearance of a grid with easily visible squares on the monitor. An outline of the stained region of interest, which is imaged on the monitor, is traced on a material having a printed grid on its surface, such as a sheet of graph paper. The outline is then cut out and the cutout piece of material weighed. With knowledge of the mass of the material per unit area, the mass of the cutout may optionally be converted to area of material. By outlining, cutting, and weighing a rectilinear piece of the same material corresponding to a known number of grid squares on the monitor, the area (or mass) of the cutout may be converted into actual area on the slide, as measured by the field finder. The "conversion factor" is the mass of the material per unit area of the field finder as imaged on the monitor. Any graph paper or similar material may be used, provided that the density of the material is sufficiently uniform to provide a reliable correlation between mass and surface area. The microscope objective and dimensions of the matrix visualized on the monitor are usually specified by the user using a menu from the CID software provided. FIG. 2 is an overview of sequence of the immunohistologic measurements and how one measurement is derived from another. The (mm$^2$) area measurement procedure co-listed in step one in FIG. 2 is described in more detail below [Cell Imaging Densitometry Measurements, including Table 7].

The invention also provides for a method of predicting the clinical outcome of cancer for a patient, which involves providing a statistically derived continuous function that relates the amount of a tumor-associated protein within the patient's tumors, as measured by the method of this invention, to clinical outcome in a population of patients with the same cancer. By measuring the amount of the tumor-associated protein in the patient's tumor cells by the same method, and by referring to the continuous function provided, clinical outcome may be predicted with improved reliability over prior art methods.

For cancer prognosis, especially for adenocarcinoma, the tumor-associated protein is preferably a mutant p53 (p53$^{mut}$). In those cancers which are partly due to a loss of p53 function, the expected increase in multi-drug resistance and reduction in the effectiveness of anti-angiogenesis drugs would make such patients poor candidates for these treatment options. Alternatively, the replacement of the presumably defective p53 gene with a functional gene coding for p53, by means of genetic therapy, is a promising approach. [34–36] Administration of genetic therapy with p53-encoding DNA, which is based upon restoration of p53 expression in tumor cells, presupposes that the prospective patient's tumors are expressing p53$^{mut}$. It would, therefore, be useful to know beforehand the p53 status of the patient, both for selecting a patient population for clinical trials and for guiding administration of genetic therapy to patients among the public. Other p53-specific therapies are under investigation, including antisense DNA therapies and anti-p53 antibodies, which are directed toward reducing the tumorigenic effects of p53$^{mut}$. The present invention provides a method of selecting patients for p53-specific therapies, and p53 genetic therapy with p53-encoding DNA, based upon a quantitative measure of p53$^{mut}$ concentrations in the patient's tumor cells and/or the patient's p53$^{mut}$ body burden. The present invention provides, as well, a method of monitoring the effectiveness and progress of such therapies, again by quantitative measure of p53$^{mut}$ concentrations in the patient's tumor cells, total p53$^{mut}$ body burden per patient, or its derivative surrogate measure: the concentration of p53$^{mut}$ in his or her blood.

The present invention employs cultured cells, preferably inexpensive standard human tissue cell lines standardized according to quality controls performed by the American Type Culture Collection. The calibration cells express a protein of interest at a reproducible level that can be easily and accurately measured. In the first instance, these cells can be used, simply, as "positive" and "negative" immunostaining "batch controls". In this aspect the changing intensity of their staining improves CID by helping the operator decide which cells within the tissue sample to score. In this preliminary stage of protein quantitation they have not yet been assigned any measured absolute biological values, merely their average OD/cell. In this aspect the invention reduces "misclassification error" (categorical false positives and negatives) in immunohistopathological analyses. It simply helps in answering the question: "Does this tissue section contain any of the abnormal protein to be analyzed"?

The second aspect of the invention is to utilize these same control cells as "calibration cells" in order to translate the optical density units of cell imaging into biologically meaningful measures of protein dosage at the level of the individual organelle, cell, tumor, tissue, or patient. The method provides, for the first time, batch-specific standard curves expressed as a continuous quantitative function that are applicable to any lab or immunostaining procedure. These continuous functions are superior to the ordinal ranking methods of the prior art, which—either with or without CID—ultimately forced one to assign ad hoc relative categories to degrees of IHC staining. The quantitative scoring method of the present invention provides more objectivity, accuracy, reproducibility, biological validity, and consistency among observers than has hitherto been possible. By creating absolute "interval-level" units of measurement, the present invention makes it possible to apply the discriminatory power and precision of multivariate parametric statistical tests in cellular protein quantitation.

The embodiment of the invention in the examples below relates to p53 in a particular "test" population with colorectal dysplasia; the analysis of their tissue and blood demonstrates the potential of the present invention to improve protein quantitation, cancer diagnosis specificity, tailor and monitor oncology treatment, and to provide a tool for more exact and powerful prognosis. However, the invention can be applied to any disease-associated protein for which for adequate cultured cell controls and suitable antibodies exist.

The present invention makes use of a method of cultured cell preparation, which immobilizes the cells in a solid hydrophilic matrix. The resulting matrix of immobilized, cultured cells behaves much like a sample of tissue, and can be fixed, sectioned, and stained in the same manner as a tissue sample. The hydrophilic matrix may be based on protein, e.g. gelatin, or on a hydrophilic polymer such as acrylamide or an acrylamide derivative, but is preferably a low-melting solution of an oligosaccharide such as pectin or agarose. More preferably the matrix is agarose, and most preferably a low-temperature agarose gelatin. Immobilization of cells in an inert, stable, physiologic-temperature matrix avoids the incomparability of frozen cell pellets compared to formalin-fixed, paraffin-embedded tissue with respect to protein denaturing, disruption of cell morphology, differing antibody affinities, and fixation artifacts. The use of thermally meltable matrix materials is preferred over the use of chemically polymerized polymers, such as acrylamide, because of the simple and reliable process of solidification provided by temperature control.

Although the matrix of immobilized cells may be treated in the same manner as a tissue sample, it is preferable that it not be subjected to fixation beyond the minimum necessary to preserve structural features and prevent diffusion of the protein of interest away from those structures. Preferably, the fixation will be in normal buffered formalin (NBF), or the equivalent treatment, and most preferably this will be carried out on the cultured cells prior to immobilization in the hydrophilic matrix. The fixation time is preferably less than four hours in NBF, more preferably less than two hours, and even more preferably less than one hour in NBF (or the equivalent treatment). Most preferably the fixation is conducted in NBF for less than thirty minutes, for example ten minutes or less. Treatments equivalent to fixation with NBF, such as for example fixation with acrolein, glutaraldehyde, or cyanuric chloride, are known to those of skill in the art.[125, 130]

In a preferred embodiment, fixation and staining of the cultured cells are carried out with the same reagents, but are optimized separately from the fixation and staining of the tissue specimen upon which protein quantitation is being carried out. This is in contrast to prior art methods which emphasized the importance of identical treatment at all stages of processing.

Storage of colorectal adenocarcinoma tissue blocks for 13 years reportedly has no appreciable effect on the levels of nuclear accumulation of both p53 and BCL-2 proteins as scored by cell imaging densitometry.[37] This was true for the proportion of positive ($\geq 10\%$ cell nuclei) cases, as well as the average intensity/cell, even though the more sensitive and reliable "antigen retrieval" treatment was not used for the p53 staining. After fixing and paraffin embedding, the immobilized cells of the present invention provide a reference sample that can be reasonably expected to be as durable and permanent as any paraffin-embedded tissue sample. A single cell pellet from a typical 75mm$^2$ culture flask can provide hundreds of calibration paraffin sections, which are suitable for commercial production and sale.

By way of illustration, the application of the invention to the quantitation of mutant p53 protein in colorectal adenomas and adenocarcinomas, and the resulting improvement in accuracy of diagnosis and prognosis, is described below.

Thus, one object of the invention is to provide a method for preparing cultured cells for immunostaining, which comprises the step of immobilizing the cells in a hydrophilic matrix. Preferably, the matrix is an aqueous gel of a polymer chosen from the group consisting of proteins, oligosaccharides, and poly(acrylamide). In specific embodiments, the matrix is an aqueous gel of a polymer chosen from the group consisting of gelatin, agarose, pectin, and poly(acrylamide). Preferably the matrix is an aqueous gel of agarose, and the agarose is most preferably a low-melting point agarose.

It is another object of the invention to provide a method of preparing calibration slides for a cell imaging densitometer, comprising the steps of:
  (a) immobilizing cultured cells in a hydrophilic matrix;
  (b) placing the matrix in molten paraffin;
  (c) cooling the molten paraffin until it solidifies; and
  (d) without substantial intervening fixation, sectioning the solidified paraffin containing the immobilized cells into at least one thin slice suitable for optical microscopy.

In this method, the cultured cells are preferably contacted with a tissue fixative prior to immobilization in the hydrophilic matrix. The method preferably further comprises the step of contacting the paraffin slice with a first antibody. The first antibody is preferably conjugated to a chromogenic or fluorogenic reagent.

In an alternative embodiment, the method further comprises the step of contacting the paraffin slice with a second antibody having binding affinity for the first antibody, the second antibody preferably being conjugated to a chromogenic or fluorogenic reagent.

In yet another embodiment, the first antibody is conjugated to biotin. Preferably, the slice is then contacted with a biotinylated chromogenic or fluorogenic reagent in the presence of avidin or streptavidin.

It is another object of the invention to provide a method for measuring the amount of a protein of interest in a cell or a cell organelle, comprising the steps of:
  (a) affixing said cell to a microscope slide;
  (b) staining said cell with an immunohistochemical stain;
  (c) measuring with a cell imaging densitometer the area and density of the stain within the cell or cell organelle;
  (d) calculating the summed optical density of the stain within the cell or cell organelle; and
  (e) converting the summed optical density into the amount of protein of interest, by reference to
    (i) a calibration slide prepared according to the method of the invention described above, and stained with the same immunohistochemical stain as was used in step (b); and
    (ii) the amount of protein of interest actually in the cells or organelles on the calibration slide, as measured by an assay of the protein of interest in a sample of the cells.

In the above-described methods, the protein of interest is preferably a tumor-associated protein, and preferably the cell is a tumor cell. The tumor cell is preferably fixed in a paraffin tissue section.

It is yet another object of the invention to provide a method of calculating a patient's body burden of a tumor-associated protein of interest, comprising the steps of:
  (a) measuring the amount of the protein of interest in one or more cells taken from one or more of said patient's tumors, by any of the methods described above;
  (b) converting the amount of protein determined in step (a) into the amount of protein in the tumor from which the cell was obtained; and
  (c) adding the amount of protein in each tumor to obtain the total amount of protein in the patient's tumors.

Another object of the invention is to provide a method of calculating the probable clinical outcome of cancer for a patient, comprising the steps of:
  (a) providing a statistically-derived continuous function relating the body burden of a tumor-associated protein, or the amount of a tumor-associated protein within the patient's tumor cells, to clinical outcome, in a population of patients with the same cancer;
  (b) measuring the patient's body burden of the tumor-associated protein, or the amount of a tumor-associated protein within the patient's tumor cells, by any of the methods described above; and
  (c) using the continuous function provided in step (a) to calculate the probable clinical outcome.

In all of the above methods involving a tumor-associated protein, a preferred tumor-associated protein is p53$^{mut}$.

Another object of the invention is to provide a method of selecting a patient for p53-specific therapy, which comprises measuring the patient's body burden of the tumor-associated protein, or the amount of a tumor-associated protein within the patient's tumor cells, by any of the methods described above. A preferred p53-selective therapy is genetic therapy with p53-encoding DNA.

Another object of the invention is to provide a method of monitoring the effectiveness or progress of a p53-specific therapy, which comprises measuring the patient's body burden of the tumor-associated protein, or the amount of a tumor-associated protein within the patient's tumor cells, on a per-cell basis, by any of the methods described above.

Preferred p53 selective therapies include in situ treatment with p53 peptides or p53$^{wt}$ DNA.

DETAILED DESCRIPTION OF THE INVENTION

1. Quantitation of Tumor-associated Proteins

Figure 1:
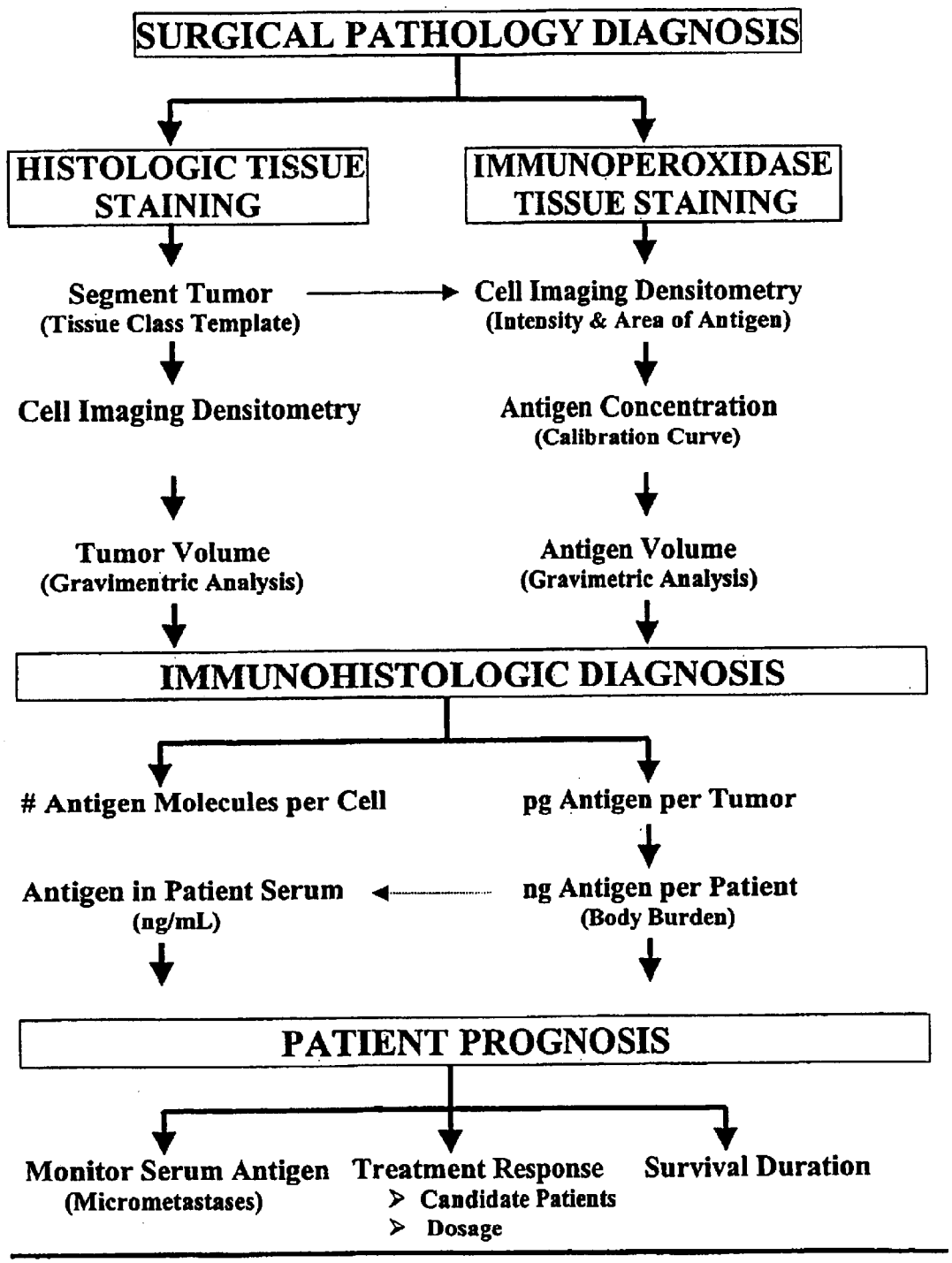
FIG. 1: Overview of the Approach. The method's linkage of traditional histopathology with quantitative immunostaining and cell imaging densitometry. The different measures derived therefrom and their clinical purposes.
Figure 2:
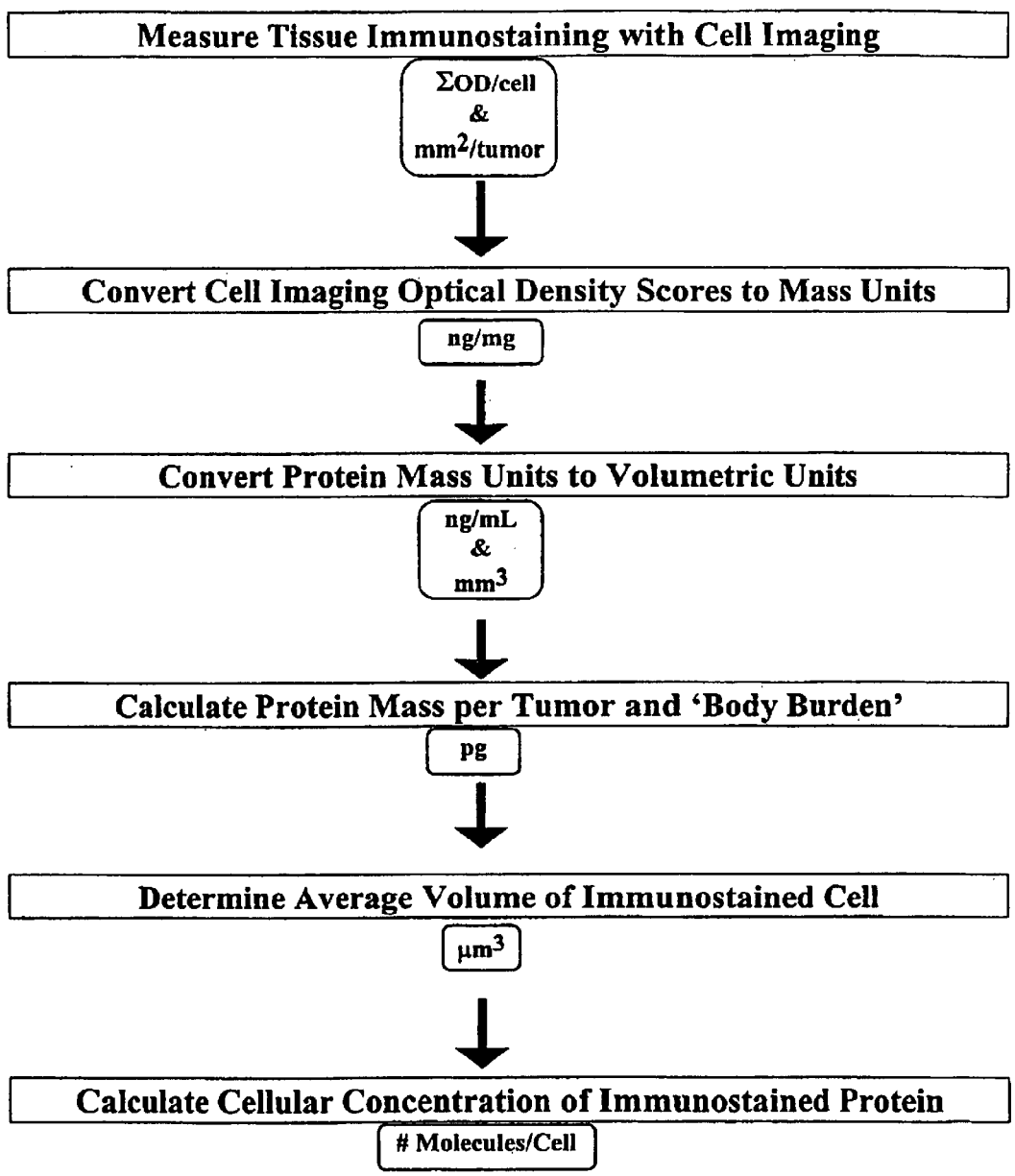
FIG. 2: Antigen Quantitation. The sequence of quantitation steps and their units.

The signal that activates p53$^{wt}$ for either arrest or death is DNA damage and it is the p53 protein itself that recognizes small insertions and deletions in the DNA [38]. p53-dependent apoptosis is mediated by p53's transcriptional promotion or suppression of the downstream effector genes listed in Table 2.

TABLE 2

| Apoptosis Genes | |
| --- | --- |
| Gene | Role in Apoptosis |
| Bcl-2 | Inhibits (binds with Bax and Bak) |
| Bax | Promotes (binds with Bcl-2) |
| Bcl-XL | Inhibits |
| Bcl-XS | Promotes |
| Bad | Promotes |
| Bak | Promotes |
| ICE | Promotes |
| Mch-2 | Promotes |
| Mch-1 | Inhibits |
| Fas | Promotes |
| DAD1 | Inhibits |
| p53 | Promotes (enhances transcriptional activation or repression of Bax, Bcl and Bak proteins) |

Thus, the methods of the present invention could be applied to quantitate many proteins, including, for example, those in Table 2, in order to establish their diagnostic and prognostic utility, and then to take advantage of any such utility for the purposes of diagnosis, evaluation of therapy, and prognosis.

The term "molecular biology" is often taken to mean DNA and RNA, to the exclusion of protein. One result of this simplistic view is that, upon detecting no DNA polymorphisms or gene mutations in tumor tissue which exhibits immunostaining, the latter result is often characterized as a "false positive" (FP), and is usually ascribed to antibody cross reactivity.[39] Certainly, it is crucial to know the identity or locus of gene mutations, chromosome deletions or translocations, etc. In the case of p53, whether the gene acts as a dominant or recessive tumor suppressor in human tumors (or tumor cell lines) depends upon which DNA codon is mutated.[40] This also influences the extent to which mutated p53 will cooperate with mutant K-ras in promoting tumorigenicity.[41] However, even with regard to genetic analysis, it is not enough to simply itemize a categorical list of which DNA alterations are present or absent. Even simple Mendelian analysis of inherited traits attempts to measure the actual impact of the inherited trait at the phenotypic level from the analysis of the relative dominance of the studied gene compared to other genes, the conditions in the rest of the genome, and environmental conditions.[42] What the present invention makes possible in quantifying p53 protein in colorectal tumorigenicity is the application of this approach to the cell, rather than to the individual, and to treat a particular malfunctioning somatic gene (p53), rather than one inherited in a germline.

As a general rule, relying exclusively upon this approach is, of course, incomplete. Even the use of an antibody, such as PAb240, which captures a wide variety of common p53 mutations (due to a shared alteration in p53 protein conformation), is not enough. Clinically speaking, it is necessary to know which change, if any, will occur in one or more of p53's biological functions as a result of the specific mutation, especially since certain mutations have no detrimental effect upon p53s behavior.[43] Fortunately, there does exist a yeast functional assay designed to test for the loss of p53's DNA transcription activity [44] to determine the significance of the accumulation of particular forms of inactivated p53 protein.

By changing the units of protein observation/measurement to either mass units or "molecules per cell", the present invention makes it possible to make direct quantitative comparisons among different cancer-related proteins of different molecular weights. This moves the field to a new paradigm: replacing histopathology with immuno-histopathology. This new approach does not rely upon a kind of "genetic determinism" that predicts disease outcome solely upon the identification of specific mutations. Rather, researchers can understand not only the functional significance of specific DNA mutations, but also the concentrations of oncogene and tumor suppressor proteins acting within the cell. Once the relative concentrations per cell of different proteins are known, one can estimate the reaction rates and equilibrium states of those inhibiting or cooperating proteins, or the extent to which transcription DNA binding sites are affected, the outcome of which will determine which normal functional pathway has been subverted. In the case of p53 in the colon this would mean the relative protein concentrations produced by genes such as p53, mdm, bax, bcl, MDR1, GADD45 [45] and by the genomes of the $E_1A$ or $E_1B$ adenoviruses.[46]

The present invention makes it possible, in principle, to evaluate the overall environment of the tumor cell [47]. This would include information as to which genes are mutated, deleted, or rearranged and which functional regions of the genes are affected; it would also consider the relative and absolute quantities/concentrations of those altered proteins being expressed and the percentage of affected tumor cells. For example, in addition to determining the location of p53 DNA mutations and their functional implications, one could also consider the cellular concentration of the altered p53 protein, as well as those of the endogenous cellular proteins, e.g., mdm-2, bcl, and bax, and oncoproteins such H and K-ras p21, that are either inhibiting or cooperating with p53 in the patient's tumor. The same is true for foreign proteins inactivating wild-type p53 [48], e.g., the E6 protein in the HPV16 and HPV18 strains of Human Papilloma Virus associated with cervical cancer.[49]

There are several reasons for employing p53 as a diagnostic marker. First, the normal p53 tumor suppressor protein has a cellular half-life of only 15–20 minutes, while that of the inactivated form is 5.5–7.0 hours.[50–53] Although normal p53 levels are nearly undetectable using immunostaining, the quantity of p53 in many transformed mammalian cells is 10–100× greater.[54] This rapid, extreme and stable accumulation of cancer protein makes for relatively easy immunohistologic identification in the patients' affected cells and greatly reduces the likelihood for mis-classifying their p53 status in tumor tissue or plasma. If wild-type (normal) p53 is inactivated by mutation, the detectability of its protein increases dramatically, due to changes in its post-translational conformation, rather than from increases in replication, transcription, or translation [55], thereby making a protein-based assay the logical method for quantification of mutant p53 gene expression.

However, inactivation of p53 due to binding by exogenous viral proteins or endogenous cellular proteins may or may not lead to the same accumulation of p53. The large T antigen of the SV40 virus stabilizes p53 upon binding to it (reducing p53s capacity to initiate transcription of downstream proteins), and in the cases of HPV-16/18 and p53 in cervical cancer, wild-type p53 is inactivated through the degradation of the normal p53 protein by the viral E6 protein.[56] This would imply an inverse relation between the amount of detectable p53 and the extent of its inactivation in these cases. HPV has also been detected in colon cancer as well.[57]

Secondly, there are presently a number of commercially available and well-validated p53 antibodies. Some are polyclonal antibodies, which have the greatest affinity for p53, but which are less specific than monoclonal antibodies. Among the monoclonals, there are three broad types: some are mutant-specific for a particular epitope; some bind to a particular altered protein conformation created by a wide variety of mutations affecting the core DNA-binding region; and there are "pantropic" antibodies that react with both wild-type and mutated p53 by binding to regions not affected by mutations. Many of these antibodies are suitable for paraffin-section immunohistology, ELISA, and Western blotting. The pantropic antibodies have the ability to detect any stabilized, non-functional p53, nearly all of which will be mutated. They may also detect some transient, high expression of wild-type functional p53 responding to DNA damage, hyperplasia or dysplasia. However, given the short half-life of wild-type p53, this is likely to be present in small amounts. Likewise, the p53 detection may be exposure-related rather than disease-related.[58] If such data is available, and if sample size allows, one could and should control for potential exposure confounders in the p53 data analysis. The presence of detectable p53 may also be related to a biological condition other than colorectal cancer.[59] This is more likely to be the case in plasma, however, rather than organ-specific tissue sections, which is why plasma needs to first be validated by detection in individual patients' tissue before relying upon it to do prognosis, detect occult micrometastases in the blood, predict therapy outcome, etc.

The existence of these multi-faceted antibodies, combined with the fact that 1447 different p53 mutations have been identified among all types of human tumors [60, 61] has made immunohistology far cheaper and more practical than either DNA- or RNA-based assays. In the case of ELISA, there are commercial mutant and pantropic "sandwich" (double-antibody) type ELISA kits available that provide for sensitive and specific detection in p53-expressing cultured cell lysates. The combination of sensitive and specific assays and standardized and biologically relevant cell lines make possible the accurate immunostaining calibration controls of the present invention.

Third, microwaving samples in order to "unmask" (unfold) a large variety of cancer-related proteins facilitates subsequent p53 detection in paraffin tissue sections by the pantropic DO-1 anti-p53 antibody [62]. This lab technique enables very intense nuclear staining and an unambiguous signal/noise ratio of 92.2 (for immunostaining a p53$^+$ adenocarcinoma tissue section with DO-1 versus with a class-matched IgG myeloma protein control antibody).

Fourth, in order to demonstrate the advantages of the present invention in the area of diagnosis and prognosis, a substantial body of existing relevant literature from medical oncology and cancer biology is helpful in drawing conclusions from the immunostaining results. In the case of p53, there were 1,869 articles published on the gene and/or its protein product in 1996 alone.[63] Numerous publications deal with immunostaining techniques and the use of "cell imaging" technology for accurately scoring this staining. Another well-documented area is the investigation of the correlation between staining for p53 (and other cancer proteins such as c-erb-B2) in colorectal,[19,28,64,] breast, [65] and lung cancer[31] patients tumor tissue and plasma. These studies found an association between p53 in tissue and plasma and some of the plasma expression correlated with histology-pathology variables. Furthermore, some of the authors created continuous (albeit relative) scores for the p53 immunostaining in order to better correlate p53 levels in lung cancer tissue with the concentration (ng/ml) of p53 in patient serum, as detected with the ELISA. The two measures correlated, both with each other and with tumor grade and stage.[31] There is evidence that using the ELISA on the serum/plasma of colorectal cancer patients offers an effective and less invasive technique of monitoring cancer progression following surgical resection.[29] Using the cell imaging method of the present invention to replace the current relative measures of p53 expression in tissue sections with their absolute amounts would improve the accuracy of this approach.

There are also reasons for selecting a patient population afflicted with colorectal adenoma and/or adenocarcinoma. Prior research has demonstrated a strong link between p53 inactivation and both the incidence and mortality from colorectal cancer. Therefore, the results of the quantification of p53 protein could be expected to have clinical relevance. Furthermore, there was an existing case/control study population recruited by the Colonoscopy Study Group at Columbia-Presbyterian Medical Center in New York, which had been selected on a sound clinical and epidemiological basis. These patients had provided both plasma and formalin- (or Bouin's-) fixed paraffin tissue blocks for which the diagnosis and histologic staining had already been performed by the CPMC Pathology Department. Negative control tissue specimens of the colon and rectum were available from the St. Luke-Roosevelt Hospital Gastroenterology Department.

Also, the link between inactivated p53 and colorectal cancer and the pre-cancerous adenoma is well documented. Not only is there a strong and consistent association between p53 and these diseases, there are reports showing the connections between various tumor suppressors and oncogenes. There are comparisons of DNA, RNA, and protein, and in vitro and transgenic animal experiments (mouse skin papillomas), that shed light on the functional significance of the expression of p53 and other molecular biomarkers.

The accurate, sensitive, and reliable surgical technique of colonoscopy for the detection and excision of the tumors greatly reduced the tissue sampling error. Sensitive and specific techniques and accurate and unbiased cell imaging equipment and procedures are of little use if the colorectal tissue samples do not include the entire tumor volume; otherwise the percentage of False Negative (FN) patients and tumors is increased. Finally, colorectal cancer is a common, and often lethal, form of cancer, so there is a significant public health benefit to be gained from this application of the invention.

A number of published studies [66] have investigated the connection between p53 DNA or p53 protein status and prognosis for various types of cancer. The majority of these studies used immunohistochemistry to detect p53 protein over-expression as a proxy for inactivated p53. A perusal of these same studies [66] reveals that:

(1) there is no uniformity of method in patient selection, antibody choice and concentration, or laboratory technique;

(2) there are arbitrary definitions of the threshold for a p53$^+$ cell and what constitutes a sufficient percentage of p53$^+$ cells for a sample to be considered positive;

(3) often there is no healthy control patient population used as a comparison group; and (4) usually, there is no multivariate analysis employed to isolate the independent contribution of aberrant p53 protein to patient survival.

Most tellingly, the major determinant of whether a study found a negative association between p53 over-expression and survival was sample size: only when the sample was adequately large was there sufficient statistical power to see an association. Despite all the admittedly strong experimental biological evidence to the contrary, the reviewers concluded that p53 inactivation has a relatively weak association with clinical survival.[66] This may or may not be the case; the present invention provides a fundamentally sound methodology that will help find a more reliable answer to the question.

Keeping the above caveats in mind, nuclear [67–69] or especially, cytoplasmic [70, 71] p53 paraffin section immunostaining has shown itself, in at least some studies, to be an independent prognosticator for colorectal cancer survival and recurrence [72]. Other such prognostic molecular aberrations have included deletion of p53 and/or histologic stage of the tumor [73, 74], deletion of the DCC gene, p53 mutations [75], DNA aneuploidy, and BCL-2 expression. Mutation of K-ras and deletion of the APC and MCC genes, on the other hand, have not predicted survival [76]. In some studies in which an association was seen, the authors were able to successfully rank the amount of staining present in a given tissue specimen. In addition to colorectal cancer, an association between p53/p53 status and survival has at times, [77–78] but not always, [79] been observed for breast cancer. It has also been found in cancers of the lung, ovary [80], squamous epithelial cells of the head and neck, [81] and urinary tract.[82]

While lost p53 gene function has been consistently observed in a small minority of colorectal adenomas (~10%, the proportion increasing rapidly with increases in the severity of dysplasia, non-tubular histologic type, size, and synchronous or contiguous cancer), the fraction reaches 50–70% in colorectal cancers.[83–85] The percentage of tumor cells that are p53-aberrant varies from <1% for mildly dysplastic adenomas to ≦100% for malignant lesions. The timing of abnormal or deleted p53 is, perhaps, even more convincingly demonstrated in those studies that looked at those patients or tumors in which there were either synchronous adenomas/adenocarcinomas or cancer within the head of an adenoma. Here the same relative percentages of p53$^+$ cells held up, showing the apparent role of p53 inactivation in the malignant conversion to focal carcinoma in colorectal carcinogenesis [86, 87]. The fact that Li-Fraumeni syndrome individuals, who have germ-line mutations in p53 at birth, do not have increased risk of colorectal cancer logically suggests that early (and solitary?) p53 loss does not fit the genetic pattern for colorectal cancer [88, 89]. There do not appear to be any colorectal cancer studies that detected abnormal p53 in adjacent normal tissue.

It may also be worthwhile to quantify inactivated p53 in individual cancer patients in order to predict their response to post-surgical adjuvant treatment (chemotherapy or radiotherapy). There already is considerable evidence from both in vitro and clinical studies, for various types of cancer (including colorectal), showing that the presence of inactivated p53 in patient tumors worsens their therapeutic response. This is partly because the loss of normal p53 greatly reduces what would other wise be the greater apoptotic response in cancer cells relative to that of healthy cells following treatment. It is this differential rate of induced cell death that is the whole basis for such drugs' "therapeutic index". Once inactivated, p53 neither delays the DNA replication of tumor cell damaged DNA, nor initiates apoptosis of such cells; instead, the cancer cells become more resistant than the normal cells to the cytotoxic effects of the therapy [90–95]. Furthermore, unlike normal p53, dysfunctional p53 (and c-H-Ras-1) stimulates rather than suppresses the transcription promoter for the multi-drug resistance (MDR-1) gene, which further increases tumor cells resistance to chemotherapeutic drugs.[95, 96]

Therefore, the adenoma and adenocarcinoma subjects in this study were followed prospectively after their initial diagnoses to see if the quantification of p53 could be of benefit in predicting either survival or chemotherapy response. For the same reason, p53 ELISA measurements on the plasma of a subset of tumor-positive and tumor-negative patients were conducted to see if the same response could be predicted using the less invasive procedure of post-diagnostic blood analysis. Finally, the availability of well-characterized, cultured cancer cell lines whose p53 genome status is known made it possible to provide a p53 "gold standard", against which the p53 protein found in the patients tissue sections could be quantified. The ELISA p53 concentrations from the lysates of three cell lines were used to create separate standard curves for each immunostained batch of tissue.

To make the in vitro⇆in vivo inference a valid one, the cultured cells were sectioned in a manner intended to approximate the conditions that surgical specimens typically undergo when they are used to prepare tissue [97] sections, namely heated paraffin wax, alcohol, fixation (preservation), and drying upon a glass slide. Following fixation, but prior to paraffin embedding, these cellular calibration controls were aggregated in low-temperature agarose gelatin. This facilitated the post-fixation treatment in a dehydrating alcohol series. It also allowed aggregation of sufficient numbers of cells to speed their scoring by cell imaging, and to reproduce the tissue sections immunostaining conditions, i.e., the relative concentrations of the cells and the immunohistochemistry reactants. These cultured cell calibration controls were also histologically stained and measured to verify that their morphology and size were very similar to the colorectal crypt cells of the patients (Table 3).

2. Methods

Figure 10:
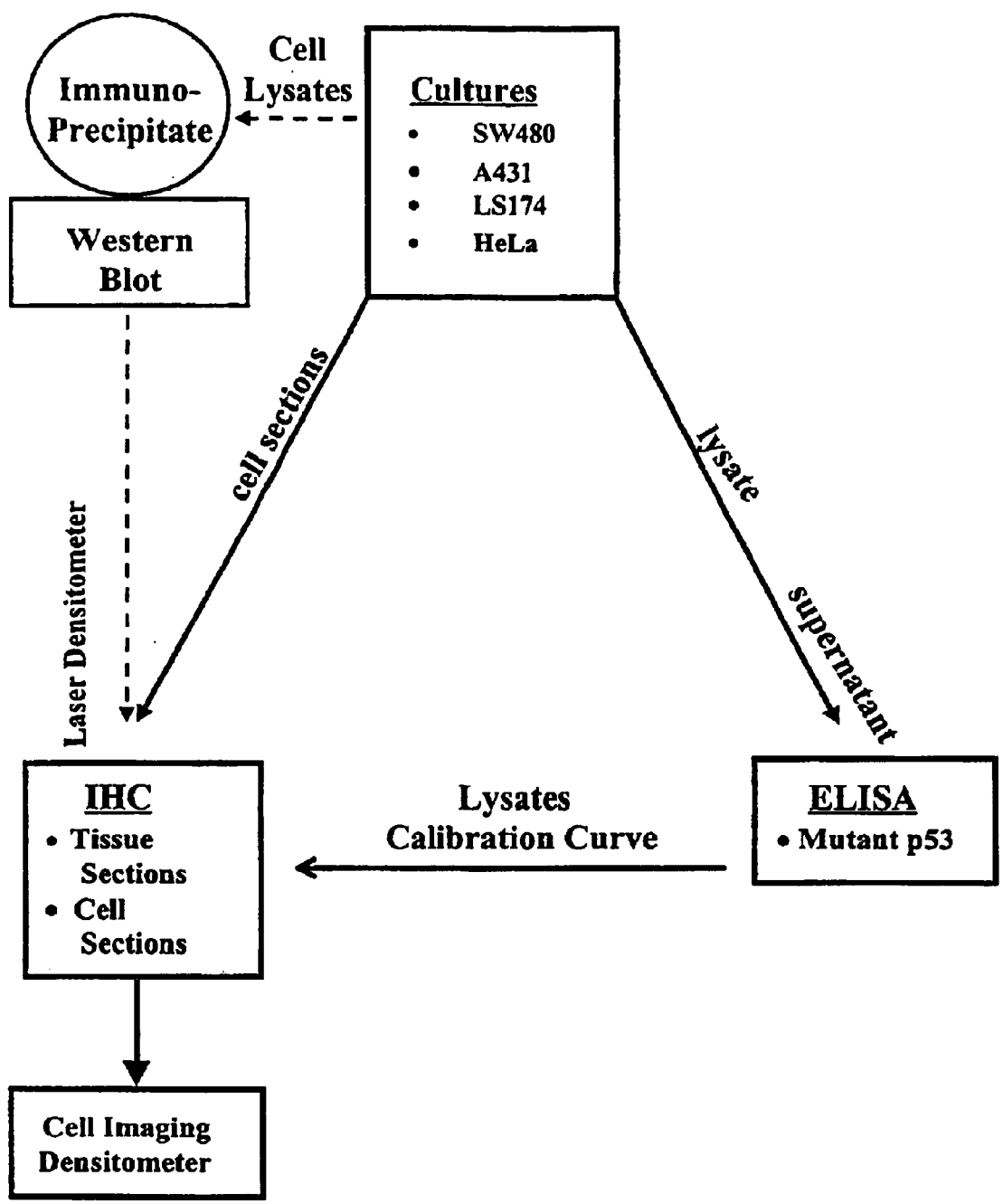
FIG. 10: Laboratory Assays Used and Their Linkage. Shows the linkage of the laboratory assays underlying the method.

One object of the present invention is to provide a reproducible and reliable standardization for the current practice of IHC. For this, the lab work has to be simple, fast, cheap, and made up of interchangeable parts that can be applied to various settings without requiring great technical expertise or extensive training. Three of the five assays—cell culture, ELISA, and IHC—are required; the other two—immunoprecipitation of the calibration cell lysates, followed by the loading of the precipitates on a Western blot gel—are optional (FIG. 10). The purpose of the latter two is to improve the accuracy of the IHC quantitation, where necessary, by adjusting the lysate calibration curve in order to account for any protein underestimates, due to identifiable interfering factors between the antigen and the ELISA antibodies. The percentage underestimate for the particular calibration lysates can be gauged from the Western blot and used to alter the slope of the IHC standard curve. In the case of p53, an example of interfering proteins is the family of Heat Shock Proteins (HSP), which are known to bind mutant p53.[98]

The cancer cells used for standardization and calibration were selected from among 18 currently available human colorectal tumor cell lines already standardized for quality by the American Type Culture Collection (ATCC) and whose p53 mutation status had been demonstrated in peer-reviewed scientific journals. They are inexpensive, readily available, and the conditions of their cultures well established. As will be described in the examples, once a pair of cell pellets for a given cell line is collected and embedded (one for the ELISA, one for IHC) the embedded cells can be saved indefinitely. The large number of calibration sections created (ca. 800 sections from a 4mm diameter cell pellet) are sufficient to last for hundreds of staining batches. To eliminate variability due to batch-to-batch variations in staining intensity, which may arise from variations in operator technique, age and quality of immunochemical reagents, etc., at least one calibration slide is included with each batch of tissue sample slides. The calibration slide is mounted in the same slide holder as the samples, and is therefore treated in exactly the same manner with exactly the same reagents throughout the sample preparation and sample staining process. The conversion of a sample's ΣOD value to its p53 quantity is then made with reference to the series of calibration slides co-treated (fixed and stained) with that particular batch of sample tissue slides.

For several oncogenes and tumor suppressor gene proteins, both the ELISA kits and the IHC monoclonal antibodies are widely-available and sold commercially; in the case of p53 both are already well-characterized and the quality control is established. A single ELISA calibration would likewise serve to interpret those hundreds of embedded cell sections for each of the different calibration cell lines. Current fixation, embedding, sectioning, and H&E procedures used in the great majority of surgical pathology departments do not have to be altered in practicing the present invention. While manual immunoperoxidase staining was used in the embodiment exemplified herein, other embodiments of the invention may employ any colorimetric staining procedure, manual or automated. Both the staining and the scoring of the slides can be routine procedures. The Western blot is needed only once at the outset to establish a correction factor, if warranted, and the ELISA assay is needed only once for a given set of calibration standards. Once these mass concentrations of the protein of interest are known, these respective constants are correlated with their corresponding varying average ΣOD/cell on the calibration slide for each staining batch.

In a preferred embodiment of the invention cultured tumor cell lines are employed for calibration. In one alternative embodiment, engineered cell lines containing expression vectors are used for the calibration cells. The latter embodiment permits the user to control the range of protein expression captured in the paraffin blocks, and to create evenly-distributed multiple data points for the immunostaining calibration curve. If the protein to be quantified is present in cultivated cell lines grown for therapeutic purpose—rather than in patient tissue—the same calibration cells may be used to measure this protein. In this optional embodiment of the invention the calibration cells are processed in the same way as the cell sample. Instead of imitating the fixation, embedding and sectioning of human tissue, in this embodiment both the cell standards and the cell sample may be smeared or, preferably, spun onto microscope slides with a low-speed centrifuge designed for this purpose, using predetermined equal volumes and concentrations of the respective cell suspensions for each slide. After fixation and adhering the cells to the slide with brief drying, the calibration standards and the sample cells undergo all the identical steps described in the preferred embodiment of the invention, including a CID calibration curve suitable for this purpose.

Another object of the invention is to provide a diagnostic test for the staging of the disease to help in planning clinical intervention. This requires some specificity and the ability to link the IHC very closely with the morphology of the tissue. The in situ nature of the method and the linking of the H&E staining and the IHC with the "Tissue Class Template" handles this requirement nicely (FIG. 1). The accuracy and ease of colonoscopy makes this particularly valuable for colorectal cancer. Currently, aside from histopathology, patient prognosis is predicted by blood CEA. While both, particularly histologic stage, are helpful, they lack the specificity to predict the future occurrence of colorectal adenocarcinoma complications. This is analogous to the inability of the "glucose intolerance" test to predict associated diabetic sequelae, such as renal disease, acute ketoacidosis, blindness, etc.[99] For adenomas the complication is a higher risk of developing adenocarcinoma. For the adenocarcinomas the molecular complications are chromosomal non-disjunction and deletion of the DDC gene, and the clinical sequelae are recurrence, metastasis, resistance to chemotherapy, increased probability of death, and a survival duration inversely proportional to the p53 body burden.

IHC for inactivated p53 is not intended as a screening test. Whether a patient is sick is defined by the H&E morphology slide; the risk of incorrect molecular staging is unnecessarily aggressive treatment. Given the current modest success for adjuvant therapy, false positives would be as big of a problem as false negatives because they would trigger aggressive, but often futile treatment. The determination of the cut-off point for $p53^+$ should factor in these priorities. Therefore, conservative criteria for defining a positive were adopted:

1) focal expression of the staining in contiguous, homogeneous clusters of crypt cells;
2) two standard deviations above the mean Average OD/cell, i.e., top 2.5%, among the Hospital Controls;
3) with respect to the Average OD/cell, corroboration of the hospital controls' LLD with that of the $p53^-$ LS174T Calibration Cells;
4) the histologic specificity of nuclear staining; and
5) the use of two different sandwich ELISA kits (both of which use a pair of anti-p53 antibodies).

TABLE 3

Immunohistology Calibration Cells

| Species | Human | Human | Human |
|---|---|---|---|
| Histologic Type | Colorectal Adenocarcinoma | Vulvar Carcinoma | Colorectal Adenocarcinoma |
| p53 Chromosome (17p) Copies | normal/normal | mutant/deletion | mutant/deletion |
| Mutant Genotype | none N.A. | a.a. Δ 273:R→H | a.a. Δ 273:R→H, 309:P→S |
| Nuclear Diameter (μm) | 6.02 | 8.50 | 8.62 |
| Cell Diameter (μm) | 7.17 | 10.80 | 10.18 |
| Nuclear Area (μm²) | 28.47 | 56.67 | 58.33 |
| Nuclear Volume [est.] (μm³) | 114.21 | 321.49 | 335.30 |
| Cellular Area [est.] (μm²) | 40.39 | 91.64 | 81.42 |
| Cellular Volume [est.] (μm³) | 1381 | 5488 | 5804 |
| p53 Immunostain @1:400 (Batch 19) | | | |
| Sum O.D./cell | 17.40 | 285.40 | 412.80 |
| Ave. O.D./cell | 0.53 | 5.54 | 6.63 |
| Cell Lysate Total Protein [mg/mL] | | | |
| Batch A | 1.18 (11.8) | 0.68 (6.8) | 1.22 (12.2) |
| Batch B | 2.12 (21.2) | 1.20 (12.0) | 2.05 (20.5) |
| Average | 1.65 (16.5) | 0.94 (9.4) | 1.64 (16.4) |
| ng p53/mg | | | |
| mutant | 0.13 | 6.92 | 7.94 |
| Pantropic | 0.06 | 2.86 | 12.44 |
| Molecules $p53^{mut}$ Cell | 22 | 4264 | 8314 |

3. Cell Culture

The three cell lines used for calibration were LS174T, A431, and SW480 (Table 3). The use of human carcinoma cell lines allowed for the possibility that some normal p53 would be expressed (even in the LS174T) due the exercise of its normal function in dysplastic cells. Thus, the $p53^-$ calibration cells would serve as specificity controls, not simply lab controls against staining artifact. The extent of this transient staining in wild-type p53 by the DO-1 pantropic antibody, indicative of the body's healthy response to the dysplasia, was discounted in defining "true positive" staining in the sample tissue. This, in fact, did occur. There was a very slight "false positive" "mosaic" pattern in both tissue and the $p53^-$ calibration cells, as discussed above. The characteristics of these three cell lines in terms of reactivity with the pAb240 (mutant) and pAb 1801 (pantropic) antibodies in immunoperoxidase cytometry staining, Western blots, and mutant and pantropic ELISAs is already known. [100] Furthermore, p53 DNA sequencing and mutant/normal protein expression in various assays has been already established: among the two colorectal cell lines, both the LS174T and SW480 have mutated K-ras12, although only SW480 has the mutated p53 gene.[101]

4. Antibodies

The antibodies, ELISA kits, procedures, and quality control information used herein are commercially available, e.g. from Calbiochem (San Diego, Calif.) and Oncogene Science Diagnostics (Cambridge, Mass.).[20, 98, 102, 103] The pantropic p53 mouse monoclonal antibody is specific for human p53 and is the manufacturer's recommended choice for the human protein in paraffin sections. Recommended positive controls are the tumor cell lines A43 1, SKBR3, and HeLa. For a tissue control, breast carcinoma is recommended, and for negative controls SKOV3 (ovarian adenocarcinoma) and normal skin. The human p53 reactive epitope of DO-1 is between amino acids 21–25 at the $NH_2$ terminal. Responding best, when the slides are subjected to microwave treatment prior to antibody incubation[62], the DO-1 clone is reportedly the best available for formalin-fixed/paraffin-section IHC.[104] The reactive epitope recognized by pAb 240 clone Ab-3 is within the DNA binding region of p53, and is located between amino acids 212–217. This epitope is revealed only when the protein is mutated or denatured. Thus, the pAb240 mouse monoclonal recognizes human, mouse, and rat mutant p53s, but not the normal conformation, unless the protein is denatured. This is why negative control cells and tissue are required, since proteins are prone to denaturation in the course of microwave treatment. The pAb 240 antibody has been used extensively in frozen section IHC, but does not react well in formalin/paraffin sections.[103] One author was not able to detect p53 in SW480 cell lysate in IP/Western blotting using this antibody, although able to do so with pAb1620 and pAb421. [105] It is suitable for IP, immunofluorescence, Western blotting, frozen sections, and flow cytometry. However, it is not specific for mutant p53 in Westerns, recognizing the denatured wild-type protein, too. The same positive (including A431) and negative controls are recommended as for DO-1.[102]

The point mutations to the central region of p53 that make it unable to bind DNA also cause the common conformational effects that allow the pAb 240 to recognize the transformed protein.[61] Therefore, nearly all of those mutations affecting patient survival will lead to positive immunostaining of the cell lysates in the ELISA. In fact p53 overexpression in a variety of colorectal cell lines has been shown to have 100% specificity for p53 mutation (100% TN). In other words, if they are p53$^+$, the cells are truly mutated.[105] Perhaps 15% of those mutations (deletions and insertions), which do not cause accumulation of protein, will be missed by p53 IHC (85% TP).[106] However, some of those lesions fall outside the DNA-binding core and will have no affect on disease progression and patient survival. Therefore, in terms of progression and survival, the sensitivity of the immunostaining will likely exceed the 85% estimate. Furthermore, in other cancers impacted by p53 inactivation, such as breast cancer, most of p53's loss of function is not due to mutation.[106] For such a disease, DNA sequencing of tumor tissue underestimates consequences to the patient from her loss of the "guardian of the genome".

5. Immunostaining

An avidin-biotin complex (ABC) immunoperoxidase staining system was employed for immunostaining. The label was reddish-brown (DAB, without $NiCl_2$). The counterstain was methyl green. The ABC was used because of its sensitivity, reproducibility, commercially-available kits with "batch-matched" avidin and biotin, and demonstrated quantitative stoichiometry with various antigens, including p53. The CMP program for the CAS-200 Cell Imaging Densitometer has its filters set up at 500 nm (brown) and 620 nm (blue-green), specifically for these widely-used primary and secondary stains. The blocking solution was normal horse serum because the secondary antibody was horse/anti-mouse IgG. The primary antibody was the DO-1 clone, a pantropic p53 mouse monoclonal.

The secondary antibody is against the fixed chain region of the DO-1 primary antibody, instead of to a second p53 epitope, so the immunohistology cannot lay claim to p53 specificity based upon antibodies binding to two separate epitopes. Others have proven the need to use MWO antigen retrieval in citrate or similar buffers when using DO-1 in order to "unmask" the reactive epitope, which is partly obscured by the fixation-induced cross-linkages.[62] In fact, it has been demonstrated that without such unmasking, the sheer (and unpredictable) amount of lost p53 immunostaining due to neutral buffered formalin (contrasted with alternative fixations of the same tissue) would have made Cell Imaging Quantification less reliable and sensitive.[107, 108]

The sensitivity of this ABC-enhanced peroxidase immunostaining is at least as good as that provided by immunofluorescence. With the proper cell imaging densitometry green filter (546 nm), this method has been shown to be able to read as few as 100 molecules/cell. Furthermore, there is reasonably linear stoichiometry over a wide range, i.e., 100–10,000 IgG molecules/cell for both the Average OD/cell and ΣOD/cell cell imaging densitometry measures. [109]

Figure 3:
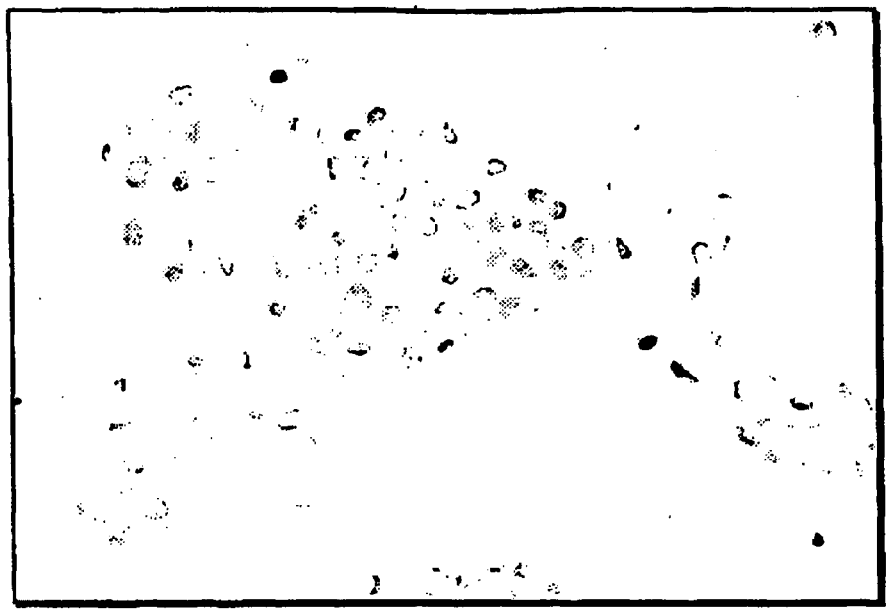
FIG. 3: p53$^-$ Calibration Cells. A computer-scanned photomicrograph of the LS174T calibration cells, immunostained with a pantropic anti-p53 antibody. These colorectal adenocarcinoma cells contain only normal p53.
Figure 4:
FIG. 4: p53$^+$ Calibration Cells. A computer-scanned photomicrograph of the A431 calibration cells, immunostained with the same anti-p53 antibody. These cancerous epithelial cells contain transformed p53 mutated at a single base.

Two of the three calibration cell lines described above were used in all immunostaining batches. For these calibration cells to serve as a proxy for tumor tissue, they had to experience the same conditions of tissue processing and immunoperoxidase staining as the tissue. Therefore, the calibration cells were both p53$^-$ (FIG. 3) and p53$^+$ (FIG. 4) controls. Infrequent (<<1%) and non-contiguous darkly stained cells were occasionally observed in the negative cell line LS174T; these were probably colorectal cancer cell nuclei whose evanescent p53$^{wt}$ expression had been caught by the pantropic p53 antibody, DO-1. Such isolated brown nuclei were ignored in the subsequent cell imaging scoring of tissue staining. Marginal staining limited to the edges of the entire section was also ignored, assuming it to be a tissue-drying lab artifact.

The p53$^+$ and p53$^-$ tissue controls were examined next. Both were tissue blocks previously stained for p53 with the DO-1 by the CPMC Surgical Pathology Department. The p53$^-$ control was a non-dysplastic colorectal specimen, the p53$^+$ tissue was from a ductal breast carcinoma tumor. Both were formalin/paraffin-processed. Bouin's-fixed colorectal tissue samples were also examined. The formalin-fixed specimens were immunostained separately and before the Bouin's-fixed slides, since the latter required a $Li_2CO_3$ washing step to remove picric acid. A Bouin's-fixed colorectal cancer biopsy was used as the p53$^+$ tissue control for those patient tissue samples similarly fixed.

Primary antibody was titered according to the best signal/noise ratio, as determined by CID. This was done with multiple sections per slide, so that all other batch conditions were held constant. The ideal dilution for the formalin and Bouin's tissue sections was 1:100 (1 μg/mL); for the calibration cells it was 1:400 (0.25 μg/mL) due to a less densely-packed target crypt cell population and the absence of stromal tissue. At these concentrations the S/N were as shown (Table 4). Comparison (a) is between the two calibration controls stained with each of the 18 batches of colorectal sample tissue sections. Contrast (b) is between a cancerous and normal tissue section selected at random.

Contrast (c) is between a random adenoma and the same normal hospital control tissue. Comparison (d) is the contrast between the "live" primary MAb (DO-1) and a "dummy" antibody (MOPC 141, an IgG$_{2a}$ mouse myeloma protein) incubation of the adenocarcinoma section @1:100 dilution. The experiment was done in one batch and used the identical IHC conditions as were eventually used for the samples. All tissue and calibration cell embedded pellets were formalin-fixed.

TABLE 4

Quality of Immunostaining using Monoclonal Antibody, DO-1

| p53$^+$ ↔ p53$^-$ | Signal/Noise Ratio | |
|---|---|---|
| | ΣOD/Cell | Average OD/Cell |
| a) A431 ↔ LS174T | 23.8 | 12.1 |
| b) Adenocarcinoma ↔ Normal | 29.8 | 11.7 |
| c) Adenoma ↔ Normal | 22.9 | 11.6 |
| d) DO-1 ↔ MOPC 141 | 92.2 | 64.3 |

Several things are apparent regarding the Immunohistology:
1. there is excellent specificity and sensitivity for aberrant p53 detection, as indicated by the large S/N for each comparison;
2. the calibration cells (a) are comparable to the tissue (b-c), as seen in their nearly identical S/N;
3. there is slightly greater p53 expression in the adenocarcinoma (b), compared to the adenoma (c);
4. the much greater S/N for the (+vs.−) antibodies (d) compared to the (+vs.−) tissue (b-c) suggests that the slight noise present was not due to lack of specificity for aberrant p53;
5. the CID and the immunostaining are consistent, and the calibration cells are comparable to the tissue with regard to nuclear size and staining intensity, as suggested by the consistent difference between the ΣOD/cell and average OD/cell ratios for comparisons a-c; and
6. The S/N for ΣOD/cell for both the cells (a) and the tissue (b-c) is nearly identical to the ratio of the half-lives of transformed vs. normal p53 (~22X), suggesting that the method of the invention provided a proportional measure of the underlying loss of biological function.

6. Cell Imaging Hardware and Software

There are a number of cell imaging microscopy systems that operate in a similar fashion, e.g., the CAS-200 (Becton Dickinson Inc., San Jose, Calif.) the BIOCOM 500 (Biocom, les Ulis, France) and the SAMBA 2005 (Alcatel, Grenoble, France). The basic design components are:

a microscope;

a color filter system, with matched color cameras;

computer programs and a digital gray-scale table for interpreting optical densities;

an image monitor for the microscope field image, and a text monitor for the interactive computer analysis;

a computer with at least one high-capacity disk drive; and a printer.

The microscope is optionally equipped with an automated stage and field selection system capable of increasing scoring speed. The color filters, each with its own color camera, create monochromatic light to be used for two purposes. The first is to alternately mask out the primary (antigen) and then the secondary (counterstain) color stains. The second purpose is to ensure that the light measured for optical density is of a single wavelength, so that the optical density of the stained cells will be proportional to the amount of the antigen present.[110] The operator must determine which are the target cells (in this case, intestinal crypt goblet, absorbing and paneth cells) and which are not (surrounding lymphocytes and stromal connective tissue). This is best accomplished using the companion H&E histology slide.

The computer programs are user-interactive and can perform many measurement tasks, including morphometric qualities, optical density averaging and integration, area comparisons, proliferation indices, direct true-to-scale measurement of cell and tissue dimensions, and many statistical calculations and measurement unit conversions. The microscope monitor allows the viewer to isolate and select cells, and set optical density thresholds in order to determine which staining intensities will be visible to the computer's gray-scale calculator. Use of an optical filter masking system allows the user to inform the computer which areas of the cellular objects are nuclear, cytoplasmic and membrane, and to allow it to score only the appropriate intra-cellular region. (In the case of accumulating p53, this was the nucleus.) The computer monitor screen allows the user to select the desired measurement program, chose among the menu-driven scoring options, and to request and display statistical results. Data can be simply printed or stored permanently in computer memory and exported later in spreadsheet or statistical package formats for analysis.

The cell imaging densitometer splits the magnified cells' image into two separate, color enhanced images. Red and green filters were used for methyl green and DAB nuclear staining. Since the red filter transmits brown and absorbs blue-green, it sees all the cell nuclei counterstained with the methyl green, regardless as to whether they contain the brown-staining aberrant p53$^+$ or the colorless normal p53. On the other hand, the green filter transmits light from the counterstain dye, but absorbs that of the (brown) DAB. Therefore, the p53$^+$ nuclei appear darker in optical density to the second optical camera and their pixels are scored.[Ref. 111; see also U.S. Pat. No. 5,008,185, which is incorporated herein by reference] By forming a color mask electronically, the CID can measure the total nuclear surface with the red filter/counterstain at the primary wave length. The antigen-brown regions within the nuclear area of each selected cell are measured at the secondary wavelength. By combining the two regions, the average nuclear area and average stained nuclear area ($\mu m^2$) per cell can be measured. Using the histologic and the immunostained slides for a patient, an additional computer program measures the extent of both total and antigen-positive tumor areas (mm$^2$) or the percentage positive area [U.S. Pat. No. 5,008,185]. Both the tumor and its antigen-expressing fraction expand by cell division contiguously in all directions. Therefore, assuming both areas are spherical and that the scored tissue section is representative of the entire paraffin block (see FIG. 13), these area measurements can be converted to tissue volumes. This allows the clinician to estimate the patient's total tumor and antigen burdens in the affected organ.

The operator must set numeric sensitivity thresholds defining how dark brown (and green) the pixels within the cell must be for them to be recognized by the computer's gray-scale tables. The blue-green nuclear boundaries should be set at a level that produces an image similar to that seen in the H&E slide for the specimen and reproduces the counterstain seen in the immunostained slide. The (brown) antigen boundaries should allow the creation of a brown computer mask image wherever the specified bandpass filter begins to detect it in the nucleus. Setting it too low will allow any brown background to be misidentified as nuclear antigen; setting it too high will unduly limit sensitivity, causing false negatives. The LS174T cells, as the negative controls, should show ΣOD/cell and average OD/cell pixel comparable to those of the hospital controls, using similar optical density thresholds.

Figure 5:
FIG. 5: p53$^-$ Normal Hospital Control. A computer-scanned photomicrograph of non-dysplastic colorectal tissue immunostained with the same anti-p53 antibody.
Figure 6A:
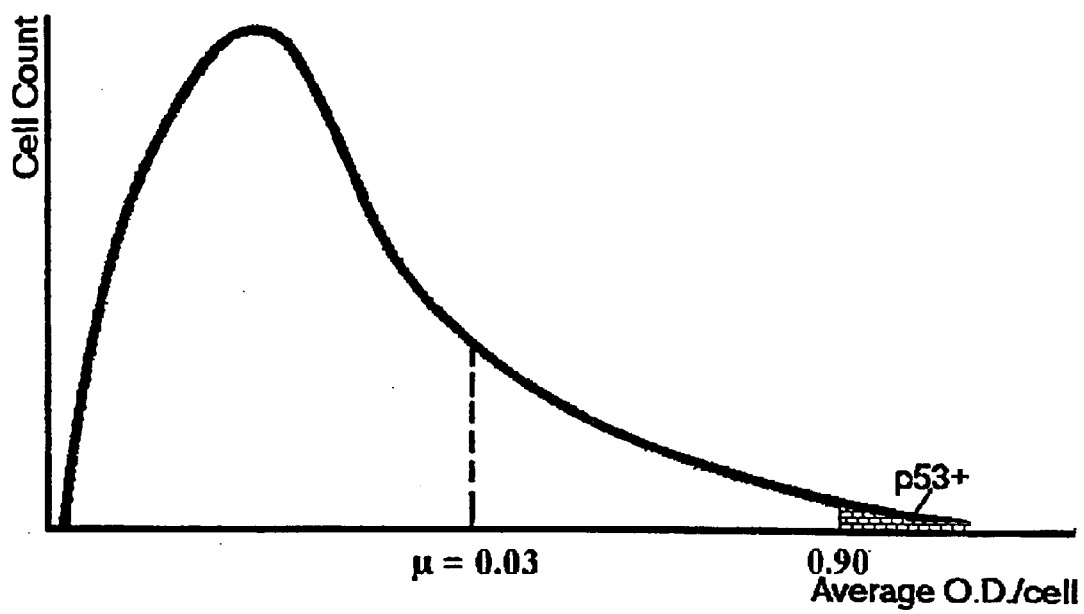
FIGS. 6a and 6b: Cell Imaging p53$^+$ Criterion. The "upper bound" of the average optical density/cell frequency distribution (FIG. 6a) and its natural log-normalized equivalent (FIG. 6b) for all sampled tissue sections from the Normal Hospital Control patients. After adjusting for the immunostaining intensity for a particular batch, this background staining cut-off value defined a "p53$^+$" cell nucleus.
Figure 6B:
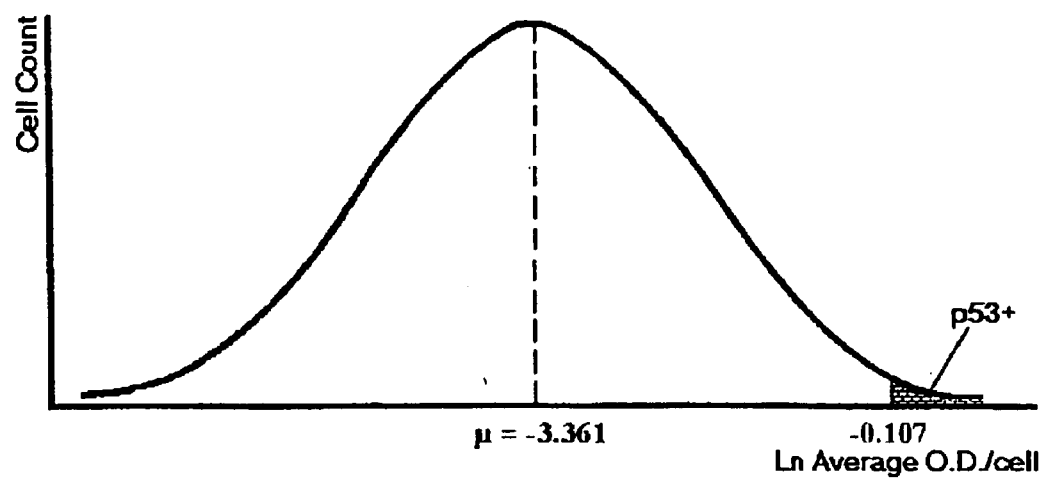

Once the non-staining normal hospital controls (FIG. 5) have been scored at the greatest allowable sensitivity, the average OD/cell distribution for the normal cells can be used to establish a rule for how dark brown a cell nucleus must be in order to be considered p53$^+$ (FIGS. 6a and 6b). (Alternatively, ΣOD/cell can be used to establish a cut-off for total staining per cell). Any patient or tumor with any target cells tissue darker than this threshold is categorized as "cell imaging p53$^+$". If control cells have been used with each immunostaining batch per the method described herein, one can adjust the definition of this threshold according to the batch's staining intensity (see below).

Once this decision is made, the operator sets the boundary definitions for the green nuclei and the brown, nuclear, accumulated p53. The antigen staining boundary should be set so that only those pixels with an intensity greater than that defined as p53$^+$ will be detected; anything else is considered artifact (noise). In theory, the threshold settings for a given staining batch should be the same for all slides and tissue classes, in practice the thresholds will have to be modified in order to accurately convey to the computer what the operator actually sees in the microscope. Given quality staining, most of the tension between best depiction of staining and unbiased threshold settings disappears. Only those areas of the image that are stained for the antigen and which are within the nuclear mask are scored; furthermore, the method is less fraught with the potential for subjectivity and positive selection bias, because it first identifies the potential at-risk cell population (counterstained crypt cell nuclei) before independently selecting representative antigen-positive cells.

The intensity of the staining per cell nucleus can by estimated by having the computer estimate the average mask OD/pixel for the cells. This is done for all the cell nuclei selected in the tissue section. The operator can estimate the total nuclear area staining per cell by computing the mask ΣOD/cell. This combines the total number of pixels/nucleus, weighted by the OD/pixel. It is the product of (intensity/pixel)×(number of pixels/nuclear area), integrated over the entire nuclear area. These two measures are the CID basis of the conversion to actual mass units of mutated p53. The average OD was used to define the p53$^+$ cutoff; it was also used to decide which areas to measure for the extent of staining. The intensity of total p53 expression/cell was measured by the ΣOD/cell.

One element of the present invention, therefore, is a data processing system for converting an image of an immunostained sample cell into a numerical output which represents the quantity of immunoreactive protein in the cell, comprising:

(a) computer processor means, such as a personal computer or workstation, for processing data;

(b) storage means, such as a hard disk, for storing data on a storage medium;

(c) image acquisition means, configured to obtain an image of the sample cell;

(c) a logic circuit configured to digitize the image;

(d) a logic circuit configured to detect the boundaries of the immunostained portions of the digitized image;

(e) a logic circuit configured to integrate the intensity of the staining over the area within the boundaries, and to provide a numerical value for the integrated intensity; and (f) a logic circuit configured to convert the obtained integrated intensity into a numerical output representing the absolute quantity of immunoreactive protein within the integrated area, by reference to a conversion factor obtained from the digitized image of an immunostained reference cell processed by components (a) through (e) of this system, the immunostained reference cells carrying a known amount of the immunoreactive protein.

7. Cell Imaging & Immunohistology Staining

Figure 7:
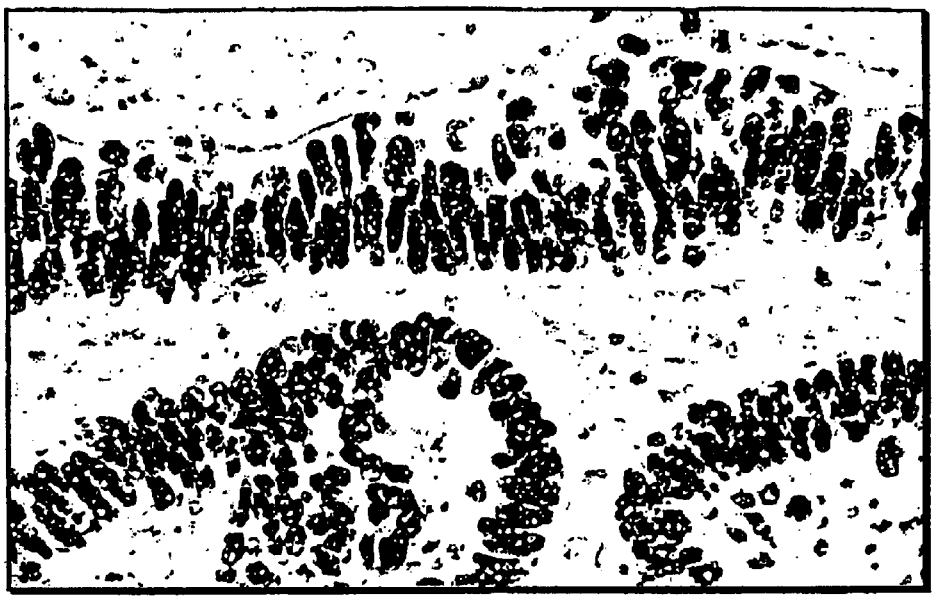
FIG. 7: p53$^+$ Adenocarcinoma within Adenoma. A computer-scanned photomicrograph of an p53$^+$ adenocarcinoma tissue section immunostained with the same anti-p53 antibody. This cancer occurred within the head of an adenomatous polyp.
Figure 8:
FIG. 8: p53$^+$ Adenocarcinoma within Adenoma. A scanned image of a photomicrograph of a paraffin section taken from the same p53$^+$ tissue block shown in FIG. 7. This image is of the hematoxylin and eosin (H&E) staining, used to identify different histologic tissue classes according to the morphology of the tissue and individual constituent cells.

FIG. 5 is a cross sectional view of a normal hospital control after p53 immunostaining. FIG. 7 is an image from a strongly positive (but typical) adenocarcinoma. This particular field shows the longitudinal orientation (profile) of the crypts. FIG. 8 shows another field of an H&E-stained section from the same adenocarcinoma. Note the similarity to the immunostained image, and the ability of such in situ images to distinguish the cancerous enterocytes from the surrounding lymphocytes and stroma, as well as any normal enterocytes (if there are any). CID enables one to clearly identity, in both the immunostained and the H&E stained cells, the tumor cell nuclei (blue), the cytoplasm (pink) and the mucin (clear). The H&E template of the different histologic areas within each section outlined upon a transparent glass coverslip allowed for segmenting the cell imaging scoring by tissue class.

8. Cell Imaging: p53 Expression per Cell

Slides were first evaluated and scored visually by the prior art immunohistochemical methods ("visual estimation"). The same slides were then blinded with respect to the visual scores, and evaluated using the CAS-200 Image Analyzer's CELL MEASUREMENT PROGRAM, (TM) Version 3.0 (CMP), at the same 400× magnification. The "Object with Mask OD" option within CMP was used. Nuclear staining was measured; each staining batch contained not only the tissue positive control and the two calibration cells, but a mixture of the different tissue classes. Thus any measurement error would be random with respect to diagnostic category, rather than creating any systematic bias.

Due to the lack of any existing diseased-based standard as to what constitutes a "sufficiently" dark and extensively immunostained cell nucleus to be considered p53$^+$, it was necessary to employ a statistical, rather than a clinical definition. The non-dysplastic colorectal hospital control specimens, shown in the IHC literature to be nearly always negative for transformed p53, were scored as a group (18 staining batches) for their Mask Average OD/cell and the frequency distribution was then log-normalized. The top 2.5% of nuclear staining intensity, i.e., a score two standard deviations above the mean ($>\mu+2\sigma$) was taken as the criterion for p53$^+$ overexpression. (FIGS. 6a and 6b). The appropriateness of this criterion—as well as the validity of using the cultured cells as calibration standards for the tissue sections—is indicated by this CID scoring threshold (0.90/cell) and the Mask Average OD/cell of the p53$^-$ LS174T colorectal cancer cells (0.53/cell) (Table 10). Given the overall range of the CID scoring of staining intensity, this shows very similar negative staining levels in the non-dysplastic patient tissue and the p53$^-$ calibration cells.

However, this threshold had to be adjusted for differences in average staining intensity among the 18 different staining batches. This adjustment for any given batch was the percentage difference of that batch's calibration cells from the grand mean of the 18 (Table 5). Any patient cells from that batch that had brown nuclei darker than this adjusted threshold were considered to contain transformed p53 and were scored for Mask Summed Optical Density/cell. The average ΣOD/cell for the 15 microscope fields sampled became the score for the tissue class of the specimen under scrutiny. This was also the criterion that triggered the tumor area scoring with the MICROMETER program.

This categorical adjustment in the p53+ criterion allows the immunopathologist to more accurately measure true biological variability by reducing the batch-effect's contribution to the experimental error. The "adjusted" scores for the p53+ A431 cells are shown in Table 5 as surrogates for typical p53+ tissue cells, in order to illustrate the considerable advantage of the method of the present invention. Use of the agarose-embedded calibration cells reduces the "batch effect", even without resorting to absolute protein quantitation (see Table 11). As is dramatically shown in Table 5, once the "adjustment coeffficient" is used, it is possible to greatly reduce the "coefficient of variation" for both Sum OD and Average OD/cell.

9. Cell Imaging: p53 Expression per Tumor

In order to find the extent of p53+ throughout the tissue samples, the MICROMETER software program (version 1.0) was employed. By first using the 620 nm wavelength, and the H&E slides, it was possible to define the "Total Tumor Mucosal Area" in the Tissue Class. Then, changing to the 500 nm filter and using the companion immunostained slides, the "p53+ Tumor Mucosal Area" in the component tissue classes was measured for each slide. Together, the two scores allow one to calculate the percentage of total tumor area that was inactivated by the p53 tumor suppressor. This same approach was used to measure the p53+ share of nuclear tumor area. The total and p53+ tumor mucosal areas were adjusted by multiplying them by their respective constants: tumor nuclear area/tumor mucosal tissue area. These figures became the basis for eventually quantifying the total p53 Body Burden in the patients. These measures eliminate the high degree of dilution of the crypt cells from stromal and connective tissue as well as regional lymphocytes, which is a problem when flow cytometry is applied immunologically to measure p53 expression in

TABLE 5

Adjustment for Batch Effect With Cell Imaging Method of Invention

| | SUM O.D./CELL | | | | AVERAGE O.D./CELL | | | |
|---|---|---|---|---|---|---|---|---|
| Batch # | LS174 CELLS | A-431 CELLS | BATCH ($\mu$) | ADJUSTED A-431 CELLS | LS174T CELLS | A-431 CELLS | BATCH ($\mu$) | ADJUSTED A-431 CELLS |
| 1 | 20.0 | 318.7 | 169.4 | 263.8 | 0.76 | 4.96 | 2.86 | 4.01 |
| 2 | 27.5 | 397.9 | 212.7 | 210.1 | 0.73 | 5.97 | 3.35 | 3.61 |
| 3 | 34.2 | 413.1 | 223.6 | 187.0 | 0.93 | 5.77 | 3.35 | 3.49 |
| 4 | 16.3 | 288.1 | 152.2 | 272.7 | 0.39 | 4.70 | 2.54 | 4.42 |
| 5 | 25.2 | 341.7 | 183.4 | 249.7 | 0.61 | 5.74 | 3.18 | 3.87 |
| 6 | 2.6 | 126.8 | 64.7 | 196.8 | 0.10 | 3.16 | 1.63 | 4.17 |
| 7 | 5.1 | 127.8 | 66.4 | 196.9 | 0.20 | 2.88 | 1.54 | 3.91 |
| 8 | 3.8 | 137.7 | 70.8 | 207.9 | 0.12 | 3.07 | 1.60 | 4.09 |
| 9 | 4.9 | 84.8 | 44.8 | 143.3 | 0.13 | 2.24 | 1.18 | 3.38 |
| 10 | 4.3 | 77.7 | 41.0 | 133.4 | 0.13 | 1.58 | 0.86 | 2.59 |
| 11 | | | | | | | | |
| 12 | | | | | | | | |
| 13 | 3.8 | 310.2 | 157.0 | 283.4 | 0.08 | 4.60 | 2.34 | 4.72 |
| 14 | 61.5 | 316.0 | 188.8 | 219.1 | 0.86 | 4.58 | 2.72 | 3.97 |
| 15 | 10.2 | 229.4 | 119.8 | 268.6 | 0.28 | 3.43 | 1.86 | 4.20 |
| 16 | 41.6 | 306.3 | 174.0 | 243.8 | 1.37 | 3.98 | 2.68 | 3.52 |
| 17 | 7.0 | 417.5 | 212.2 | 221.9 | 0.14 | 6.34 | 3.24 | 4.12 |
| 18 | 9.0 | 452.2 | 230.6 | 182.8 | 0.26 | 6.39 | 3.32 | 3.94 |
| overall average ($\mu$) | 17.3 | 271.6 | 144.5 | 217.6 | 0.49 | 4.34 | 2.40 | 3.87 |
| coefficient of variation ($\sigma/\mu$) | | 46.2% | | 20.4% | | 34.50% | | 12.70% |

Batch Effect adjustment factor: $\frac{\text{Overall}(\mu) - \text{Batch}(\mu)}{\text{Overall}(\mu)} + 1$ The CMP statistical package also provided the total number of fields and cells counted as well as the standard error. The ΣOD/cell became the basis for the later conversion of p53 optical density to p53$^{mut}$ quantitation. ΣOD/cell is a multiple of nuclear area, which is observed to get progressively larger as the tissue changed from normal to adenoma to adenocarcinoma. Assuming that the extent of the area of abnormal p53 expression is not simply a spurious effect of the larger nuclear size upon ΣOD/cell seems legitimate, since the p53− tumor cell nuclei experienced the same enlargement.

tissue lysate/cytosol. All that is needed is to use Cell Imaging Densitometry to microscopically measure the "density" of nuclei area/tumor area. [See details in "Cell Imaging Densitometry Measurements" section and Table 7, below]. Combining cell counting with the measurement of the nuclear area within Calibration Cells is also a feasible way to quantify cancer protein/cell. This was also done.

Figure 12:
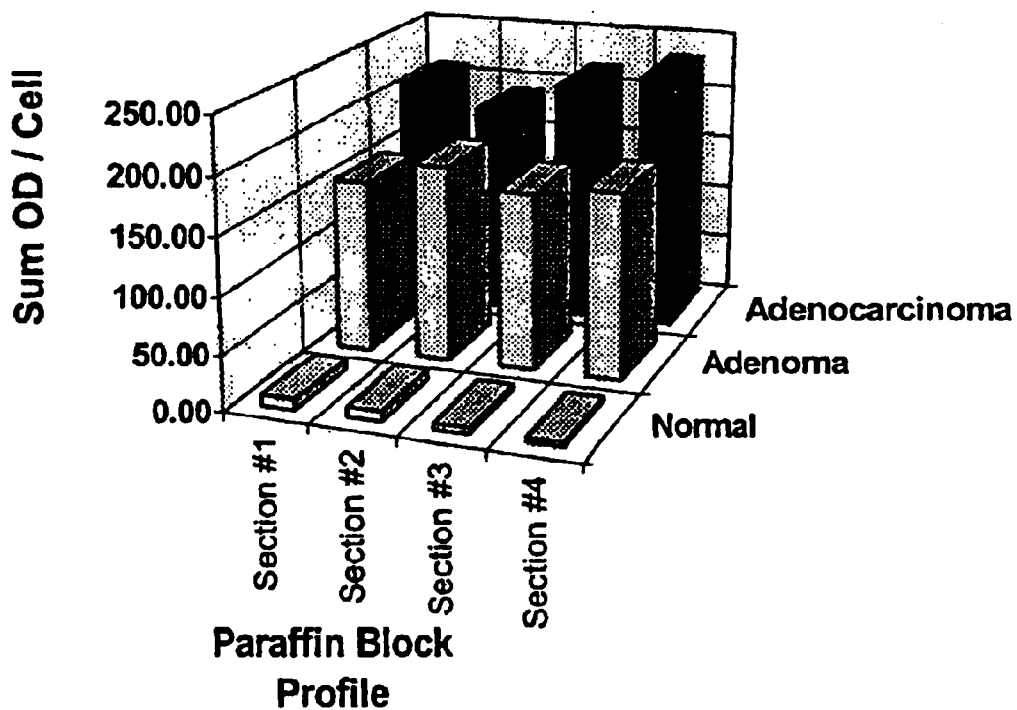
FIG. 12: Consistency of p53 Expression Throughout Tumor. The uniformity of the p53$^{mut}$ expression profile throughout the tissue block. It shows the reliability of quantifying a tumor's mutant p53 based upon measurements done on a single immunostained tissue section.

In summary, the circumstances are propitious and the method promising. We know the importance of p53$^{wt}$ in suppressing tumors, the debilitating effect that its inactivation has on cancer progression and the great frequency with which this occurs in nearly all types of solid tumors, including colorectal adenoma and adenocarcinoma. We can identify the specific cells at risk and can histologically diagnose the extent and progression of disease. Antibodies exist with which we can reliably identify and quantify the accumulation of inactivated p53 protein both in human tissue and in in vitro controls. We have evidence at the cellular level that p53$^{mut}$ has a nearly identical "dynamic range" of expression in both and that this quantity is proportional to the severity of its biological effect. The proven ability of colonoscopy to find and remove tumors and the consistency of the CID measurements throughout the depth of individual tumors (FIG. 12) suggests that the combined contribution of the colonoscope and the microscope to tissue and protein sampling error was negligible.

10. Results

The methods of this invention were applied to an examination of the relative frequencies of aberrant p53 and quantities of mutant p53 among gastroenterology patients either with (cases) or without (controls) colorectal neoplasms. Both the cases and the controls then became clinical cohorts, which were followed to see the effects of the p53 risk factor ("exposure") upon the probability and duration of survival. Previous studies indicate very high rates of exposure for this disease (50–70%) among colorectal adenocarcinoma patients and somewhat lower rates among adenoma patients (10–20%). Therefore, it was necessary to have 2–3 times more adenoma patients than cancer patients in the current study, both to find statistically significant differences in the two case groups' p53$^+$ frequency and to have sufficient numbers of adenomas and cancers to quantify their amounts of mutant p53.

Figure 9:
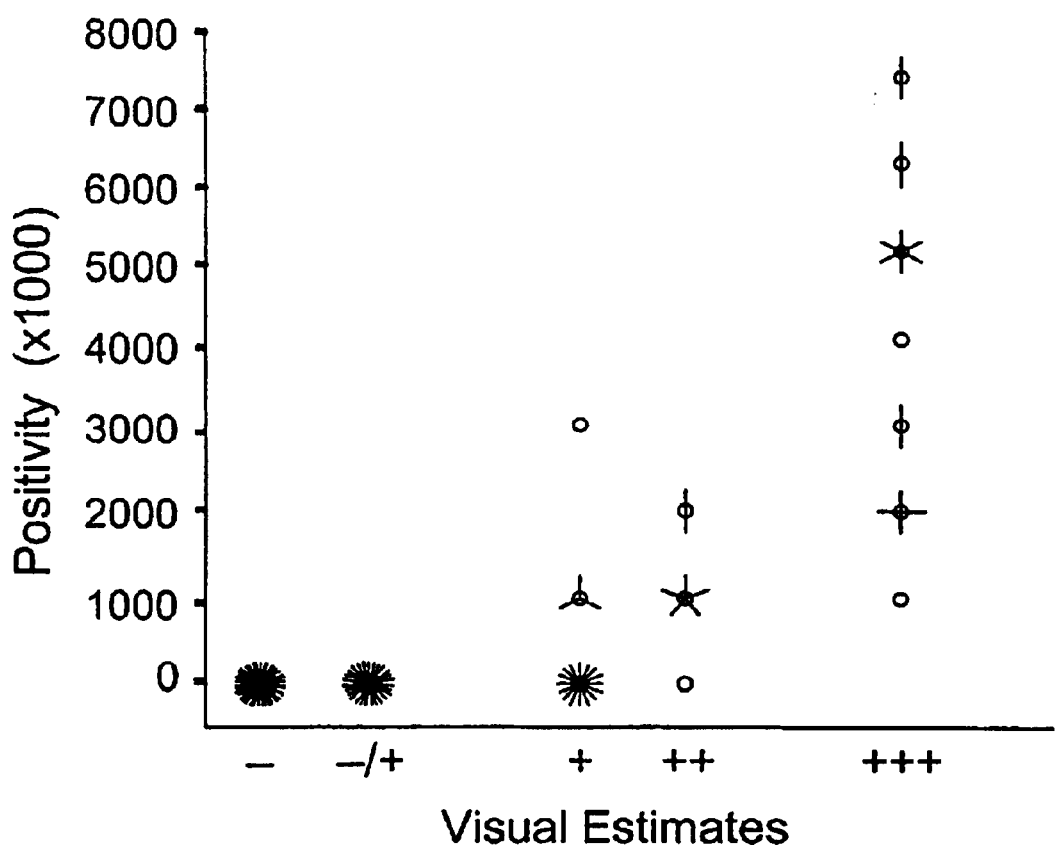
FIG. 9: Cell Imaging of Method vs. Standard IHC (Visual Estimation). A "Sunflower Plot" (one "petal" per observation) depicting the extent and intensity of immunostaining according to relative optical density scoring. It demonstrates the degree to which the prior art of subjective ordinal rankings ("visual estimation") captures the relative differences and range of p53 expression as scored by the CID method of the present invention.

FIG. 9 is a "Sunflower" plot, showing the overall distribution of the subjective ranks for all the slides (all tissue classes, all patients). The Sunflower presentation allows the number of identical (or nearly overlapping) scores to be shown in "scatterplot" format (roughly one "petal"/observation). The wide range created by the 1000× factor, while it improves graphic resolution of differences, understates the actual degree of overlap for the given staining scores. Visual estimation scores were assigned as follows:

+++=>50% of cells intensely stained

++=10–50% of cells intensely stained

–/+=1–10% of cells intensely stained

–/+=1–10% of cells moderately stained, or 10–50% lightly stained

–=0–10% of cells lightly stained, or no staining

All the high "Positivity" scores were contained within the most extreme category (+++) of Visual Estimation scores. There is good separation between the (++) and the (+++) scores. Furthermore, the (+) and (++) are moderately distinct. However, the single (+++) category loses a great deal of information, since it covers nearly an 8× range. There is tremendous overlap between the (–), (–/+), and the (+) Positivity categories in terms of the relatively wide overall distribution (although the lowest shared position has an "internal" range of 200–300). There is a single outlier within the (+) category, due, perhaps, to operator error or to the inherent subjectivity of the visual estimation.

EXAMPLES

1. Patient Selection and Diagnosis

The patients came from the Gastroenterology Departments of two New York City Medical Centers: Columbia-Presbyterian Medical Center (CPMC) and St. Luke's-Roosevelt Hospital Center (SLRHC). People with one or more colorectal adenomas and adenocarcinomas were drawn from patients who underwent colonoscopy at CPMC between October, 1990 and March, 1993. The normal hospital control subjects came from those undergoing colonoscopy at St. Luke's between July, 1997 and November, 1997. There were 115 patients from whom tissue was collected.

Patients with a prior cancer, known familial adematosis polyposis, inflammatory bowel disease, colitis, known parasites, celiac disease, Crohn's ileitis, and pouchitis were excluded. Some patients may have had a family history of colorectal cancer or sporadic adenomas. All of the cancer cases were incident and none of the subjects had prior adenocarcinomas, although some of the adenoma cases may have had previous adenomas and thus, were at greater risk of a subsequent neoplasm and possibly more likely to express inactivated p53. [112] 90% of those with an adenocarcinoma had a synchronous adenoma, although not always in the same tissue site. Some hyperplastic polyps were included in all three patient categories, in order to see if there was any "patient-effect", causing otherwise p53-hyperplastic polyps to become p53$^+$, if the patient had aberrant p53 in another tissue sample. The hospital controls had neither a current nor past colorectal cancer or adenomas, but may have had a family history of either. In addition to tissue nearly all the CPMC cases (but none of the SLRHC patients) and a separate group of CPMC colonoscopy controls donated 3 cc of blood, collected in heparinized tubes, which was spun and the resulting plasma supernatant frozen at –70° C. A subset of these samples was previously analyzed for the presence of mutant p53, using the same ELISA kits as used for the calibration cell controls, thus providing a small comparison group of cancer patients for comparing the quantity of mutant p53 in their tissue and blood.

2. The Tissue Population

Table 6 illustrates the multiple levels of observation for contrasting p53$^+$ rates by diagnostic categories, individual patients, or measurement by tumor or histologic components. Note the following with regard to the patients and their tissue samples: First, the inclusion of normal tissue controls provides a good basis for comparison with adenoma and adenocarcinoma patients; preferable to relying upon the adjacent normal tissue in the cases tumors. Second, while the total number of patients is comparable to previously cited studies, the number of cancer patients is quite small, which makes multivariate analysis among these patients all but impossible. Third, a modest number of people, particularly those with at least one adenocarcinoma, generates a large number of tumor and tissue samples. Fourth, tumors are heterogeneous in their composition by tissue classes. Thus the profile of tissue samples is adequately large and varied. The frequency distribution and the variety of histologic types together allows for examining the role of p53 loss in high- and low-risk adenomas. The coexistence of synchronous and independent adenomas among the adenocarcinoma tumors previews p53's place in the transition from pre-cancer to cancer.

TABLE 6

Patients, Tumors & Tissue
Colorectal Cancer Study Population

| Specimens | Adeno-carcinoma Cases | Adenoma Cases | Hospital Controls | Totals |
|---|---|---|---|---|
| Patient Tumors | N = 24 | N = 59 | N = 32 | N = 115 |
| Adenocarcinomas | 27 | 0 | 0 | 27 |
| Adenomatous polyps | 31 | 81 | 0 | 112 |
| Hyperplastic polyps | 11 | 7 | 4 | 22 |
| Total "tumors" | 69 | 88 | 4 | 161 |
| Slide Tissue | | | | |
| Adenocarcinomatous | 36 | 0 | 0 | 36 |
| Adenomatous | 34 | 82 | 0 | 116 |
| Hyperplastic | 11 | 8 | 3 | 22 |
| Normal | 49 | 84 | 35 | 168 |
| Total Immunostained Tissue | 130 | 174 | 38 | 342 |
| Total Immunohistology Slides | | | | 182 |
| Total Histology (H & E) Slides | | | | 182 |

There are independent sources of sampling error implicit in the tissue block selection. For any given tumor, pathologists typically use a standard tri-part sampling method of surgical excision: the two margins and a single core block. The margins serve to prove that the entire tumor was removed and are often better quality, since they are less likely to contain necrotic material than the core. They are also more likely to show the focal origin of the cancer from adjacent mucosa. Where there were multiple blocks for a single tumor, all were scored in order to be able to get as much as possible of the tumor to maximize the probability of finding p53 and to best estimate any p53$^+$ volume; necrosis was sometimes a problem.

This may also be a source of the observed variability in the percentage of p53$^+$ tumors seen in the literature. Since the aberrant p53 area is less than the total tumor (especially for adenomas), it is a more likely source of false negatives than is the undersampling of the H&E tumor area, especially given the accuracy of the colonoscope. Multiple blocks per patient were employed where possible, not to only maximize the likelihood of getting the whole tumor, but also to cover the possibility of cellular heterogeneity and tumor multi-centricity. Where an individual patient had synchronous lesions (adenomas, hyperplasia, etc.), it was possible to isolate differences in lesion types by using the patient's own cells as a control. I wanted to make sure that the tissue analyzed was representative of that which was originally diagnosed, rather than possibly being the remnants of the original paraffin block following repeated prior sectioning by others. Therefore, the tissue section I removed for immunostaining from each paraffin block lay physically between the position of the Pathology Departments' original H&E section and that of the section removed for this study's H&E staining.

Among the cases, the immuno-section sandwiched between the two H&E sections always had at least two histologic classes of tissue: normal and dysplastic (or hyperplastic). None of the normal tissue areas in any of the tissue blocks from the patient cases were positive for p53, but all were examined with the Cell Image Analyzer. Actual CID scoring was only done upon normal tissue areas from the Hospital Control patients.

H&E slides were used to create a histology template to isolate the different areas within the immuno-slide. A series of 14 different tissue classes, were defined, which were scored separately on each slide. The histologic classes so defined were as follows:

| Class 1: | Hospital control; normal |
| Class 2: | Hospital control; hyperplastic |
| Class 3: | (not applicable) |
| Class 4: | Adenoma; normal |
| Class 5: | Adenoma; hyperplastic |
| Class 6: | Adenoma, adenomatous |
| Class 7: | Adenocarcinoma; normal |
| Class 8: | Adenocarcinoma; hyperplastic |
| Class 9: | Adenocarcinoma; adenomatous |
| Class 10: | Adenocarcinoma; adenocarcinomatous |
| Class 11: | Calibration cells; LS174T (p53$^-$) |
| Class 12: | Calibration cells; A431 (p53$^+$) |
| Class 13: | Calibration tissue; resected colon (p53$^-$) |
| Class 14: | Calibration tissue; resected breast (p53$^+$) |

The purpose of this elaborate classification scheme is to demonstrate the patterns in intensity and extent of p53 inactivation in relation to the histology and clinico-pathological features of the different stages of tissue dysplasia and to prove that p53 inactivation as measured by the invention was, indeed, specific to dysplastic colorectal tissue. Such detail will not be required in routine application of the method of this invention.

For such illustrative purposes, the examples herein employ a mixture of all these categories in each staining batch, including a proportional number of adenomas, and hospital control slides. Due to scoring by the tissue class, the scoring could not be done blind to the diagnostic status of the tissue and of the patient. The balancing of different tissue classes within each batch assures that any error will be random, rather than being coincident with tissue class and reflecting measurement bias. It is advisable to re-score a previous slide to within acceptable limits (Ave. OD<10% Batch 1, factoring in batch effect adjustment) to set up the CID The p53$^+$ tissue control (ductal breast adenocarcinoma) from immunostaining batch #1 was used for this purpose.

3. Fixing and Paraffin Embedding of Cultured Cells

Cultured human tumor cells [cell lines LS174T (ATCC access No. CL-188); A431 (ATCC access No. CRL-1555); and SW480 (ATCC access No. CCL-228)] were trypsinized and pelleted upon reaching 50% confluence. After spinning five minutes at 700 rpm, the supernatant was decanted and the cells resuspended and pelleted twice with 5 mL phosphate-buffered saline containing 2% crystalline bovine serum albumin, at 4° C. Cells were counted with a hematocytometer (10 μL sample of cell suspension) to ensure that at least 10$^6$ cells were present. The cells were pelleted again, and resuspended in 1 ml of fixative at room temperature, either Bouin's (5 min.) or 10% buffered formalin (10 min.). The suspensions were pelleted for five minutes at 700 rpm, and the fixative was decanted. The cells were resuspended and pelleted four times with 2 mL phosphate-buffered saline containing 2% crystalline bovine serum albumin, at 4° C. The last pelleting was carried out in a 1.5 mL microcentrifuge tube.

A 1.5% suspension of low temperature agarose (ICN Biochemicals, Inc., Cleveland Ohio, catalog No. 800257) in phosphate-buffered saline, was brought to a momentary boil in a microwave oven, vortexed, and allowed to cool to 40° C. in a water bath. The warm agarose solution (200 μL) was added to the cell pellet in the 1.5 mL microcentrifuge tube; the cells were quickly resuspended, using a wide-bore pipette and the suspension was immediately solidified by cooling to 4° C. The agarose cell matrix was stored at room temperature prior to embedding it in paraffin.

The tube was cut open and the agarose cell matrix was removed with forceps. The matrix was placed in an empty teabag. A porous paper "biopsy bag" may also be used to achieve the proper fluid exchange and drainage, e.g., Fisher Scientific "Histoprep" bag (cat. #15-182-506H). The teabag was immersed with gentle agitation in the following series of dehydrating solvents:

70% ethanol, 10 min,
95% ethanol, 10 min (twice),
100% ethanol, 20 min(twice), and
xylene, 10 min (twice).

The agarose cell matrix was removed form the teabag and immersed in molten paraffin in a tissue block cassette holder for a few minutes. Cooling on the refrigerated surface of the paraffin embedding device solidified the paraffin.

4. Staining of Cell Samples

Sections of the paraffin block were cut at a thickness of 5 microns, floated atop the water in a 41° C. water bath, and laid upon microscope slides pre-treated with 3-aminopropyltriethoxysilane "subbing" solution. After drying overnight at 37° C. the backs of the slides were scribed with a diamond pencil to mark the location of the tissue (or agarose matrix) sample within the paraffin section.

Paraffin was removed by heating the slides to 37° C. for 30 min, followed by immersing them in xylene for three minutes (repeat 3×), 100% ethanol for five minutes (repeat 2×), and 95% (repeat 2×). If the sample was fixed with Bouin's, its picric acid content was neutralized by washing with 70% ethanol saturated with $Li_2CO_3$ for five minutes, then clearing in 70% ethanol (2×5 min). Any endogenous tissue/cell peroxidase present was quenched by soaking the sections in 0.3% hydrogen peroxide in 100% methanol for 30 minutes.

After extensive rinsing with phosphate-buffered saline (ten dips, 2×, then 2 dips and equilibrate 10 min), the slides were immersed in 300 ml of a 10 mM citrate buffer, and placed in a 1400W microwave oven. The slides and buffer were irradiated at 70% power for 20 minutes, and then allowed to cool to room temperature over 45 minutes. The slides were extensively rinsed with phosphate-buffered saline as above, and the sample section outlined with a hydrophobic slide marker (e.g., KIYOTA International, Inc., "Pap Pen"), following the previously inscribed line. Where immunostaining was contemplated, the slides were covered with a blocking solution of 10% (v/v) normal horse serum and 0.1% bovine serum albumin in phosphate-buffered saline, and incubated in a humidity chamber for one hour at room temperature.

The slides were then stained with immunohistochemical stains according to the manufacturer's instructions, followed by methyl green as a nuclear counterstain. Anti-p53 antibodies were from Oncogene Science Diagnostics (Cambridge, Mass.); biotinylated anti-mouse IgG, biotinylated peroxidase, and diaminobenzidine substrate kits were from Vector Laboratories (Burlingame, Calif.). FIG. 10 summarizes the different lab assays applied for the overall method and how they are linked.

5. Cell Imaging Densitometry Measurements

Before applying the quantification estimates to the patients and their tissue, it was necessary to measure the same slides in the traditional way in order to see whether there was any practical difference between the two methods in either the assignment of diagnostic status or the prediction of patient survival. Each batch had a planned mixture of tissue from the various tissue classes. Staining was nuclear and confined to the intestinal crypt cells.

The slides were subjectively evaluated for the relative darkness and the extent of the DAB staining of their p53, to obtain a visual estimation of ordinal ranking. The same slides were then scored according to their Optical Density (OD), using the cell measurement program of a CAS-200 Cell Image Analyzer (CID) (Becton Dickinson, Inc., Cellular Imaging Systems). Using the distributions of the OD/pixel, the computer calculated the average OD/cell nucleus for individual slides without assigning any numeric p53 calibration standards to the estimates. This was done for the entire population of normal hospital control slides (all staining batches). The average OD/cell value that was 2σ above the mean was determined, and anything darker than this intensity became the p53+ cutoff for all slides (including the controls themselves).

The same Cell Measurement Program software was used to calculate the average total p53 expression per cell. This average ΣOD/Cell is the Optical Density/pixel integrated over each cell nucleus, as defined by the CID counterstain masking filters. Total p53+ nuclear area ($mm^2$) was calculated with the densitometer's MICROMETER program. For each tissue class within each slide a "Positivity" measure was calculated. "Positivity" was defined as the average OD/cell×Total p53+ Nuclear Area ($mm^2$). "Positivity" was intended to serve as the objective, CID equivalent of "visual estimation" of staining intensity and area. "Positivity" and "visual estimation" scores for individual slides were grouped by diagnostic status (tissue class) and their concordance evaluated. This comparison suggested the degree of agreement between subjective vs. objective ordinal rank, i.e., relative quantitation. Then both Average OD/cell and ΣOD/cell scores were used to test the quality of the CID scoring (reproducibility, variability, lab artifacts, etc.); such validity was a pre-requisite for the reliability of the subsequent absolute p53 quantitation.

For mucosal tissue, being variegated in its composition, it was advantageous to employ a "gravimetric" method of area measurement. A Lovin's, Inc. field finder [a microscopic grid photolithographed onto a glass slide] was placed over the tissue microscope slide, at 40× magnification. This superimposes a 1 $mm^2$ grid upon an image of the p53+ stained tumor region(s) on the cell imaging monitor. Making the monitor co-ordinates those of graph paper comprised of 3 inch (ca. 6 mm) squares, the outline of the tumor and its p53-stained sub area was drawn on the paper and then cut out and weighed to the nearest 0.1 mg on an electronic balance. By determining the mass of the paper per unit square, the mass of the cutout was converted to area, which corresponded directly to the tumor and p53+ sample areas measured by the cell imaging densitometer. Applying the graph paper's "Area/Weight" ratio to the outline of the stained tissue samples, the total p53+ and tumor areas could be calculated quickly, simply and very accurately (Table 7). This is analogous to the way one can integrate the area in paper print outs of chromatograms.

The slides were scored batch-by-batch, using the calibration cells to correct for batch effect differences using the "batch ΣOD/cell": the combined average ΣOD/cell for p53⁺ and p53⁻ cultured cells stained along with each batch. Here, the calibration cells later used to quantify $p53^{mut}$, served as simply positive and negative lab controls. These scores, Cell Imaging p53⁺, were used to test follow-up chemotherapy response, recurrence, and patient survival status; they were also used to determine the p53⁺ percentages within different clinical and histopathology diagnostic categories. The use of the batch calibration standards makes it possible to ascribe particular amounts of mutant p53 to the individual slides' tissue classes. These amounts could be estimated in concentrations of $p53^{mut}$/total mg crypt cell protein, which is the biologically pertinent target.

present in the patient's plasma, which is expected to be useful for the minimally-invasive monitoring of cancer patients' post-surgical/adjuvant therapy progress and dosage.

Finally, by measuring the three dimensions of a sample of each positive tissue sample ($mm^3$), ($mm^2$ measurements combined with the assumption of an overall spherical shape for the p53⁺ lesion), molar units of cancer protein measurement can be estimated, that is, the molecules of mutant p53/cell. By removing the mass element from the concentration of cellular reactants, one can estimate the relative biochemical concentrations per cell of the tumor proteins and their respective ligands. For colorectal cancer this could be p53 and WAF/CIP p21 or, alternatively, the ratios of the different tumor proteins themselves, e.g., molecules mutant K-ras p21/molecules mutant p53 per cell. Some of these p53

TABLE 7

"Gravimetric" Calculation. Cell Imaging of Method of Invention
(Illustration: Tissue Block: SP92-1221/A2)

H & E 1) mucosal tumor tissue, mass of graph paper outline = 0.2564 g
2) graph paper weight/$mm^2$ = 0.00224 g $$\frac{0.2584 \text{ g}}{0.00224 \text{ g}/mm^2} = 115.357 \text{ } mm^2$$

3) $$\frac{\text{CAS-200 average}}{\text{"Tumor Nuclear Density" constant}} = \frac{0.2938 \text{ } mm^2}{mm^2 \text{ cancer tissue}}$$

$$\frac{0.2938 \text{ } mm^2 \text{ cancer nuclei}}{mm^2 \text{ cancer tissue}} \times 115.357 \text{ } mm^2 \text{ cancer tissue} = 33.89 \text{ } mm^2 \text{ cancer nuclei}$$

p53⁺

1) Mucosal tumor tissue, mass of graph paper outline = 0.2564 g
2) Graph paper weight/$mm^2$ = 0.00224 g/$mm^2$ $$\frac{0.2564 \text{ g}}{0.00224 \text{ g}/mm^2} = 114.46 \text{ } mm^2$$

3) CAS-200 average "p53⁺ Nuclear Density" constant = $\frac{0.23806 \text{ } mm^2}{mm^2 \text{ cancer tissue}}$ $$\frac{0.23806 \text{ } mm^2 \text{ cancer nuclei}}{mm^2 \text{ p53⁺ cancer tissue}} \times 114.464 \text{ } mm^2 \text{ p53⁺ cancer tissue} = 27.25 \text{ } mm^2 \text{ p53⁺ cancer nuclei}$$

This is far more specific (with respect to histologic class) and far less diluted by connective tissue, stromal material, and blood lymphocytes than such prior art examples as flow cytometry measurement of the cytosol from the whole surgically removed tissue sample. By estimating the tumor's nuclear volume, the present method makes it possible find the total mass of mutant p53 per nucleus or cell, i.e., the intracellular site in which this particular protein generally accumulates. Such mass measurements of tissue class components can then be summed for the entire tumor; where the patient had more than one tumor (or more than one sample, in the case of biopsies followed by resected specimens), and it is possible to estimate the patient's total mutant p53. This p53 measurement is termed $p53^{mut}$ "body burden". This quantity may be used to look for dose-response relations for various tumor descriptor variables such as tumor size, histology, stage, grade, etc. It can also be used to predict the corresponding steady-state concentration of mutant p53 variables were correlated with patient diagnostic status; many were applied to the results of the follow-up cohort in searching for their possible correlation with survival endpoints.

6. Analysis

The Spearman "rank (order) correlation" test was used to estimate the degree of concordance between the two ordinal-level measures: the subjective "visual estimate" and a continuous, objective "positivity" variable created solely from cell imaging measures of optical intensity and area. Simple descriptive variables, such as the proportions of different cases/controls or tissue classes that are p53⁺, were tested for categorical $\chi^2$ significance. For those analyses requiring that more stringent assumptions be met, the data were graphically plotted to demonstrate whether this was, in fact, true. Examples include the normal frequency distribution of the dependent variable (t- or z-tests and Least Squares regression). Where the more stringent assumptions could not be met, a more robust, but less powerful, test was used, e.g., Fisher-Irwin exact test, instead of $\chi^2$ for fourfold tables with sample sizes <5 in any individual cells. Non-significant results are shown (with p-values), if the pattern is suggestive, or if the lack of significance is itself important.

TABLE 8

Prior Arts "Visual Estimation"/pg p53 Correlations
Spearman's Rank-Order Correlation (rho)

|  |  | Visual Estimates | pg Mutant p53/Lesion |
|---|---|---|---|
| Correlation Coefficient | Visual Estimates | 1.000 | .777** |
|  | pg Mutant p53/Lesion | .777** | 1.000 |
| Significance (2-tailed) | Visual Estimates | . | .000 |
|  | pg Mutant p53/Lesion | .000 | . |
| N | Visual Estimates | 342 | 337 |
|  | pg Mutant p53/Lesion | 337 | 337 |

**. Correlation is significant at the .01 level (2-tailed).

TABLE 9

Prior Arts "Visual Estimation"/pg p53 Correlations
(Visual "positives" only)
Spearman's Rank-Order Correlation (rho)

|  |  | Visual Estimates | pg Mutant p53/Lesion |
|---|---|---|---|
| Correlation Coefficient | Visual Estimates | 1.000 | .900** |
|  | pg Mutant p53/Lesion | .900** | 1.000 |
| Sig. (2-tailed) | Visual Estimates | . | .000 |
|  | pg Mutant p53/Lesion | .000 | . |
| N | Visual Estimates | 72 | 69 |
|  | pg Mutant p53/Lesion | 69 | 69 |

**. Correlation is significant at the .01 level (2-tailed).

Figure 14:
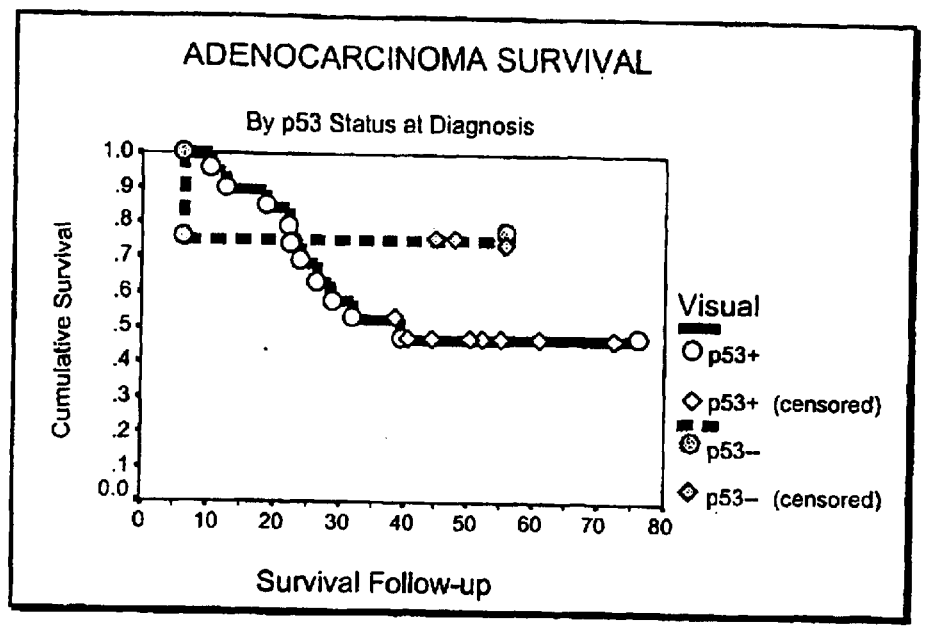
FIG. 14: Kaplan-Meier Survival Analysis done with Prior Art. The post-diagnosis survival of colorectal cancer patients whose p53$^+$ status was judged according to the visual estimation method of the prior art.
Figure 15:
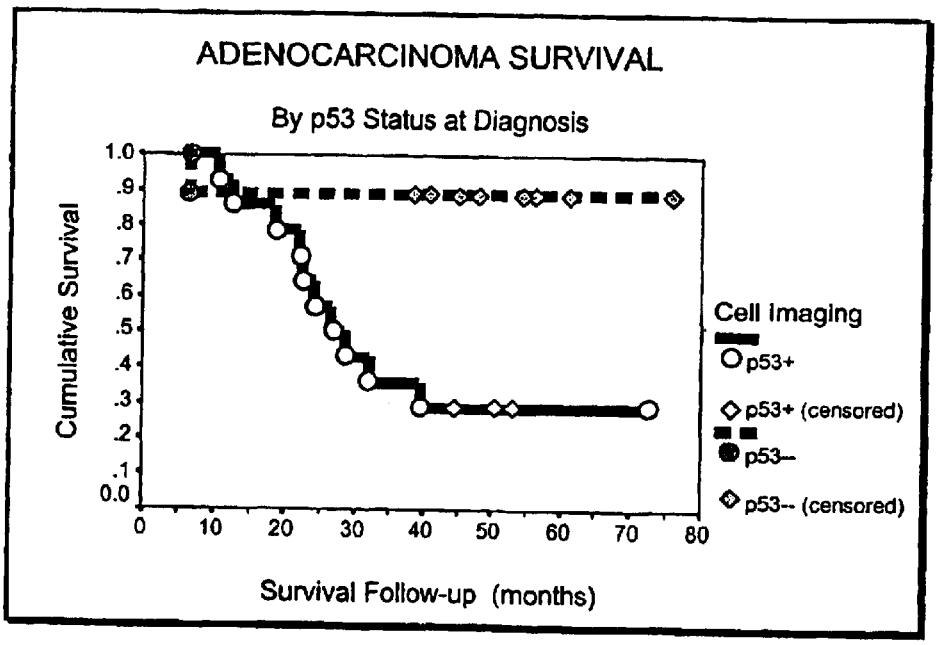
FIG. 15: Kaplan-Meier Survival Analysis done with Cell Imaging of Method. The post-diagnosis survival of colorectal cancer patients whose p53$^+$ status was judged according to the cell imaging method of the invention.
Figure 17:
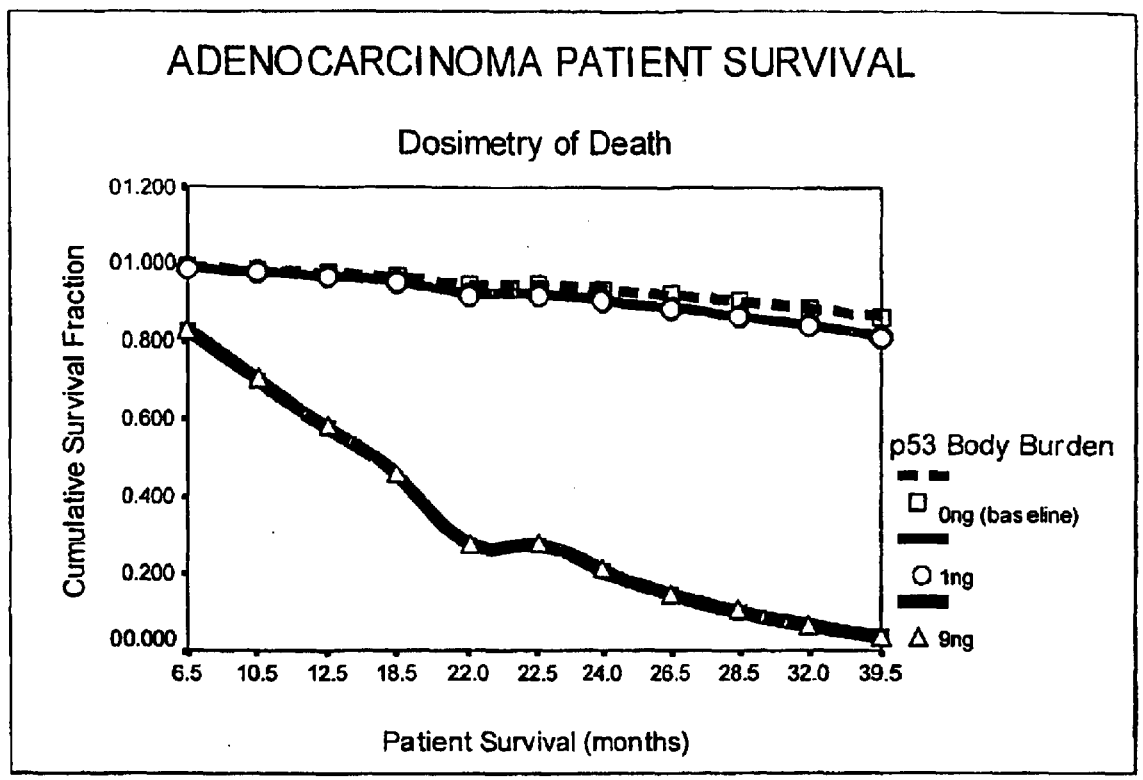
FIG. 17: Dosimetry of Death I. Quantitation of the Method of the Invention Among the p53$^+$ adenocarcinoma patients the extent to which mutant p53 has taken over their tumor burden effects survival; knowledge of this quantity in individual patients can be applied to their prognoses, thereby influencing choice of treatment.

The Spearman "rank (order) correlation" ($\rho$) results shown in Tables 8 and 9 illustrate the extent and source of the concordance between subjective "visual estimation" and the more objective ordinal rankings possible with cell imaging alone. In these two comparisons, although there was no absolute $p53^{mut}$ quantitation with calibration cells, the purely CID scoring approach did use the same biologically-based, batch-adjusted criterion for $p53^+$ (FIGS. 6a and 6b) as was used for quantitation. Thus, this "halfway step" reduces subjectivity and can dramatically improve Kaplan-Meier survival prediction (FIGS. 14–15 and Tables 19–20). However, it lacks the power to accurately correct for batch effects (Table 11), measure molecules/cell (Tables 12–13), determine protein body burden (Tables 14–15), estimate corresponding protein plasma concentrations, or utilize dose-based prediction of survival duration (Table 21 and FIG. 17). There is a strong and statistically significant correlation between the two methods. The improvement of the $\rho$ (rho) from 0.77 to 0.90 shows that much of the disagreement centers around where to set the $p53^+$ cutoff and how this can contribute to misclassification error for the (+/−) tissue. Some of this is due to background staining and some from the vagaries of the batch effect, which visual estimation cannot resolve, even with the inclusion of qualitative lab controls.

7. Mutant p53 Quantitation

The calibration cells are intended to simply and accurately provide reproducible immunostaining standard curves. Due to the common phenotype traits shared by the various mutations, they can also give some indication of the degree of loss of the p53 tumor suppressor function. Previous attempts to use cultured cells and cell imaging for protein quantitation have used retroviral expression vectors in the HER-2/neu oncogene in order to engineer specific levels of that cancer protein in the control cells.[6] This could allow for a greater number of standards with which to construct the standard curves, but engineered cells may not be representative of p53-dependent tumor cells. Others have attempted to use nuclear DNA staining for calibration (U.S. Pat. No. 5,252,487, which is incorporated herein by relevance).

The matrix-embedded calibration cells of the present invention share many similarities with the colorectal cells having inactivated p53. They are live cells, with (dys) functioning p53, interacting with other human cell constituents. This provides the opportunity for post-translational processing, phosphorylation, more than one type of mutation, interference from other cellular proteins (such as the HSP70), etc. Their cellular behavior is likely to also be similar, e.g. nuclear localization of the aberrant p53, steady-state levels of the protein. Since immunohistology can be used to measure any p53 inactivation, rather than mutation per se, this approach can be used in a wide variety of solid tumors, including those whose p53 tumor suppressor dysfunction is caused by other sources of damage, e.g., Human Papilloma Virus (HPV16/18) in the cervix. These controls also share a similarity in the context in which the antibodies recognize the p53 antigen because the in vitro control cells also experience the same potential barriers to antibody recognition and quantitation created from sample processing and preservation, such as, fixation, heat, de-hydration, paraffin embedding, and microtome cutting. Finally, for both the controls and the samples p53 over-expression is an index of p53 gene inactivation.

Table 4, above, suggested not only that the detection of aberrant p53 was both sensitive and specific, but that the in vitro cells are valid proxy for the in vivo inactivation of the p53 tumor suppressor protein. First, because the signal/noise ratios for the cultured cells were nearly identical to that of the tissue cells, they are a valid substitute. Secondly, the ratio of the $p53^+$ and $p53^-$ total immunostaining ($\Sigma$OD/Cell) in both the calibration cells and the dysplastic enterocytes is almost exactly equal to the ratio of the half-lives of the inactive and active forms of the protein (~22); given the biological consequences of p53 transformation described above, this suggests that the relative amount of p53/cell measures—and is proportional to—its biological effect. If this is true for the tumor as a whole, the patient's total amount of abnormal/mutant p53 may, indeed, predict the duration of post-surgical survival (Table 21 and FIG. 17).

8. Determination of ng Mutant p53/mg Protein

Two batches each (batches A and B) of the cultured calibration cells were lysed and the lysates were assayed according to the published protocols provided with the commercial p53 ELISA kits. Conversion to mass concentrations of mutant p53 was done by applying the average volumetric concentration of the duplicate wells for the 3× and 10× dilutions of the three cell lysates. These ng p53/mL concentrations for Batch A and B were converted to ng p53/mg protein by dividing by the mg/mL lysate protein concentrations in the different tissue cultures for their respective batches. The two values for each batch were themselves averaged to arrive at the most stable estimate of the expression of p53$^{mut}$ per mass of total protein. For the LS174T and SW480 cell lines this was the mass of the protein present in the enterocytes of the intestinal crypts themselves. These mass concentrations could then be compared with the ΣOD/Cell cell imaging densitometry measurements for the three calibrations. Table 10 summarizes and combines the ELISA and immunostaining data for the three cell lines, using the average ELISA values for batches A and B. The mass concentrations in bold were those used to derive the Calibration Curve.

TABLE 10 p53 Levels in Immunohistology Calibration Standards of Invention

| Cell Line | Immunostaining | | Mutant ELISA | |
|---|---|---|---|---|
|  | ΣOD cell | Avg. OD cell | ng p53/ml* | ng p53/mg |
| LS 174T | 17 | 0.53 | 1.40 | 0.13 |
| A-431 | 285 | 5.54 | 68.4 | 6.92 |
| SW 480 | 413 | 6.63 | 126 | 7.94 |

*adjusted upward to account for the 10x dilution in lysing buffer.

Figure 11:
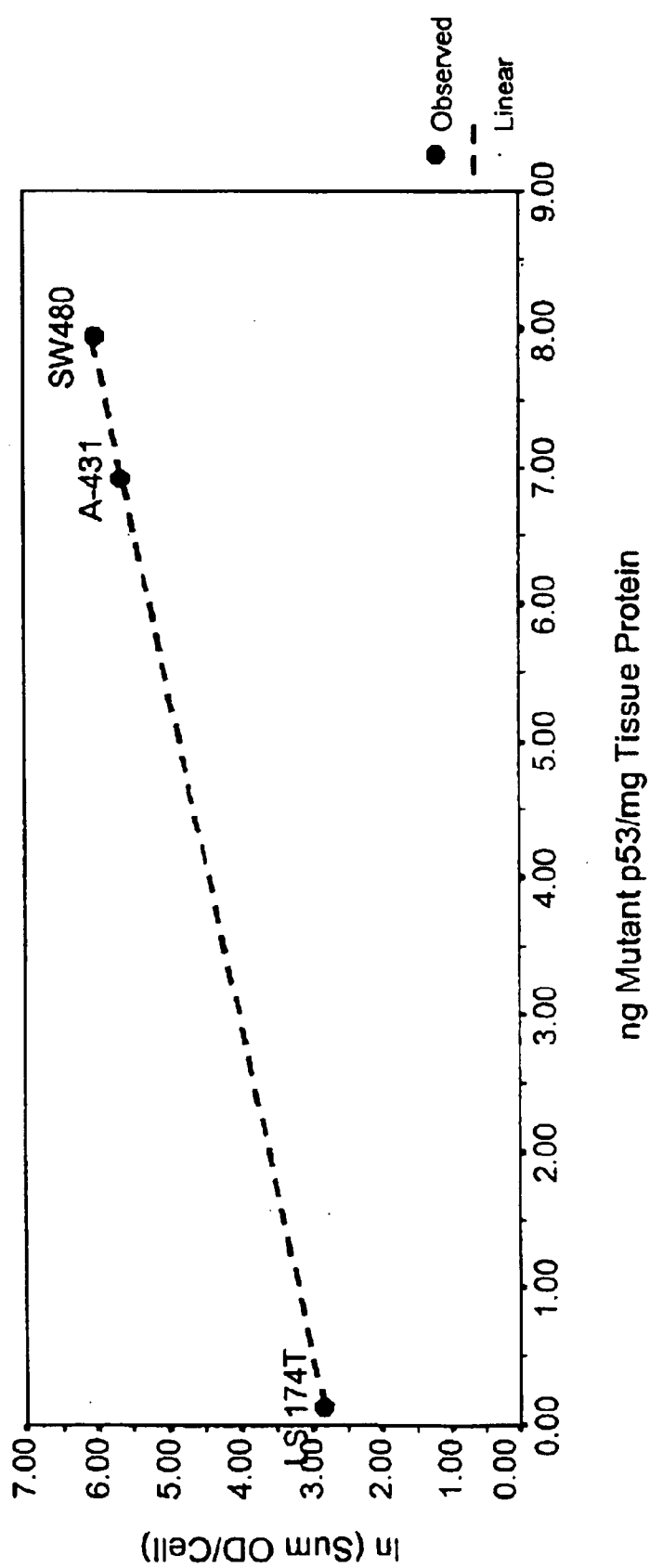
FIG. 11: Immunohistology p53$^{mut}$ Calibration Curve. The overall immunostaining "standard curve" defining the statistically-derived continuous quantitative function between Cell Imaging Densitometry and p53$^{mut}$ protein concentration in human tissue.

A glance at the two columns of bold figures in Table 10 makes it obvious that there is no direct proportionality between the two variables. The distribution of staining intensity for individual slides and for tissue classes as a whole (Average OD/cell) was quite normally distributed, but their nuclear size and ΣOD/cell were positively skewed to the right (tail to the right, mean>median; see FIG. 6a). This reflects the effect of a few very large cells combined with the inability to distinguish and segregate overlapping nuclei among contiguous cells and illustrates the appropriateness of normalizing the ΣOD/Cell distributions within a tissue section by employing the natural log ($\log_e$) normalized raw scores (see FIG. 6b). This proved very effective in producing a linear regression between the three paired data points in the table, capable of being applied to the paraffin tissue sections themselves in order to translate the darkness and extent of immunostaining per cell into the absolute mass of mutant p53 per cell, mass or volume. The "least squares" best estimate of the linear relation for ln(ΣOD) regressed upon ng mutant p53/mg protein is linear, and 100% of the linear shape of the regression line is accounted for by the co-variation between the quantity of mutant p53 in the calibration cells and their associated immunostaining (FIG. 11: $R^2$=1.00, p-value=0.009)

TABLE 11

Correction of "Batch Effect" with Quantitation Method of Invention

MUTANT p53 QUANTITATION (Batch Adjusted)

| IMMUNOHISTOLOGY BATCH | CALIBRATION CELLS | | | | |
|---|---|---|---|---|---|
|  | ng p53$^{mut}$/mg protein | | ln (Sum O.D./Cell) | | IMMUNOSTAINING |
| (#) | p53$^-$ | p53$^+$ | p53$^-$ | p53$^+$ | CALIBRATION CURVE |
| 1 | 0.13 | 6.92 | 2.99 | 5.76 | Y = 2.937 + (0.408)x |
| 2 | 0.13 | 6.92 | 3.31 | 5.99 | Y = 3.259 + (0.395)x |
| 3 | 0.13 | 6.92 | 3.53 | 6.02 | Y = 3.482 + (0.367)x |
| 4 | 0.13 | 6.92 | 2.79 | 5.66 | Y = 2.735 + (0.423)x |
| 5 | 0.13 | 6.92 | 3.23 | 5.83 | Y = 3.18 + (0.383)x |
| 6 | 0.13 | 6.92 | 0.95 | 4.84 | Y = 0.876 + (0.573)x |
| 7 | 0.13 | 6.92 | 1.63 | 4.85 | Y = 1.568 + (0.474)x |
| 8 | 0.13 | 6.92 | 1.33 | 4.92 | Y = 1.261 + (0.529)x |
| 9 | 0.13 | 6.92 | 1.59 | 4.44 | Y = 1.535 + (0.420)x |
| 10 | 0.13 | 6.92 | 1.46 | 4.35 | Y = 1.405 + (0.426)x |
| 11 | NA | NA | NA | NA | NA |
| 12 | NA | NA | NA | NA | NA |
| 13 | 0.13 | 6.92 | 1.33 | 5.73 | Y = 1.246 + (0.648)x |
| 14 | 0.13 | 6.92 | 4.12 | 5.75 | Y = 4.089 + (0.240)x |
| 15 | 0.13 | 6.92 | 2.32 | 5.43 | Y = 2.26 + (0.458)x |
| 16 | 0.13 | 6.92 | 3.73 | 5.72 | Y = 3.692 + (0.293)x |
| 17 | 0.13 | 6.92 | 1.94 | 6.03 | Y = 1.862 + (0.602)x |
| 18 | 0.13 | 6.92 | 2.20 | 6.11 | Y = 2.125 + (0.576)x |

'Y' = ln(Sum O.D./Cell)
'x' = ng p53$^{mut}$/mg protein

Steps:
1) Transform all the ΣO.D./cell scores en masse for each slide in a given batch to their Natural Log (ln).
2) Apply the Immunostaining Calibration Curve to each slide in that batch, solving for 'x'.

Table 11, above, displays two continuous, interval-level measures of the intensity of cellular mutant p53 expression per cell: $\Sigma$OD/cell and ng mutant p53/mg crypt cell protein. The natural log of the combined darkness and total nuclear area of the brown stain is directly proportional to the quantity of mutated p53 among those cells targeted by this type of cancer. There is a specified range of expression for which we have a linear rule of the form $Y = \alpha + \beta x$, where $Y = \ln(\Sigma OD/cell)$, $\alpha$=normal p53 background staining, and $\beta$=the rate of increase in Y per unit increase in the concentration (ng/mg) of mutant p53 in the tissue. The existence of this relationship means that despite the use of different protocols and antibodies, data from different investigators can, for the first time, be combined or compared. Even within a single lab, these same calibration cells can be used as quantitative controls on day-to-day differences in staining intensity. Table 11 shows how, by including these IHC controls in each staining batch, one can adjust measured protein levels for "batch effects" so that IHC measures of absolute quantities of a given protein gathered over time for many patients in a single clinical study can also be reliably combined.

9. Determination of p53$^{mut}$ Molecules/Cell

The immunohistology regression line for the particular batch of slides was used to convert the cell imaging score into p53 concentration per mg protein, and to change this to a volumetric concentration, using the SW480 cell lysate concentration as a constant. The tissue sample's average crypt cell volume ($\mu$m$^3$/cell) was estimated and used to calculate the number of p53$^{mut}$ molecules/cell.

The estimation of the average cell volume was done with the CAS-200 MICROMETER software program, using the H&E slide for the p53$^+$ regions in question, as determined from its immunostained "partner slide" and the H&E tissue class template. The target cells for colorectal adenomas and adenocarcinomas are the epithelial enterocytes of the large intestine. The size of these enterocytes can vary substantially by histologic status: normal, hyperplastic, adenomatous, adenocarcinomatous. The "spherical" diameters were defined as the average of the two cross-sectional cell diameters. The formula used for the volume of the columnar normal, hyperplastic, and adenomatous cells was that of a cylinder, while for the well-differentiated cancerous p53$^+$ cells the formula for volume of a prolate spheroid: $(4/3)\pi a^2 b$, was employed, where "a"=long radius and "b"=short radius. For moderately and poorly differentiated cancer cells the formula for the sphere was used. The volumetric measurement of prolate spheroid tumor cells in semi-solid medium has been reported previously.[113]

TABLE 12

Calculation of "Molar" Concentration of Cancer Protein per Cell with Quantitation Method of Invention

Molecules p53$^{mut}$/Crypt Cell

Procedure

A. Determine ng mutant p53/crypt cell.

1. Convert $\Sigma$O.D./cell nucleus to ng mutant p53/mg cell lysate, using the calibration curve for the staining batch.
2. Convert from a mass (ng/mg) to a volumetric (ng/ml) concentration for total protein, using the measured concentration of the p53$^+$ colorectal cultured cell lysates (SW480).
3. Convert to common measurement units (ng/ml to ng/$\mu$m$^3$).
4. Multiply by the sample's estimated average crypt cell volume ($\mu$m$^3$).

B. Calculate # molecules mutant p53/crypt cell.

1. Convert mass units (ng/$\mu$m to g/$\mu$m).
2. Convert p53 to its mole-gram equivalent.
3. Multiply by # p53 cells/mole.

Example: Cancer Cells (slide #41)

A. ng mutant p53/crypt cell.

$$\sum OD/cell = 207.8 \xrightarrow{\text{(quantitation of method)}} \frac{4.74 \text{ ng p53}}{\text{mg cancer cell lysate}}$$

$$\left[\frac{4.74 \text{ ng p53}}{\text{cancer cell lysate}}\right]\left[\frac{16.4 \text{ cancer cell lysate}}{\text{ml cancer cell lysate}}\right] = \frac{77.70 \text{ ng p53}}{\text{ml cancer cell lysate}}$$

$$\left[\frac{77.7 \text{ ng p53}}{\text{cancer cell lysate}}\right][1 \times 10^{-12}]\left[\frac{1561}{\text{cancer cell}}\right] = \frac{1.213 \times 10^{-7} \text{ ng p53}}{\text{cancer cell}}$$

B. # molecules mutant p53/crypt cell $$\left[\frac{1.213 \text{ ng} \times 10^{-7} \text{p53}}{\text{cancer cell}}\right]\left[\frac{1}{1 \times 10^9}\right][5.3 \times 10^4][6.022 \times 10^{23} \text{ molecules}] = \frac{1378 \text{ molec's p53}}{\text{cancer cell}}$$

more simply, converting all conversion factors to a constant: (k) = $1.136 \times 10^{-2}$, $$\left[\frac{77.7 \text{ ng p53}}{\text{ml cancer cell lysate}}\right]\left[\frac{1561 \ \mu m^3}{\text{cancer cell}}\right][1.136 \times 10^{-2}] = \frac{1378 \text{ molecules p53}^{mut}}{\text{cancer cell}}$$

TABLE 13

Molar Measure of Protein/Cell from Quantitation of Method

MUTANT p53 MOLECULES PER CELL

| SLIDE # | TISSUE CLASS | ng p53 mg crypt protein | ng p53 mL crypt tissue | Cell Volume ($\mu m^3$/cell) | Conversion Constant (k) | #p53 Molecules crypt cell |
|---|---|---|---|---|---|---|
| 41 | 10 | 4.74 | 77.70 | 1561 | $1.136 \times 10^{-2}$ | 1378 |
| 107 | 10 | 5.49 | 90.04 | 6810 | $1.136 \times 10^{-2}$ | 6962 |
| 371 | 10 | 5.42 | 88.88 | 1079 | $1.136 \times 10^{-2}$ | 1089 |
| 377 | 5 | 0.8 | 13.12 | 404 | $1.136 \times 10^{-2}$ | 60 |
| 17 | 10 | 5.58 | 91.51 | 4612 | $1.136 \times 10^{-2}$ | 4794 |
| 23 | 10 | 4.77 | 78.23 | 1694 | $1.136 \times 10^{-2}$ | 1505 |
| 29 | 10 | 3.47 | 56.91 | 1527 | $1.136 \times 10^{-2}$ | 987 |
| 53 | 10 | 6.59 | 108.08 | 3302 | $1.136 \times 10^{-2}$ | 4054 |
| 67 | 10 | 0.42 | 6.89 | 2326 | $1.136 \times 10^{-2}$ | 182 |
| 59 | 10 | 6.38 | 104.63 | 3083 | $1.136 \times 10^{-2}$ | 3664 |
| 259 | 6 | 4.86 | 79.70 | 2854 | $1.136 \times 10^{-2}$ | 2584 |
| 269 | 9 | 6.18 | 101.35 | 595 | $1.136 \times 10^{-2}$ | 685 |
| 269 | 10 | 6.06 | 99.38 | 4835 | $1.136 \times 10^{-2}$ | 5458 |
| 251 | 6 | 4.59 | 75.28 | 1278 | $1.136 \times 10^{-2}$ | 1093 |
| 253 | 10 | 3.43 | 56.25 | 2144 | $1.136 \times 10^{-2}$ | 1370 |
| 196 | 10 | 7.98 | 130.87 | 2845 | $1.136 \times 10^{-2}$ | 4230 |
| 209 | 10 | 6.58 | 107.91 | 1047 | $1.136 \times 10^{-2}$ | 1283 |
| 226 | 10 | 5.57 | 91.35 | 1799 | $1.136 \times 10^{-2}$ | 1867 |
| 364 | 9 | 7.69 | 126.12 | 3405 | $1.136 \times 10^{-2}$ | 4878 |
| 364 | 10 | 7.13 | 116.93 | 4358 | $1.136 \times 10^{-2}$ | 5788 |
| 357 | 10 | 7.14 | 117.10 | 1326 | $1.136 \times 10^{-2}$ | 1763 |
| 308 | 10 | 4.38 | 71.83 | 1834 | $1.136 \times 10^{-2}$ | 1497 |
| 323 | 10 | 6.48 | 106.27 | 2254 | $1.136 \times 10^{-2}$ | 2721 |
| 317 | 10 | 2.74 | 44.94 | 1121 | $1.136 \times 10^{-2}$ | 572 |
| 161 | 10 | 3.65 | 59.86 | 341 | $1.136 \times 10^{-2}$ | 232 |
| 124 | 10 | 7.22 | 118.41 | 921 | $1.136 \times 10^{-2}$ | 1240 |
| 215 | 10 | −1.92 | −4.09 | **** | $1.136 \times 10^{-2}$ | **** |
| 413 | 6 | 5.78 | 94.79 | 276 | $1.136 \times 10^{-2}$ | 298 |
| 569 | 6 | 4.86 | 79.70 | 320 | $1.136 \times 10^{-2}$ | 290 |
| 515 | 6 | 2.46 | 40.34 | 342 | $1.136 \times 10^{-2}$ | 156 |
| 523 | 6 | 3.36 | 55.10 | 308 | $1.136 \times 10^{-2}$ | 192 |
| 461 | 6 | 4.79 | 78.56 | 548 | $1.136 \times 10^{-2}$ | 489 |
| 755 | 6 | 4.68 | 76.75 | 450 | $1.136 \times 10^{-2}$ | 392 |
| 959 | 6 | 5.69 | 93.32 | 577 | $1.136 \times 10^{-2}$ | 612 |
| 635 | 6 | −0.93 | −1.53 | **** | $1.136 \times 10^{-2}$ | **** |
| 761 | 6 | −1.05 | −1.56 | **** | $1.136 \times 10^{-2}$ | **** |
| 887 | 6 | −0.89 | −1.35 | **** | $1.136 \times 10^{-2}$ | **** |
| 983 | 6 | 2.73 | 44.77 | 716 | $1.136 \times 10^{-2}$ | 364 |
| 821 | 6 | 3.42 | 56.09 | 970 | $1.136 \times 10^{-2}$ | 618 |
| 857 | 6 | 3.81 | 62.48 | 480 | $1.136 \times 10^{-2}$ | 341 |
| 863 | 6 | 4.12 | 67.57 | 568 | $1.136 \times 10^{-2}$ | 436 |
| 824 | 6 | 2.84 | 46.57 | 272 | $1.136 \times 10^{-2}$ | 144 |
| 908 | 6 | 2.71 | 44.44 | 297 | $1.136 \times 10^{-2}$ | 150 |
| 1186 | 1 | 3.91 | 64.12 | 346 | $1.136 \times 10^{-2}$ | 252 |

Table 12 shows the required steps, illustrated for a particular patient with a Stage D colorectal adenocarcinoma lesion. For those cell types for which their volume, once becoming dysplastic, is already known, the laborious procedure of measuring the dimensions of individual cells (step A4), would be unnecessary. Table 13 lists the components and the final estimates of p53 molecules/cell for the study patients estimated from the procedure in Table 12.

10. Determination of p53 Body Burden

This calculation requires two assumptions. The first is that the shape of the locus of mutant p53 is spherical. Aberrant p53 usually arises within a clonal, contiguous focus, then expands in a somewhat concentric fashion in the expanding core of the hypoxic tissue environment. From the total p53+ nuclear area, one can solve for the radius and then for the spherical volume (mm$^3$) of p53$^{mut}$ expression.

Given the concentration of crypt cell protein in mg/mL and the concentration of p53$^{mut}$/mg crypt protein, it was possible to determine the total mass of p53. This required the second assumption: that the total protein concentration of the SW480 cell lysate is the same as that of the colorectal crypt tissue protein. The high concentration of p53$^{mut}$ in the SW480 lysate is a very small fraction of the total protein, and since this is a colorectal adenocarcinoma cell line comprised solely of crypt tissue in which p53$^{mut}$ is expressed, this assumption is reasonable. The SW480 total protein concentration was determined, using a bicinchoninic acid assay, to be 16.4 mg protein/mL cancer cell lysate. Once the pg p53 per tumor was known, the total body burden per patient was obtained by summing across $\geq 1$ tumor/patient. The calculations shown in the example in Table 14, when applied to the patient samples, provided the results summarized in Table 15.

TABLE 14

Total Protein/Patient Calculation using Method of Invention $$\text{p53}^{mut}\text{ Body Burden}$$

Example: Slide # 41

$$\sum OD/cell = 207.8 \xrightarrow[\text{(quantitation of method)}]{} \frac{4.74 \text{ ng p53}^{mut}}{\text{mg crypt protein}} \therefore$$

$$\left[\frac{4.74 \text{ ng p53}^{mut}}{\text{crypt protein}}\right]\left[\frac{16.4 \text{ crypt protein}}{\text{ml SW480 lysate}}\right] = \frac{77.70 \text{ ng p53}}{\text{ml SW480 } lysate} \therefore$$

$$[1000 \text{ pg}][77.70 \text{ p53}^{mut}][1000]\left[\frac{10.976 \text{ p53}^{+} \text{ cell volume}}{}\right] = 853 \text{ pg p53}^{mut}$$

TABLE 15

Cancer Protein per Patient with Quantitation of Method
$\text{p53}^{mutant}$ BODY BURDEN

| PATIENT (#) | SLIDE (#) | TISSUE CLASS | ng p53$^{mutant}$ mL Crypt Cells* | p53$^{mut}$ (mm³) | pg p53$^{mutant}$ LESION | pg p53$^{mutant}$ PATIENT |
|---|---|---|---|---|---|---|
| 3597904 | 41 | 10 | 77.7 | 10.976 | 852.64 | 852.84 |
| 2456467 | 107 | 10 | 90.1 | 106.767 | 9619.69 | 9619.69 |
| 3470038 | 371 | 10 | 88.8 | 1.986 | 176.36 | |
| 3470038 | 377 | 5 | 13.0 | 0.0001 | 0.001 | 176.361 |
| 3649373 | 17 | 10 | 91.6 | 0.183 | 16.76 | |
| 3649373 | 23 | 10 | 78.2 | 21.369 | 1671.06 | |
| 3649373 | 29 | 10 | 56.9 | 3.968 | 225.78 | 1896.84 |
| 3580993 | 53 | 10 | 108.0 | 11.306 | 1221.05 | |
| 3580993 | 67 | 10 | 4.9 | 1.246 | 6.10 | |
| 3580993 | 59 | 10 | 104.6 | 0.048 | 5.02 | 2454.30 |
| 2431987 | 259 | 6 | 79.7 | 0.697 | 55.52 | |
| 2431987 | 269 | 9 | 101.4 | 3.540 | 358.96 | |
| 2431987 | 269 | 10 | 99.3 | 95.630 | 9496.06 | 9910.54 |
| 3562267 | 251 | 6 | 75.3 | 1.786 | 134.48 | |
| 3562267 | 253 | 10 | 56.2 | 0.002 | 0.11 | 134.59 |
| 1554609 | 196 | 10 | 130.9 | 73.222 | 9584.76 | |
| 1554609 | 209 | 10 | 107.2 | 0.039 | 4.18 | 9584.76 |
| 3608611 | 226 | 10 | 91.4 | 0.508 | 46.43 | 46.43 |
| 1361081 | 364 | 9 | 126.1 | 0.450 | 56.76 | |
| 1361081 | 364 | 10 | 117.0 | 27.050 | 3164.85 | |
| 1361081 | 357 | 10 | 117.1 | 23.720 | 2777.61 | 5999.22 |
| 2607629 | 308 | 10 | 71.9 | 0.094 | 6.76 | 6.76 |
| 3532810 | 323 | 10 | 106.3 | 35.670 | 3791.45 | |
| 3532810 | 317 | 10 | 44.9 | 7.740 | 347.46 | 4138.91 |
| 3618007 | 161 | 10 | 59.9 | 0.00004 | 0.002 | 0.002 |
| 1374180 | 124 | 10 | 118.5 | 2.033 | 240.91 | 240.91 |
| 3413015 | 215 | 10 | −40.9 | 0.002 | — | — |
| 1896987 | 413 | 6 | 94.9 | 0.048 | 4.56 | 4.56 |
| 1632303 | 569 | 6 | 79.7 | 2.867 | 228.50 | 228.50 |
| 3637467 | 515 | 6 | 40.3 | 0.315 | 12.69 | 12.69 |
| 3223764 | 523 | 6 | 55.0 | 0.062 | 3.41 | 3.41 |
| 3573811 | 461 | 6 | 78.5 | 0.015 | 1.18 | 1.18 |
| 2473033 | 755 | 6 | 76.7 | 0.027 | 2.07 | 2.07 |
| 3421598 | 959 | 6 | 93.3 | 0.280 | 26.12 | 26.12 |
| 1392444 | 635 | 6 | −15.3 | 0.002 | — | — |
| 2269781 | 761 | 6 | −15.6 | 0.001 | — | — |
| 2221349 | 887 | 6 | −13.5 | 0.006 | — | — |
| 3087524 | 983 | 6 | 44.8 | 0.006 | 0.29 | 0.29 |
| 1880402 | 821 | 6 | 56.1 | 0.0006 | 0.03 | 0.03 |
| 3525504 | 857 | 6 | 62.5 | 0.0005 | 0.03 | |
| 3525504 | 863 | 6 | 67.5 | 0.0001 | 0.007 | 0.037 |
| 3462180 | 824 | 6 | 46.7 | 0.003 | 0.13 | 0.13 |
| 3303782 | 908 | 6 | 44.4 | 0.0003 | 0.01 | 0.01 |
| 4088232 | 1186 | 1 | 64.1 | 0.003 | 0.19 | 0.19 |

*adjusted for 10x dilution of cultured cells in lysing buffer 11. p53$^{mut}$ Blood Concentration. A Surrogate Measure for Tissue Body Burden The Background of the Invention, Section 3: "Previous Methods for Quantitation of p53 Protein", illustrated that the range of p53 expression for both tumor tissue and in sera or plasma is known. It also showed that there is some agreement in individual tumor patient's between the expression of transformed p53 in their tissue and blood and that these levels correspond to their concurrent—or possibly future (in the case of asbestosis-induced lung cancer), clinical diagnosis. The SW480 cell supernatant was used to predict the amount of p53$^{mut}$ entering the blood stream from tumor tissue. Expression of p53$^{mut}$ in the SW480 calibration cells, supernatant was measured to see if the same mutant p53 ELISA used for quantifying p53 in tissue sections and in patients' blood could reliably detect different concentrations of p53 leached into their surrounding medium. Supernatant was collected three days after the last cell feeding, to simulate the steady-state status of p53 in the body. Dilution recovery analysis was performed upon three different concentrations (two dilutions) and demonstrated that the observed and εξπεχτεδ p53 concentrations were equal ($R^2$= 0.987, p=0.07, β=1.01). The evidence marshaled here, showing that p53 "body burden" is superior to conventional IHC "visual estimation" in tissue, suggests that by thus improving the correlation between the quantity of p53 expression in tissue and blood—the quantitation of p53$^{mut}$ in tissue could improve the reliability of its surrogate measure in blood.

Therefore, the p53 plasma concentrations of a small subset (N=16) of the cancer and adenoma patients enrolled in the same colorectal study were measured with the same p53$^{mut}$ ELISA as was used on the calibration cells—their blood being drawn immediately following surgery, before their p53 blood levels had a chance to drop. Their was a wide range in expression of p53 in tissue, including some patients negative for p53. For the p53$^+$ patients, their individual p53$^{mut}$ body burdens were calculated with the method of the invention. In order to compare the degree of tissue/plasma agreement for the invention's method of quantitation with that of the prior art of IHC staining, these absolute scores (pg) were reduced to three ordinal ranks (−, +, and ++). The same was done for the ELISA measures of the mutant p53 concentrations in the plasma sample from the same individuals. The ordinal ranks for the quantitation of p53 in tissue and blood were then displayed pairwise for the 16 patients (Table 16). With all scores for tissue and blood reduced to common ordinal ranks, per the current convention of "visual estimation", one can then determine whether the invention's method of protein quantitation is superior to the prior art in matching individual patient's p53 plasma scores with those of their tumor tissue, putatively the sole source of the p53$^{mut}$ present in their blood stream.

TABLE 16

Protein Quantitation with Method of the Invention: Matched Patient Tissue and Plasma

| Plasma (#) | Tissue (#) | p53$^{mut}$ ng/mL | p53$^{mut}$ ng/mm$^3$ | p53$^{mut}$ pg | Body Burden pg p53$^{mut}$ | Rank | Plasma pg p53$^{mut}$/mL | Rank |
|---|---|---|---|---|---|---|---|---|
| 981 | 91-6410/TA | 79.7 | 0.697 | 55.52 | | | | |
| 981 | 91-6410/TB | 101.4 | 3.54 | 359.0 | | | | |
| 981 | 91-6410/TB | 99.3 | 95.63 | 9496 | 9911 | ++ | 361 | ++ |
| 725 | 90-7792/T1 | 117.1 | 23.72 | 2778 | | | | |
| 725 | 90-7792/A3 | 126.1 | 0.45 | 56.76 | | | | |
| 725 | 90-7792/A3 | 117.0 | 27.05 | 3165 | 5999 | + | 107 | − |
| 1064 | 91-11293/T3 | 106.3 | 35.67 | 3791 | | | | |
| 1064 | 91-11188/1 | 44.9 | 7.74 | 347.5 | 4139 | + | ND | − |
| 845 | 90-13698/A3 | 93.3 | 0.28 | 26.12 | 26.12 | + | 167 | + |
| 819 | 90-12373/3L | 44.8 | 0.006 | 0.29 | 0.29 | + | 158 | − |
| 950 | 91-3324 | 46.7 | 0.003 | 0.13 | 0.13 | − | 29 | − |
| 968 | 91-4143 | 44.4 | 0.0003 | 0.01 | 0.01 | − | 77 | − |
| 843 | 90-14476/T2 | 0 | 0 | 0 | 0 | − | 595 | ++ |
| 1081 | 91-12965/A1 | 0 | 0 | 0 | 0 | − | ND | − |
| 958 | 91-3761 | 0 | 0 | 0 | 0 | − | 232 | + |
| 876 | 90-15055 | 0 | 0 | 0 | 0 | − | 814 | ++ |
| 863 | 90-14578/B | 0 | 0 | 0 | 0 | − | 75 | − |
| 858 | 90-14276/P10 | 0 | 0 | 0 | 0 | − | 13 | − |
| 982 | 91-6363/B | 0 | 0 | 0 | 0 | − | 90 | − |
| 964 | 91-4052 | 0 | 0 | 0 | 0 | − | 60 | − |
| 824 | 90-12581 | 0 | 0 | 0 | 0 | − | ND | − |

| Rank scoring: | Tissue | | Plasma | |
|---|---|---|---|---|
| | − | <0.28 pg (2x LLD) | − | <100 pg/mL (2x LLD) |
| | + | 0.28–6840 pg (2x–5x LLD) | + | 100–250 pg/mL |
| | ++ | >6840 pg (100 mg tumor @ A431 [p53]) | ++ | >250 pg/mL (>5x LLD) |

TABLE 17

Quantitation Method of Invention vs. Prior Art Visual Estimation
(Matched Tissue/Plasma Samples from Adenoma and Adenocarcinoma Patients)

p53 Quantitation (method of invention)
Mutant p53 in Tissue

| | | − | + | ++ | |
|---|---|---|---|---|---|
| Mutant p53 in Plasma | − | 8 | 1 | 0 | 9 |
| | + | 1 | 3 | 0 | 4 |
| | ++ | 2 | 0 | 1 | 3 |
| | | 11 | 4 | 1 | 16 |

Kappa coefficient (κ) = 0.54
p = 0.002

TABLE 17-continued

Quantitation Method of Invention vs. Prior Art Visual Estimation
(Matched Tissue/Plasma Samples from Adenoma and
Adenocarcinoma Patients)

|  |  | Visual Estimation (prior art) Mutant p53 in Tissue | | | |
|---|---|---|---|---|---|
|  |  | − or +/− | + or ++ | +++ |  |
| Mutant p53 in Plasma | − | 7 | 1 | 1 | 9 |
|  | + | 1 | 2 | 1 | 4 |
|  | ++ | 1 | 1 | 1 | 3 |
|  |  | 9 | 4 | 3 | 16 |

Kappa coefficient (κ) = 0.36
p = 0.025

The statistical test used for the comparison, the Kappa coefficient (κ), which has a maximum possible score of 1.00 (100%), measures the net strength of the tissue/plasma correlation, after subtracting the percentage association expected to occur by chance (given the relative insensitivity of categorical scoring, anything greater than 50% [κ≧0.50] is generally considered a strong correlation). The results of the pairings and the accompanying statistical test (Table 17) show that p53 "body burden" accounted for 54% (κ=0.54) of the concentration level of $p53^{mut}$ found in the same patients' blood, compared to only 36% (K=0.36) for the method of the prior art. Furthermore, while the degree of association between tissue and blood levels observed by both methods would be expected to occur in more than 95 out of 100 trials (α<0.05), the predicted false positive (FP) rate of the conventional approach would be 2.5 times out of 100 (p-value=0.025), while that of the method of the invention is about 10× better, i.e., 2/1000, (p-value=0.002).

12. Correlation of p53 with Tissue Class

Figure 13:
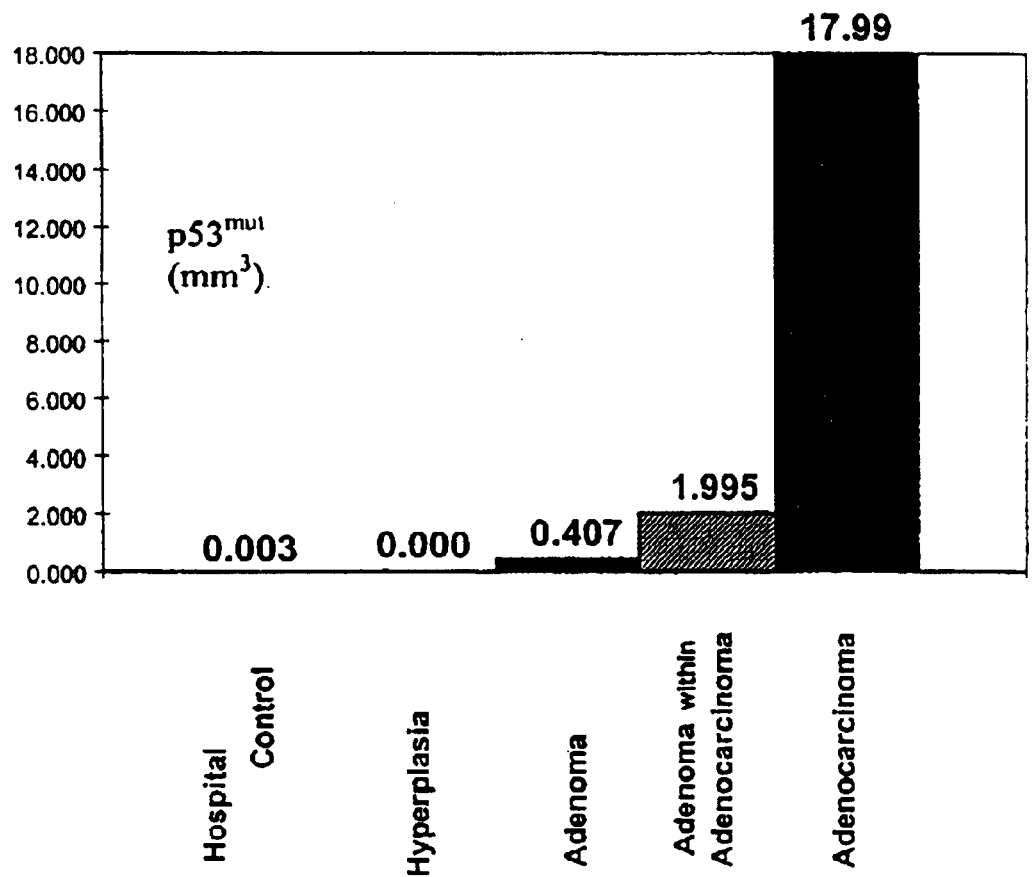
FIG. 13: p53$^{mut}$ Volume by Histologic Class. The average p53$^{mut}$ volume per lesion for the indicated histologic tissue types among the colorectal study patients.

Differences in the intensity of aberrant p53 expression among the patient groups and tissue classes are substantial, particularly between cases and controls. However, these differences pale in comparison to the wide disparities in the cellular spread of inactivated p53 (FIG. 13). The average volume for the adenocarcinoma lesions is nearly 6000 times greater than that of the lone $p53^+$ hospital control and almost 180,000 times greater than the single hyperplastic tissue that beat the $p53^+$ cut-off. The immunostained volume for the average adenocarcinoma is 44 times greater than that of the typical adenoma. The $p53^+$ volume for adenomatous tissue astride the cancerous core in the head of a polyp has made a leap in progression to malignancy; it is 4.9 times bigger than the pure adenoma, although a mere 11% of the p53 volume of a pure cancer A "critical mass" of mutant p53 (ca. 0.5–1.0 ng per lesion) appears to signal an adenoma becoming an adenocarcinoma. Although the total tumor size of the adenomas often equals or surpasses that of the adenocarcinomas, the adenoma tumor never acquired more than 500 pg of p53. Among those whose p53 had become transformed, 87% of the mutated p53 per tumor was accounted for by its covariance with total tumor area, as measured by the gravimetric method of the invention: $R^2$=0.87, p-value=0.001. There was no such linear correlation ($R^2$=0.14, p-value=0.103) between pg mutant p53/lesion and tumor size seen with by the prior art, i.e., estimating tumor dimensions with a metric ruler following surgery.

13. Correlation of p53 with Patient Prognosis

Patients were followed from the time of their diagnosis, which very nearly coincides with the colorectal surgery. Actuarial statistical approaches were used (Kaplan-Meier and Cox' Proportionate Hazards), so even partial follow-up provided information on the prognostic value of p53 and the clinico-pathological values for these patients. Among the colorectal cancer patients 23/24 (96%) had at least some follow-up. Median follow-up for the adenocarcinoma patients was 42 months, ranging from 6.5 to 76. There was at least some follow-up for most of the adenoma patients: 45/59 (76%), median follow-up=46 months. The three follow-up measures of interest were disease recurrence, survival and response to chemotherapy treatment.

Simple categorical survival analyses often lack the discriminatory power to detect causal relations, partly because they cannot measure dose-response relationships, and partly because they ignore valuable information regarding the duration of the follow-up. For example, the death of a patient who survived one month past diagnosis is scored the same (negative response) as someone who survived 5 years. On the other hand, either the Kaplan-Meier or Cox' Proportionate Hazards analyses can combine a binary exposure status ($p53^+$ or $p53^-$) with survival time, a continuous variable. Even if the endpoint (death, recurrence) never occurs during the follow-up period, one can still incorporate this valuable "censored" observation into determining degrees of patient risk. Both Kaplan-Meier and Cox are suitable for studies such as this in which there were small numbers of surviving (censored) patients with unequal periods of observation.

The Kaplan-Meier curves descend because at each successive follow-up time point the probability of survival of the group as a whole decreases as the number of terminal events (death or recurrence) accumulates, and the number of survivors drops. The x axis is time-since-diagnosis and they axis (cumulative survival) is the probability of the event at each successive month of follow-up. The size of the gap between the survival curves for those exposed to the risk factor ($p53^+$) and those not ($p53^-$) is a rough graphic indicator of relative risk. These curves are widely-used for the interpretation of clinical follow-up.

TABLE 18

Relative Risk of Death Among $p53^+$ Patients. Cell Imaging
Method of Invention
ADENOCARCINOMA SURVIVAL vs. p53 STATUS
(Proportional Hazards Regression)

| p53 STATUS | Label | Frequency | Deaths | Censored |
|---|---|---|---|---|
| $p53^-$ | 0 | 9 | 11 | 12 |
| $p53^+$ | 1 | 14 | (48%) | (52%) |
|  |  | 23 |  |  |

Baseline Hazard Rate* = 63.079
Categorical Covariate ($p53^+$) Hazard Rate* = 55.764
(*−2 Log Likelihood estimate)

|  | $\chi^2$ | df | Significance |
|---|---|---|---|
| Overall (score)* | 6.169 | 1 | 0.0130 (see K–M) |
| (−2LL) Change from Baseline Risk** | 7.315 | 1 | 0.0068 |

TABLE 18-continued

Relative Risk of Death Among p53+ Patients. Cell Imaging
Method of Invention
ADENOCARCINOMA SURVIVAL vs. p53 STATUS
(Proportional Hazards Regression)
Variables in the Cox ln (Hazard) Regression Equation

| Variable | $\beta_1$ | df | Significance | $R_{x|y}$ | $e^{\beta_1}$ (Relative Risk) |
|---|---|---|---|---|---|
| p53+ | 2.1770 | 1 | 0.0387 | 0.1899 | 8.8202 |

*H: $\beta_0$ and $\beta_1$ = 0 ($\chi^2$ approximation to Likelihood-Ratio test)
**H: $\beta_0$ = $\beta_1$ (Likelihood-Ratio test)

Cancer patient survival was, by far, the end-point most strongly correlated with the patient's p53 status. This was true for both the binary cell imaging definition of p53+ (Table 18) and the absolute quantitation of p53 body burden (ng) (Table 21). FIGS. 14 and 15 summarize the Kaplan-Meier survival approach utilizing p53+ and p53− binary scores. FIG. 15 shows patient survival based upon the p53 cell imaging method of the invention for those 23 cancer patients with evaluable follow-up data; FIG. 14 does the same for the prior art of visual estimation. The much steeper drop evident in the curve generated by the method of the present invention reflects the improved predictive ability of the CID compared to subjective visual estimation of p53+ staining. As Table 19 illustrates, the prior art leads to a "misclassification error" by incorrectly assigning p53+ status to five patients. These same people were deemed to be p53−, using the calibration cells as CID lab controls and the normal patients' staining intensity as the criterion for p53+. The CID's demonstrated accuracy and reliability, as practiced herein, revealed the initial false-positives. Note the dramatic improvement in the p-value of the "log rank" statistic—from 0.45, using visual estimation, to 0.01, using p53 cell imaging. This is consistent with the far greater discrepancy between the p53+ and the p53− cancer patients with respect to their average survival time (Tables 19 and 20). That the CID, as applied using the method of the invention, truly offers a better prognostic method, is suggested by the biological consistency of the reassignment of surviving patients into the group with a functioning p53 tumor suppressor gene. Despite the earlier proven correlation between the two scoring methods when using less discriminating aggregate statistical measures, the considerably increased predictive power of cell imaging to parse out the survival risk for individual patients when combined with Kaplan-Meier analysis is evident.

Figure 16:
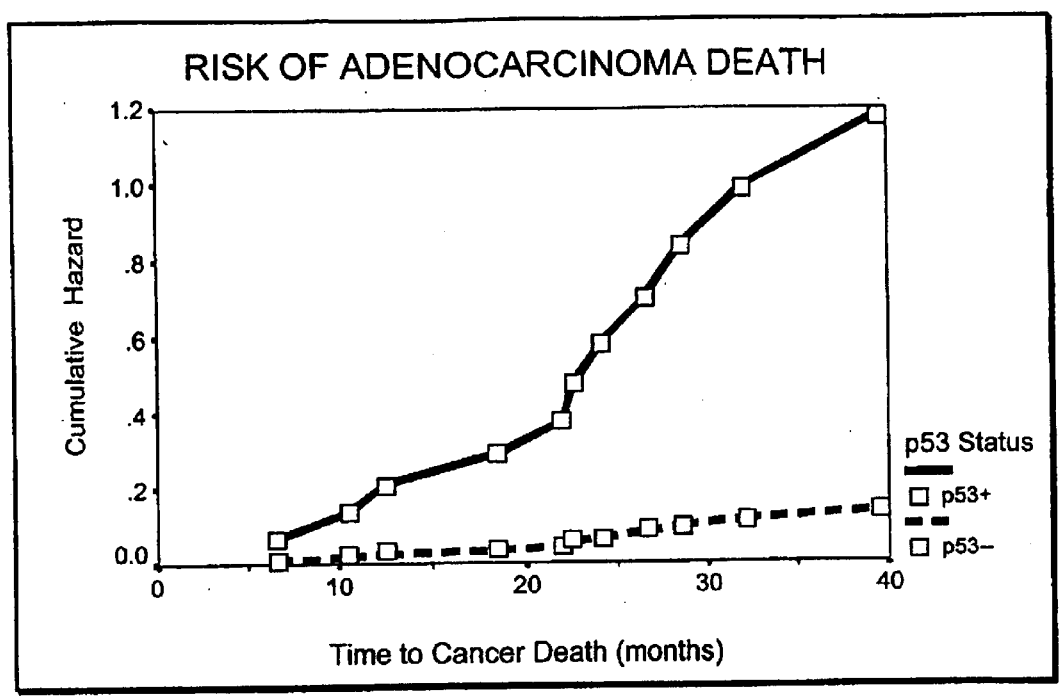
FIG. 16: Constant Rate of Acceleration in the Risk of Death. Cell Imaging of Method. A plot of the constant rate of accelerating risk of cancer-related death over time compared to the baseline survival risks. Categorical p53 status was assigned according to the cell imaging method of the invention.

The Cox' *Proportionate Hazards* statistical procedure, when combined with CID, was able to reveal the size of increased patient risk from the loss of their tumor suppressor protection. These patients were nearly 9 times more likely to die over the observed follow-up period (p=0.0387). FIG. 16 shows two important aspects of the power of p53 inactivation to shorten the lives of colorectal cancer patients. First, the roughly constant upward slope of the cumulative hazard among p53+ patients shows that the rate of accelerated death in this group is constant in the period following its detection. Second, while p53 may interact with the other main prognostic risk factors such as stage and grade, the equally flat, near-zero, hazard line for the p53− patients proves—since both groups were similar in the stage and grade of their tumors—that a patient's categorical p53 status is a powerful independent risk factor. Although not shown here, the effect of p53 status upon survival of these people was >2× that caused by the transition of tumors from "well" to "moderately differentiated" and nearly 2× tumor penetration of the basement membrane (stage B⇒C). While the traditional risk factors—tumor stage and grade—also had a strong effect upon survival beyond that contributed by p53, this was not true of tumor size; in fact, the average size of the p53− cancers was greater than that of the p53+ cancers. If we trust univariate analysis, only among those patients with p53+ tumors was tumor size prognostic, accounting for 39% of the variability in survival duration ($R^2$=0.39, p-value=0.018).

TABLE 19

Survival Analysis with Prior Art p53 Visual Estimates
ADENOCARCINOMA SURVIVAL vs. p53 STATUS
(Kaplan-Meier)

| p53−<br>Time<br>(months) | Status | Cumulative<br>Survival | Standard<br>Error | Cumulative<br>Events | Number<br>Remaining |
|---|---|---|---|---|---|
| 6.5 | Dead | 0.7500 | 0.2165 | 1 | 3 |
| 45.0 | Alive | | | 1 | 2 |
| 48.0 | Alive | | | 1 | 1 |
| 56.0 | Alive | | | 1 | 0 |

Number of Cases: 4 - Censored: 3 - (75%) - Events: 1
Mean Survival Time = 43.6 months

| p53+<br>Time<br>(months) | Status | Cumulative<br>Survival | Standard<br>Error | Cumulative<br>Events | Number<br>Remaining |
|---|---|---|---|---|---|
| 10.5 | Dead | 0.9474 | 0.0512 | 1 | 18 |
| 12.5 | Dead | 0.8947 | 0.0704 | 2 | 17 |
| 18.5 | Dead | 0.8421 | 0.0837 | 3 | 16 |
| 22.0 | Dead | 0.7895 | 0.0935 | 4 | 15 |
| 22.5 | Dead | 0.7368 | 0.1010 | 5 | 14 |
| 24.0 | Dead | 0.6842 | 0.1066 | 6 | 13 |
| 26.5 | Dead | 0.6316 | 0.1107 | 7 | 12 |
| 28.5 | Dead | 0.5789 | 0.1133 | 8 | 11 |
| 32.0 | Dead | 0.5263 | 0.1145 | 9 | 10 |
| 38.5 | Alive | | | 9 | 9 |
| 39.5 | Dead | 0.4678 | 0.1158 | 10 | 8 |
| 41.0 | Alive | | | 10 | 7 |
| 44.5 | Alive | | | 10 | 6 |
| 50.5 | Alive | | | 10 | 5 |
| 52.5 | Alive | | | 10 | 4 |
| 55.0 | Alive | | | 10 | 3 |
| 61.0 | Alive | | | 10 | 2 |
| 72.5 | Alive | | | 10 | 1 |
| 76.0 | Alive | | | 10 | 0 |

Number of Cases: 19 - Censored: 9 - (47%) - Events: 10
Mean Survival Time = 48.2 months

| | Statistic | df | Significance |
|---|---|---|---|
| Log Rank | 0.57 | 1 | 0.449 |

TABLE 20

Reduction of Misclassification Error With p53 Cell
Imaging Method of Invention
ADENOCARCINOMA SURVIVAL × p53 STATUS
(Kaplan-Meier)

| p53−<br>Time<br>(months) | Status | Cumulative<br>Survival | Standard<br>Error | Cumulative<br>Events | Number<br>Remaining |
|---|---|---|---|---|---|
| 6.5 | Dead | 0.8889 | 0.1048 | 1 | 8 |
| 38.5 | Alive | | | 1 | 7 |
| 41.0 | Alive | | | 1 | 6 |
| 45.0 | Alive | | | 1 | 5 |
| 48.0 | Alive | | | 1 | 4 |
| 55.0 | Alive | | | 1 | 3 |
| 56.0 | Alive | | | 1 | 2 |
| 61.0 | Alive | | | 1 | 1 |

TABLE 20-continued

| | | | | |
|---|---|---|---|---|
| 76.0 | Alive | | 1 | 0 |

Number of Cases: 9 - Censored: 8 (89%) - Events: 1
Mean Survival Time = 68.3 months p53$^+$

| Time (months) | Status | Cumulative Survival | Standard Error | Cumulative Events | Number Remaining |
|---|---|---|---|---|---|
| 10.5 | Dead | 0.9286 | 0.0688 | 1 | 13 |
| 12.5 | Dead | 0.8571 | 0.0935 | 2 | 12 |
| 18.5 | Dead | 0.7857 | 0.1097 | 3 | 11 |
| 22.0 | Dead | 0.7143 | 0.1207 | 4 | 10 |
| 22.5 | Dead | 0.6429 | 0.1281 | 5 | 9 |
| 24.0 | Dead | 0.5714 | 0.1323 | 6 | 8 |
| 26.5 | Dead | 0.5000 | 0.1336 | 7 | 7 |
| 28.5 | Dead | 0.4286 | 0.1323 | 8 | 6 |
| 32.0 | Dead | 0.3571 | 0.1281 | 9 | 5 |
| 39.5 | Dead | 0.2857 | 0.1207 | 10 | 4 |
| 44.5 | Alive | | | 10 | 3 |
| 50.5 | Alive | | | 10 | 2 |
| 52.5 | Alive | | | 10 | 1 |
| 72.5 | Alive | | | 10 | 0 |

Number of Cases: 14 - Censored: 4 (28%) - Events: 10
Mean Survival Time = 37.6 months

| | Statistic | df | Significance |
|---|---|---|---|
| Log Rank | 6.17 | 1 | 0.013 |

But what about the absolute quantitation offered by the translation of these CID optical density values into actual ng mutant p53 using the calibration (standard) curves for the various staining batches? Dose/response is, perhaps, the strongest proof of cause and effect. There was a very large difference in the dose of mutant p53 (whether measured as ng/mg crypt protein concentration or as ng body burden) among those who died vs. those who did not, and between those who responded to chemotherapy and those that did not (data not shown). Table 21 formalizes the relationship between dose and cumulative survival using mass quantities of transforming p53 protein. Note that both the overall $\chi^2$ as well as the regression equation itself were highly significant. The data graphed in FIG. 17 was taken from the time series in Table 21* and makes the point that simply dichotomizing patients with regard to their p53 protein status (using either the prior art of visual estimation or the cell imaging method of the invention) masks a basic fact: the quantity of p53$^{mut}$ also greatly affects cancer patient survival. For example, patients with only 1 ng p53$^{mut}$ survive about as well as a patient with completely normal p53, while those with 9 ng die surely and quickly. When the dichotomous variable, p53 status (from CID), was combined with the continuous variable, body burden, in a single Cox' model, the latter kept both its significance and nearly all its size, while the former lost its significance and half its size (results not shown).

*The figures reflect the assumption, given previous linear curves, that since the linearized log of the hazard rate provided the basis for the 1 ng hazard rate, a 5× greater amount of p53 would have a 5× steeper regression coefficient ($\beta$) and, therefore, a corresponding multiple of the value of $e^{(5\beta x)}$, determining the rate of the decrement in survival for each comparable time compared to the baseline (p53$^-$) population.

Figure 18:
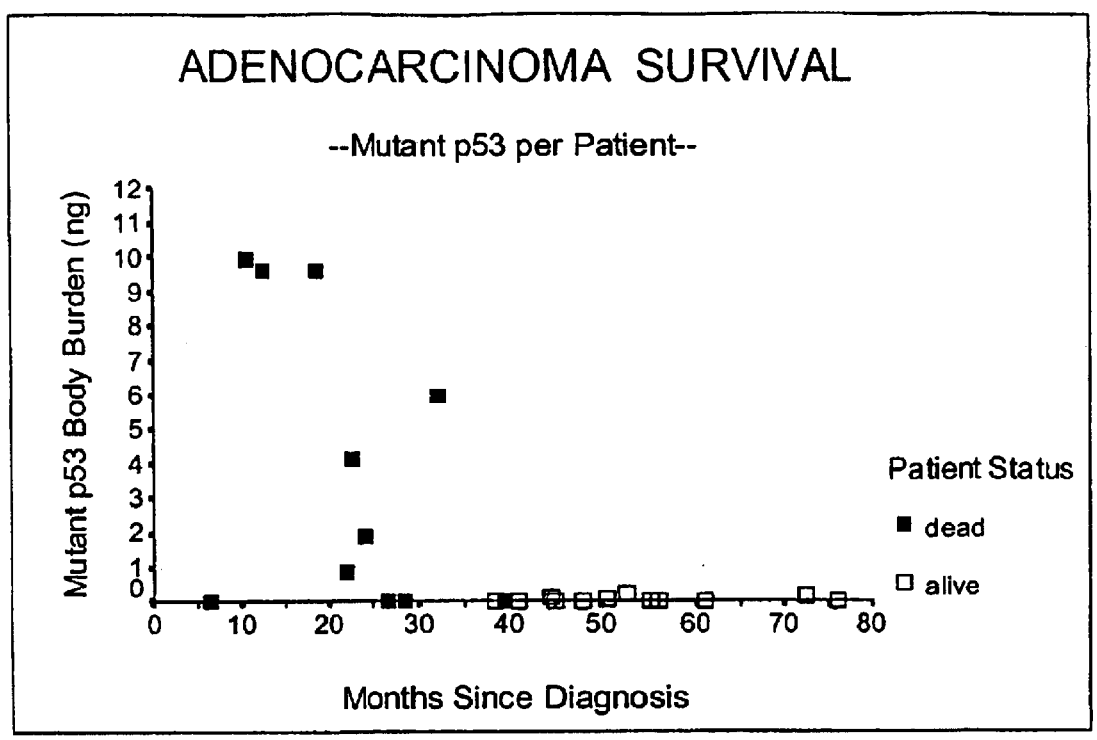
FIG. 18: Dosimetry of Death II. Quantitation of the Method of the Invention. Whether the patient's adenocarcinoma contained mutant p53 strongly influenced the risk of death following surgery; the speed with which it occurred was proportional to the size of the patient's total tumor burden of the cancer protein.
Figure 19A:
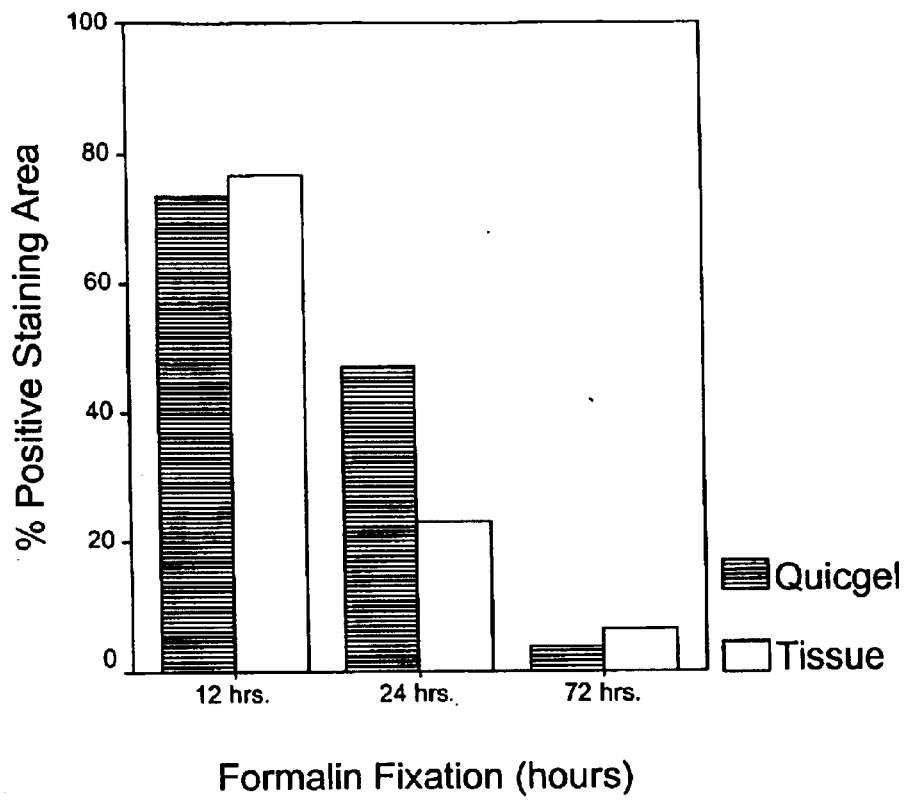
FIG. 19: Inability of method of U.S. Pat. No. 5,610,022 to extrapolate back to the pre-fixation immunoreactivity of a tissue sample, based upon the staining area of pseudotissue internal control.
Figure 19B:
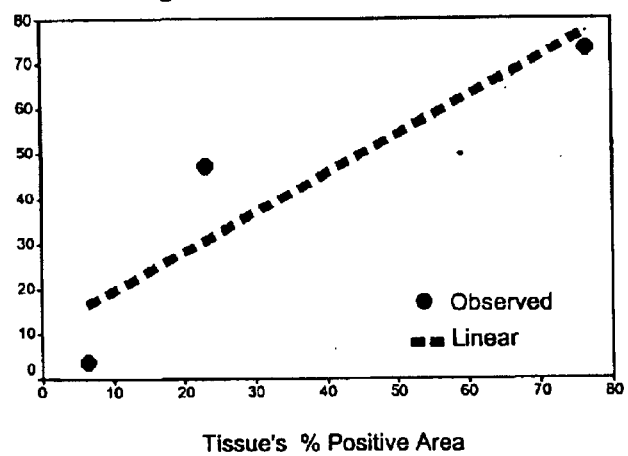
Figure 20A:
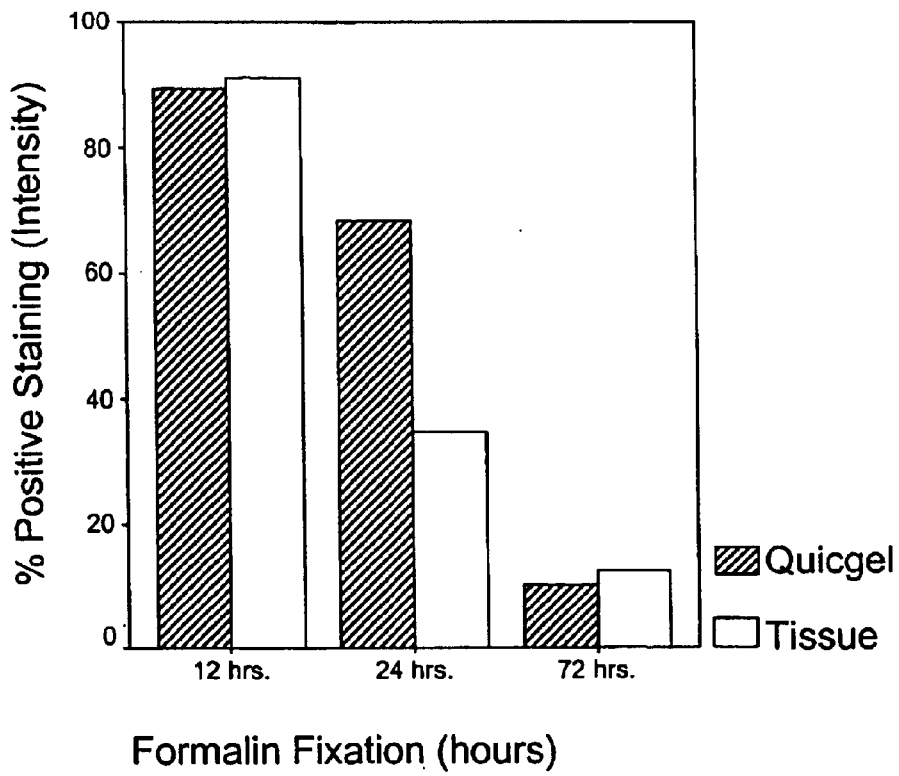
FIG. 20: Inability of method of U.S. Pat. No. 5,610,022 to extrapolate back to the pre-fixation immunoreactivity of a tissue sample, based upon the staining intensity of pseudotissue internal control.
Figure 20B:
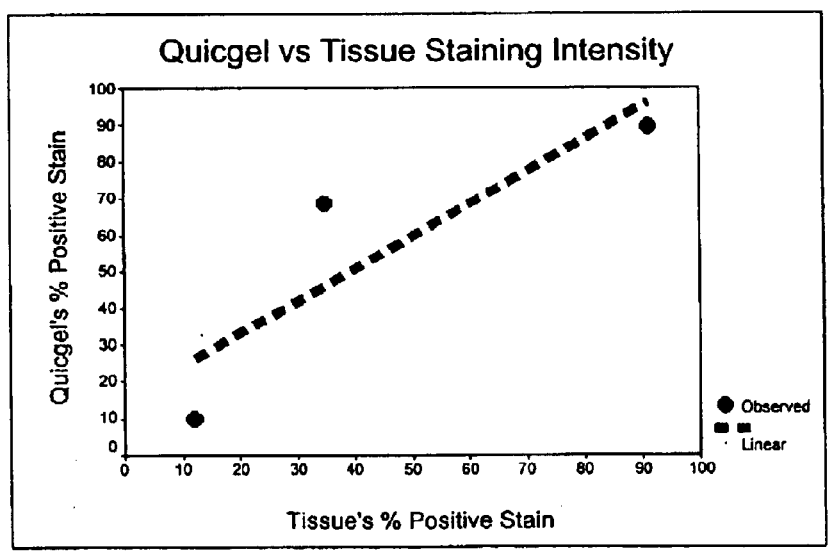

The predictive role of p53 body burden becomes even clearer in its ability to predict not only the risk of colorectal adenocarcinoma death, but also the speed of its onset, when we look at the raw survival data for both the p53$^-$ and the p53$^+$ patients. The simple scatterplot in FIG. 18 illustrates the gap between these two groups. Those with normal p53 in their cancerous tumors rarely died during the follow-up period, and never within 38 months of diagnosis and surgery. Those with at least some mutant p53 protein in their tumor(s) often died and never lived beyond 40 months. Furthermore, the steeply inverse relationship between amount of the dysfunctional protein and survival duration in a regression for the p53$^+$ patients was readily discernable. ($R^2$=0.53, p-value=0.018; calculations not shown).

TABLE 21

Patient Prognosis vs. Cancer Protein Dose - Quantitation by Method of Invention
ADENOCARCINOMA SURVIVAL × MUTANT p53 BODY BURDEN
(Proportional Hazards Regression)

| p53 | | CENSORED | EVENTS | BASELINE HAZARD | p53 BODY BURDEN |
|---|---|---|---|---|---|
| p53$^-$ | p53$^+$ | (Alive) | (Dead) | (−2 LL) | (−2 LL) |
| 9 (39%) | 14 (61%) | 12 (52%) | 11 (48%) | 63.079 | 50.688 |

| | $\chi^2$ | df | Significance |
|---|---|---|---|
| Overall (score)* | 19.860 | 1 | p < 0.0001 |
| (−2 LL) Change from Baseline Hazard** | 12.391 | 1 | 0.0004 |

Proportionate Hazards Regression Equation

| Variable | $\beta_1$ | error | df | Significance | R | $e^{\beta_1}$*** |
|---|---|---|---|---|---|---|
| ng p53/patient | 0.3497 | 0.0993 | 1 | 0.0004 | 0.4062 | 1.4186 |

| Time (months) | Baseline Cumulative Hazard | Baseline Cumulative Survival | 1 ng Body Burden Cumulative Survival | 9 ng Body Burden Cumulative Survival |
|---|---|---|---|---|
| 6.5 | 0.0076 | 0.992 | 0.989 | 0.829 |
| 10.5 | 0.0154 | 0.985 | 0.979 | 0.703 |
| 12.5 | 0.0239 | 0.976 | 0.966 | 0.576 |
| 18.5 | 0.0331 | 0.967 | 0.954 | 0.458 |
| 22.0 | 0.0430 | 0.946 | 0.924 | 0.275 |
| 22.5 | 0.0539 | 0.946 | 0.924 | 0.275 |

TABLE 21-continued

Patient Prognosis vs. Cancer Protein Dose - Quantitation by Method of Invention
ADENOCARCINOMA SURVIVAL × MUTANT p53 BODY BURDEN
(Proportional Hazards Regression)

| | | | | |
|---|---|---|---|---|
| 24.0 | 0.0660 | 0.934 | 0.907 | 0.204 |
| 26.5 | 0.0795 | 0.920 | 0.888 | 0.144 |
| 28.5 | 0.0948 | 0.905 | 0.867 | 0.098 |
| 32.0 | 0.1125 | 0.888 | 0.844 | 0.063 |
| 39.5 | 0.1340 | 0.866 | 0.815 | 0.035 |

*H: $\beta_0$ and $\beta_1 = 0$ ($X^2$ approximation to Likelihood-Ratio test)
**H: $\beta_0 = \beta_1$ (Likelihood-Ratio test)
***41.86% decrement in survival rate compared to p53⁻ patients per additional month of follow-up for those with a 1 ng p53 body burden; 2227% decrement for those with 9 ng $p53^{mut}$.

These final examples of the results of the protein quantitation also suggest the potential power of the discovery of the actual amounts of disease-causing proteins. Quantitation of multiple proteins directly in the diseased tissue measured at the cellular level makes it possible to observe the partial correlation coefficients of independent causal factors, their relative strength, statistical significance, interactions and timing over the natural history of the disease in question, thus making it possible to estimate the relative rates of molecular exposure and probabilities of outcome. Such multivariate measures could be applied to either retrospective case-control studies using proportionate hazards and prospective exposure cohort studies using logistic regression, for example.

What advantages then, does the method of the invention offer? In the first place, it retains all the advantages of the prior art of tissue analysis vis-a-vis alternative approaches, such as flow cytometry.

a) it can be done with much smaller quantities of tissue than tumor tissue extracts; thus, it is less invasive and expensive, and can be done earlier in the progression of the disease;

b) as an in-situ technique, it can readily isolate specific cell types and histopathologies, thus avoiding ecological fallacies about molecular causes of disease and the dilution of the protein in extraneous cellular material;

c) both the tissue block and the analyzed slides can be archived indefinitely for purposes of medical documentation or later review by others.

d) since nearly all the original tissue is retained, the identical lesion can be easily analyzed for quantities of other biomolecules thought to be a co-factor in the disease;

e) using different stains, histopathology can be quickly and easily combined with IHC on the same lesion.

Moreover, relative to the "prior art", whether or not that "art" is aided by CID, the method of the invention provides substantial improvements.

First, at the simple binary level of measurement, we have seen its ability to reduce misclassification error between the disease and the risk factor. This approach was seen, in the case of $p53^{mut}$, to greatly improve the ability to predict patient survival. It also correlated with response to chemotherapy among these Stage C and D colorectal cancer patients.

Second, this improved connection between the cause and effect in tissue will also allow for more accurate correlations between diseased tissue and the patients' blood concentrations. This is a precondition for using blood samples to do less invasive and less costly monitoring of patient survival and response to treatment. However, with the exception of antigens that are unusually specific for a given disease, e.g., Prostrate Specific Antigen (PSA), and HIV, the risk factor must first be correctly identified in the diseased tissue. Such a surrogate medium as blood is sampled from the entire body. Cancer proteins (including $p53^{mut}$) found in blood have, at times, been a result of exposure rather than from a disease or from an unrelated disease and tissue, or from the cardio-vascular system itself [114].

Third, the calibration cells of the method can virtually eliminate laboratory artifact from immunostaining scoring. Within a given lab they can be used simply to adjust for "batch effect" differences over time, whether that be in terms of the relative intensity of the CID (Table 5) or absolute protein quantities (Table 11). Thus, data from patient tissue scored at different times and from different studies can be collectively analyzed. These matrix-embedded cells also make it possible to aggregate results among different labs and surgical pathology departments by controlling for differences in procedure and reagents and for arriving at common criteria for a definition of "positive".

Fourth, for the abnormal p53 protein and possibly others, the in vitro cells provide a proportionate measure of the biological effects of different tissue concentrations. Thus, rather than rely upon statistical definitions of disease, CID done with such cells will enable clinicians to define different disease states, based upon medically significant amounts of antigens in patient tissue.

Fifth, absolute quantitation of p53 provided evidence of both a dose threshold in the transition from pre-cancer to cancer and a dose-response effect for patient survival. This should allow for better prediction of patient risk and stronger proof of disease causality.

Lastly, new molecular-level modalities of tumor treatment, such as cancer-specific vaccines.[115, 116], are emerging to replace or augment current chemotherapy and radiotherapy, given the systemic toxicity and limited effectiveness of the latter. One strategy is to use recombinant endogenous angiogenesis inhibitors to starve tumors of their blood supply [117–119]. Several biotechnology firms are developing apoptosis-inducing peptides and gene fragments [120]. Others are eschewing whole-body therapy for the targeting of individually diseased cells [121], some with $p53^{mut}$-specific cytotoxic adenoviruses [122, 123]. For such "in situ pharmacology" this invention should prove useful in prescribing the appropriate treatment dosage.

Modifications of the above described modes for carrying out the invention will be obvious to those of skill in the fields of oncology, microscopy, immunohistology, cytology, and related fields, and such modifications are intended to be within the scope of the following claims. All references cited herein are hereby incorporated by reference in their entirety.

REFERENCES

1. *Staining Procedures.* Editor George Clark. Biological Staining Commission. 4$^{th}$ ed. Baltimore and London: Williams & Wilkins, 1981.

2. *Theory and Practice of Histological Techniques.* John D. Bancroft and Alan Stevens. 3$^{rd}$ ed. Edinburgh: Churchill-Livingston, 1990.
3. *Principles and Practice of Surgical Pathology.* Editor Steven G. Silverberg. 3$^{rd}$ ed. New York: John Wiley & Sons, 1983.
4. Wheater, Paul, et al. *Basic Histopathology, A Colour Atlas and Text.* Edinburgh: Churchill Livingstone, 1991.
5. Baytner, S., B. Mitmaker, P. H. Gordon, and E. Wang. "Immunohistochemical Expression of Mutant p53 Oncogene in Transitional Mucosa Adjacent to Human Colon Cancer." *Clinical & Investigative Medicine* 16.5 (1993): 379–85.
6. Press, Michael F., Malcom C. Pike, Victoria R. Chazin, Gene Hung, Judith A. Udove, Mitchell Markowicz, John Danyluk, William Godolphin, Mark Sliwkoski, Robert Akita, Malcom C. Paterson, and Dennis J. Slamon. "Her-2/Neu Expression in Node-Negative Breast Cancer: Direct Tissue Quantitation by Computerized Image Analysis and Association of Overexpression With Increased Risk of Recurrent Disease." *Cancer Research* 53 (1993): 4960–70.
7. Baldo, Brian A. "Protein Blotting: Research, Applications and Its Place in Protein Separation Methodology." *Advances in Electrophoresis.* Editors A. Chrambach, M. J. Dunn, and B. J. Radola. Vol. 7. Weinheim: VCH. 409–80. See p. 424: 45 kd protein transfer ~50–75%. semi-dry or addition of 0.1% SDS to transfer buffer on the high end.
8. Hancock, Kathy, and Victor C. W. Tsang. "India Ink Staining of Proteins on Nitrocellulose." *CRC Handbook of Immunoblotting of Proteins.* Editors and authors Ole J. Bjerrum and Niels H. H Heegaard. Vol. I. Boca Raton: CRC Press, Inc., 1988. 127–36. 72–99% gel protein recovery (p. 135).
9. Burnette, W. Neal. "'Western Blotting': Electrophoretic Transfer of Proteins From Sodium Dodecyl Sulfate—Polyacrylamide Gels to Unmodified Nitrocellulose and Radiographic Detection With Antibody and Radio-iodinated Protein A." *Analytical Biochemistry* 112 (1981): 195–203.
10. The American Society of Clinical Oncology. "Clinical Practice Guidelines for the Use of Tumor Markers in Breast and Colorectal Cancer." *Journal of Clinical Oncology,* Vol. 14, No. 10 (October), 1996: 2843–2877. See especially, pp. 2843 and 2853–2854.
11. Chen, X., J. Bargonetti, and C. Prives. "p53, Through p21 (WAF1/CIP1), Induces Cyclin D1 Synthesis." *Cancer Research* 55.19 (1995): 4257–63.
12. Cross, Shawn M., Carissa A. Sanchez, Catherine A. Morgan, Melana K. Schimke, Stig Ramel, Rejean L. Idzerda, Wendy H. Raskind, and Brian J. Reid. "A p53-Dependent Mouse Spindle Checkpoint." *Science* 267 (1995): 1353–56.
13. Stewart, Nancy, Geoffrey G. Hicks, Frixos Paraskevas, and Michael Mowat. "Evidence for a Second Cell Cycle Block at G2/M by p53." *Oncogene* 10 (1995): 109–15.
14. Hartwell, L., et al. "Cell Cycle Checkpoints, Genomic Integrity, and Cancer." *Cold Spring Harbor Symposia on Quantitative Biology*: Cold Spring Harbor, N.Y.: Cold Spring Harbor Laboratory Press, 1994. 259–63.
15. Montenarh, Mathias. "Biochemical, Immunological, and Functional Aspects of the Growth-Suppressor/Oncoprotein p53." *Critical Reviews in Oncogenesis* 3 (1992): 233–56. See 8 cited secondary references on page 238.
16. Thomas, Rees, Leonard Kaplan, Nancy Reich, David P. Lane, and Arnold J. Levine. "Characterization of Human p53 Antigen Employing Primate Specific Monoclonal Antibodies." *Virology* 131 (1983): 502–17.
17. Hassapoglidou, Stavroula, Eleftherios P. Diamandis, and Donald J. A. Sutherland. "Quantitation of p53 Protein in Tumor Cell Lines, Breast Tissue Extracts and Serum With Time-Resolved Immunofluorometry." *Oncogene* 8 (1993): 1501–09.
18. Vojtêsek, B., C. J. Fisher, D. M. Barnes, and D. P. Lane. "Comparison Between p53 Staining in Tissue Sections and p53 Proteins Levels Measured by an ELISA Technique." *British Journal of Cancer* 67 (1993): 1254–58.
19. Joypaul, B. V., B. Vojtesek, E. L. Newman, D. Hopwood, A. Grant, D. P. Lane, and A. Cuschieri. "Enzyme-Linked Immunosorbent Assay for p53 in Gastrointestinal Malignancy: Comparison With Immunohistochemistry." *Histopathology* 23 (1993): 465–70.
20. Oncogene Science, Inc. 1995 *Research Products Catalogue.* Cambridge Mass. 1995. See page 94.
21. Reiss, M., et al. "Status of the p53 Tumor Suppressor Gene in Human Squamous Carcinoma Cell Lines." *Oncology Research* 4. 8–9 (1992): 349–57. Also cited: the prior work of Scheffner, et al., in *Proceedings of the National Academy of Science, USA*. 88:5523–5527.
22. Iggo, Richard, Kevin Gattner, Jiri Bartek, David Lane, and Adrian L. Harris. "Increased Expression of Mutant Forms of p53 Oncogene in Primary Lung Cancer." *The Lancet* 335 (1990): 675–79. In the text of this article, the authors cite "unpublished results" without explaining how the estimate of 5,000 molecules p53/cell was obtained.
23. Agrawal, Reitu S., Yash P. Agrawal, and Mäntyjärvi. "Flow Cytometric Quantitation of C-Myc and p53 Proteins in Bovine Papillomavirus Type 1-Transformed Primary Mouse Fibroblasts." *Cytometry* 17 (1994): 237–45.
24. Virji, M. A., B. Rosendale, and M. et al. Piper. "Circulating Levels of a Mutant p53 Protein in Patients With Hepatocellular Carcinoma." *Proceedings of the American Association of Cancer Research* 33.A1508 (1992).
25. Rosanelli, G. P., G. H. Wirnsberger, and P. et al. Purstner. "DNA Flow Cytometry and Immunohistochemical Demonstration of Mutant p53 Protein Versus TPS and Mutant p53 Protein Serum Levels in Human Breast Cancer." *Proceedings of the American Association for Cancer Research* 34 (1993): A1353.
26. Luo, J. C., R. Zehad, S. Antilla, and et al. "Detection of Serum p53 Protein in Lung Cancer Patients." *Journal of Occupational Medicine* 36 (1994): 155–60.
27. Greco, Claudia, et al., "Detection of C-Myb Genetic Alterations and Mutant p53 Serum Protein in Patients with Benign and Malignant Colon Lesions." *Anticancer Research* 14 (1994): 1433–40.
28. Luo, Jiin-Chyuan, Alfred I. Neugut, Gail Garbowski, Kenneth Forde, Michael Treat, Steven Smith, Walter Carney, and Brandt-Rauf. "Levels of p53 Antigen in the Plasma of Patients with Adenomas and Adenocarcinomas of the Colon." *Cancer Letters* 91 (2) (1995): 235–40.
29. Shim, K. S., et al., Increased Serum Levels of p53 Protein in Patients With Colorectal Cancer: A Comparison Before and After Surgical Resection. Clinical Investigations Abstract #3488, Vol. 38, 1997. *Proceedings of the American Association for Cancer Research.*
30. Rosanelli, G. P., G. H. Wirnsberger, and P. et al. Purstner. "DNA Flow Cytometry and Immunohistochemical Demonstration of Mutant p53 Protein Versus TPS and Mutant p53 Protein Serum Levels in Human Breast Cancer." *Proceedings of the American Association for Cancer Research* 34 (1993): A1353.
31. Fontanini, Babriella, Lisa Fiore, Daniela Bigini, Silvana Vignati, Simonetta Calvo, Alfredo Mussi, Marco Lucchi, Carlo A. Angeletti, Giorgio Merlo, and Fulvio Basolo. "Levels of p53 Antigen in the Serum of Non-Small Cell Lung Cancer Patients Correlate With Positive p53 Immunohistochemistry on Tumor Sections, Tumor Necrosis and Nodal Involvement." *International Journal of Oncology* 5 (1994): 553–58.

32. Suwa, H., G. Ohshio, N. Okada, Z. Wang, M. Fukumoto, T. Imamura, and M. Imamura. "Clinical Significance of Serum p53 Antigen in Patients with Pancreatic Carcinomas." *Gut* 40.5 (1997): 647–53.

33. Husgafvel-Pursiainen, Kirsti, Annamaria Kannio, Panu Oksa, Tuula Suitiala, Heikki Koskinen, Riitta Partanen, Kari Hemminki, Steven Smith, Rachel Rosenstock-Leibu, and Paul W. Brandt-Rauf. "Mutations, Tissue Accumulations, and Serum Levels of p53 in Patients with Occupational Cancers from Asbestos and Silica Exposure." *Environmental and Molecular Mutagenesis* 30 (1997): 224–30.

34. Roth J A. "Gene replacement strategies for cancer". *Israel Journal of Medical Sciences* 32: 89–94; 1996.

35. Roth J A. "Modification of tumor suppressor gene expression and induction of apoptosis in non-small cell cancer (NSCLC) with an adenovirus vector expressing wildtype p53 and Cisplatin". *Human Gene Therapy* 7: 1013–30; 1996.

36. Roth J A. "Modification of tumor suppressor gene expression in non-small cell lung cancer (NSCLC) with a retroviral vector expressing wildtype (normal) p53." *Human Gene Therapy* 7: 861–74; 1996.

37. Manne, Upender, et al. "Re: 'Loss of Tumor Marker-Immunostaining Intensity on Stored Paraffin Slides of Breast Cancer'". *Journal of the National Cancer Institute*. Letter to Editors. Apr. 16, 1997. 89 (8): 585–586. The replying authors' topic was the absence of staining loss in stored paraffin blocks, not slides (the study of the initial authors).

38. Lee, L., B. Elenbaas, A. J. Levine, and J. Griffith. "p53 and Its 14 Kd C-Terminal Domain Recognize Primary DNA Damage in the Form of Insertion/Deletion Mismatches." *Cell* 81 (1995): 1013–20. Cited in Smith, M. L. (1995).

39. Baas, I. O., J. W. Mulder, G. J. Offerhaus, B. Vogelstein, and S. R. Hamilton. "An Evaluation of Six Antibodies for Immunohistochemistry of Mutant p53 Gene Product in Archival Colorectal Neoplasms." *Journal of Pathology* 172.1 (1994): 5–12.

40. Tominaga, Osamu, Richard Hamelin, Yorghos Remvikos, Remy Salmaon, and Gilles Thomas. "p53 From Basic Research to Clinical Applications." *Critical Reviews in Oncogenesis* 3 (1992): 257–82.

41. Perkins, Archibald, and George F. Vandewoude. "Principles of Molecular Cell Biology of Cancer: Oncogenes." *Cancer, Principles & Practice of Oncology*. Editors. Vincent T. DeVita, Samuel Hellman, and Steven A. Rosenberg. 4$^{th}$ ed. Philadelphia: J.B. Lippincott Co., 1993.

42. *An Introduction to Genetic Analysis*. David T. Suzuki, et al. 3$^{rd}$ ed. New York: W. H. Freeman and Company, 1986.

43. Ory, Katherine, Yann Legros, Christelle Auguin, and Thierry Soussi. "Analysis of the Most Representative Tumour-Derived p53 Mutants Reveals That Changes in Protein Conformation Are Not Correlated With Loss of Transactivation or Inhibition of Cell Proliferation." *EMBO Journal* 13.15 (1994): 3496–504.

44. Ishioka, C., T. Freburg, Y. Yan, M Vidal, S. H. Friend, and S. Iggo R. Schmidt. *Nature Genetics* 5 (1993): 124–29. Cited in Ory, et al. No article title given.

45. Harris, C. C. "Structure and Function of the p53 Tumor Suppressor Gene: Clues for Rational Cancer Therapeutic Strategies." *Journal of the National Cancer Institute* 88.20 (1996): 1442–55.

46. Debbas, Michael, and Eileen White. "Wild-Type p53 Mediates Apoptosis by E1A, Which Is Inhibited by E1B." *Genes & Development* 7 (1993): 546–54.

47. Hall, P. A., and D. P. Lane. "p53 in Tumour Pathology: Can We Trust Immunohistochemistry?—Revisited!" *Journal of Pathology* 172.1 (1994): 1–4.

48. Liang, Xiao Huan, Martin Molkmann, Ralf Klein, Brian Herman, and Stephen J. Lockett. "Co-Localization of the Tumor-Suppressor Protein p53 and Human Papillomavirus E6 Protein in Human Cervical Carcinoma Cell Lines." *Oncogene* 8 (1993): 2645–52.

49. Pillai, M. Radhakrishna, Susan Halabi, Ann McKalip, P. G. Jayaprakash, T. N. Rajalekshmi, M. Krishnan Nair, and Brian Herman. "The Presence of Human Papillomavirus-16/-18 E6, p53, and Bcl-2 Protein in Cervicovaginal Smears From Patients With Invasive Cervical Cancer." *Cancer Epidemiology, Biomarkers & Prevention* 5 (1996): 329–35.

50. Rogel, A, M Popliker, C. G. Webb, and M. Oren. "p53 Cellular Tumor Antigen: Analysis of MRNA Levels in Normal Adult Tissues, Embryos and Tumors." *Molecular and Cellular Biology* 5 (1985): 2851–55.

51. Sturzbecher, H. W., et al. "Mutant p53 Proteins Bind Hsp72/73 Cellular Heat-Shock-Related Proteins in SV40-Transformed Monkey Cells." *Oncogene* 1 (1987): 201–11. Cited in *American Journal of Pathology*, "p53 Expression in Colorectal Adenomas", Kaklamanis, L, et. Al., Vol. 142 (1), January, 1993.

52. Finlay, C. A., P. W. Hinds, and A. J. Levine. "The p53 Proto-Oncogene Can Act As a Suppressor of Transformation." *Cell* 57 (1989): 1083–93. Cited in *American Journal of Pathology*, Kaklamanis, L., et. al.

53. Clarke, C. F., et al. "Purification of Complexes of Nuclear Oncogene p53 With Rat and Escherichia Coli Heat Shock Proteins: in Vitro Dissociation of Hsc 70 and DnaK From Murine p53 by ATP." *Molecular and Cellular Biology* 8 (1988): 1206–15. Cited in *American Journal of Pathology*, Kaklamanis,L. et. al.

54. Montenarh, Mathias. "Biochemical, Immunological, and Functional Aspects of the Growth-Suppressor/Oncoprotein p53." *Critical Reviews in Oncogenesis* 3 (1992): 233–56. See 8 cited secondary references on page 238.

55. Smith, Martin L., and Albert J. Jr. Fornace. "Mammalian DNA Damage-Inducible Genes Associated With Growth Arrest and Apoptosis." *Mutation Research* 340 (1996): 109–24.

56. Reiss, M., et al. "Status of the p53 Tumor Suppressor Gene in Human Squamous Carcinoma Cell Lines." *Oncology Research* 4. 8–9 (1992): 349–57. Also cited: the prior work of Scheffner, et al., in *Proceedings of the National Academy of Science, USA*. 88:5523–5527.

57. McGregor B., P. Byrne, D. Dirgan, J. Albright, P. Manalo, and M. Hall. "Confirmation of the Association of Human Papillomavirus in Human Colon Cancer." *American Journal of Surgery* 166.6 (1993): 741–2.

58. Zhang, Zuo-Feng, et al., "Tobacco Smoking, Occupation, and p53 Nuclear Overexpression in Early Stage Bladder Cancer." *Cancer Epidemiology, Biomarkers & Prevention* 3 (1994): 19–24.

59. Marx, Jean. "CMV-p53 Interaction May Help Explain Clogged Arteries." *Science* 265 (1994): 320.

60. Levine, A. J., M. E. Perry, A. Chang, A. Silver, D Dittmer, M. Wu, and D. Welsh. "The 1993 Walter Hubert Lecture: The Role of the p53 Tumour—Suppressor Gene in Tumorigenesis." *British Journal of Cancer* 69 (1994): 409–16.

61. Friend, Stephen. "p53: A Glimpse at the Puppet Behind the Shadow Play." *Science* 265 (1994): 334–35.
62. Cattoretti, Giorgio, Stefano Pileri, Carlo Parravicina, Michael H. G. Becker, Simonetta Poggi, Carlo Bifulco, G öran Key, Lucia D'Amato, Sabattini, Elisa Feudale, Fred Reynolds, Johannes Gerdes, and Franco Rilke. "Antigen Unmasking on Formalin-Fixed, Paraffin-Embedded Tissue Sections." *Journal of Pathology* 171 (1993): 83–98.
63. MedLine Database, 1997. *"Medline" Computerized Database.* 1992-*present*. Done September, 1997 by Steven Smith.
64. Greco, Claudia, et al., "Detection of C-Myb Genetic Alterations and Mutant p53 Serum Protein in Patients with Benign and Malignant Colon Lesions." *Anticancer Research* 14 (1994): 1433–40.
65. Andersen, Tone I., Elisabeth Paus, Jahn M. Nesland, Sara J. McKenzie, and Anne-Lise Borresen. "Detection of C-Erb-B2 Related Protein in Sera From Breast Cancer Patients." *Acta Oncologica* 34.4 (1995): 499–504.
66. Dowell, Stephanie P., and Peter A. Hall. "The p53 Tumour Suppressor Gene and Tumour Prognosis: Is There a Relationship?" Editorial. *Journal of Pathology* 177 (1995): 221–24.
67. Sun, Xiao-Feng, John M. Carstensen, Elle Stål, Hong Zhang, Erik Nilsson, Sjödahl, and Nordenskjöld. "Prognostic Significance of p53 Expression in Relation to DNA Ploidy in Colorectal Adenocarcinoma." *Virchows Archives A. Pathological Anatomy and Histopathology* 423 (6) (1993): 443–48.
68. Auvinen, A., J. Isola, T. Visakorpi, T. Koivula, S. Virtanen, and M. Hakama. "Overexpression of p53 and Long-Term Survival in Colon Carcinoma." *British Journal of Cancer* 70.2 (1994): 293–96.
69. Nathanson, S. D., M. D. Linden, P. Tender, R. J. Zarbo, G. Jacobsen, and L. T. Nelson. "Relationship Among p53, Stage and Prognosis of Large Bowel Cancer." *Diseases of the Colon & Rectum* 37.6 (1994): 527–34.
70. Bosari, S., G. Viale, P. Bossi, M. Maggioni, G. Coggi, J. J. Murray, and A. K. Lee. "Cytoplasmic Accumulation of p53 Protein: an Independent Prognostic Indicator in Colorectal Adenocarcinomas." *Journal of the N. C. I.* 86.9 (1994): 681–87.
71. Sun, Xiao-Feng, John M. Carstensen, Hong Zhang, Stål, Wingren Sten, Thomas Hatschek, and Bo Nordenskjöld. "Prognostic Significance of Cytoplasmic p53 Oncoprotein in Colorectal Adenocarcinoma." *The Lancet* 340 (1992): 1399–73.
72. Scott, N., P. Sagar, J. Stewart, G. E. Blair, M. F. Dixon, and P. Quirke. "p53 in Colorectal Cancer: Clinicopathological Correlation and Prognostic Significance." *British Journal of Cancer* 63 (1991): 317–19.
73. Laurent-Puig, Pierre, S. Olschwang, Olivier Delattre, Yourgos Remvikos Remvikos, Bernard Asselain, Thomas Melot, Pierre Validire, Marine Muleris, Jacques Girodet, Remy J. Salmon, and Gilles Thomas. "Survival and Acquired Genetic Alterations in Colorectal Cancer." *Gastroenterology* 102 (1992): 1136–41.
74. Hamilton, Stanley R. "Molecular Genetic Alterations As Potential Prognostic Indicators in Colorectal Carcinoma." *Cancer* 69 (1992): 1589–91.
75. Hamelin, Richard, et al. "Association of p53 Mutations With Short Survival in Colorectal Cancer." *Gastroenterology* 106 (1994): 42–48.
76. Kern, Scott E., Eric R. Fearon, Kasper W. F. Tersmette, John P. Enterline, Mark Leppert, Yusuke Nakamura, Ray White, Bert Vogelstein, and Stanley Hamilton. "Allelic Loss in Colorectal Carcinoma." *JAMA* 261.21 (1989): 3099–103.
77. Barnes, D. M., E. A. Dublin, C. J. Fisher, D. A. Levison, and R. R. Millis. "Immunohistochemical Detection of p53 Protein in Mammary Carcinoma." *Human Pathology* 24 (1993): 469–76. p53 was second only to node status in predicting survival.
78. Thor, Ann D., et al., "Accumulation of p53 Tumor Suppressor Gene Protein: An Independent Marker of Prognosis in Breast Cancers." *Journal of the National Cancer Institute* 84 (1992): 845–55.
79. Thompson, A. M., T. J. Anderson, A Condie, J. Prosser, U. Chetty, D. C. Carter, H. J. Evans, and C. M. Steel. "p53 Allele Losses, Mutations and Expression in Breast Cancer and Their Relationship to Clinico-Pathological Parameters." *International Journal of Cancer* 50 (1992): 528–32.
80. Herod, J. Jonathan, Aristides G. Eliopoulos, Jane Warwick, Gerald Niedobitek, Lawrence S. Young, and David J. Kerr. "The Prognostic Significance of Bcl-2 and p53 Expression in Ovarian Carcinoma." *Cancer Research* 56 (1996): 2178–84.
81. Shin, Dong M. et al., "p53 Expression: Predicting Recurrence and Second Primary Tumors in Head and Neck Squamous Cell Carcinoma." *Journal of the National Cancer Institute* 88.8 (1996): 519–29.
82. Bilim, Vladimir, Yoshihiko Tomita, Takashi Kawasaki, and Akiyoshi Katagiri. "Prognostic Value of Bcl-2 and p53 Expression in Urinary Tract Transitional Cell Cancer." *Journal of the National Cancer Institute* 88. 10 (1996): 686–88.
83. Cunningham, Julie, John A. Lust, Daniel J. Schaid, Gary D. Bren, Herschel A. Carpenter, Elisabeth Rissa, John S. Kovach, and Stephen N. Thibodeau. "Expression of p53 and 17p Allelic Loss in Colorectal Carcinoma." *Cancer Research* 52 (1992): 1974–80.
84. Van den Berg, F. M., A. J. Tigges, M. E. I. Schipper, F. C. A. den Hartog-Jager, W. G. M. Kroes, and J. M. M. Walboomers. "Expression of the Nuclear Oncogene p53 in Colon Tumours." *Journal of Pathology* 157 (1989): 193–99.
85. Pignatelli, Massimo, Gordon W. H. Stamp, Georgia Kafiri, David Lane, and Walter F. Bodmer. "Over-Expression of p53 Nuclear Oncoprotein in Colorectal Adenomas." *International Journal of Cancer* 50 (1992): 683–88.
86. Ohue, Masayuki, et al.,. "A Frequent Alteration of p53 Gene in Carcinoma in Adenoma of Colon." *Cancer Research* 54 (1994): 4798–804.
87. Kaklamanis, Loukas, Kevin C. Gatter, Neil Mortensen, Robert J. Baigrie, Andrew Heryet, David P. Lane, and Adrian L. Harris. "p53 Expression in Colorectal Adenomas." *American Journal of Pathology* 142.1 (1993): 87–93.
88. Fearon, Eric R., and Peter A. Jones. "Progressing Toward a Molecular Description of Colorectal Cancer Development." *FASEB Journal* 6 (1992): 2783–90.
89. Kinzler, Kenneth W., and Bert Vogelstein. "Life (and Death) in a Malignant Tumor." *Nature* 379 (1996): 19–20.
90. Lowe, Scott W., H. Earl Ruley, Tyler Jacks, and David E. Housman. "p53-Dependent Apoptosis Modulates the Cytotoxicity of Anticancer Agents." *Cell* 74 (1993): 957–67.
91. Delia, Domenico, Shuki Mizutani, Giuseppe Lamorte, Kumiko Goi, Satoshi Iwata, and Marco Pierotti. "p53 Activity and Chemotherapy." *Nature Medicine* 2 (1996): 724–25.

92. Chin, Khew-Voon, Kazumitsu Ueda, Ira Pastan, and Michael M. Gottesman. "Modulation of Activity of the Promoter of the Human MDR1 Gene by Ras and p53." *Science* 255 (1992): 459–62.
93. Graeber, Thomas G., Cynthia Osmanian, Tyler Jacks, David E. Housman, Cameron J. Koch, Scott W. Lowe, and Amato J. Giaccia. "Hypoxia-Mediated Selection of Cells With Diminished Apoptotic Potential in Solid Tumours." *Nature* 379 (1996): 88–91.
94. Lotem, Joseph, and Leo Sachs. "Susceptibility to Induction of Apoptosis by Heat-Shock and Cancer Chemotherapy Compounds in Differentiation-Competent and -Defective Myeloid Leukemic Cells." *Cell Growth & Differentiation* 4 (1993): 41–47.
95. Kane, Susan E., Ira Pastan, and Michael M. Gottesman. "Genetic Basis of Multidrug Resistance of Tumor Cells." *Journal of Bioenergetics and Biomembranes* 22.4 (1990): 593–618.
96. Ozbun, Michelle A., and Janet S. Butel. "p53 Tumor Suppressor Gene: Structure and Function." *Encyclopedia of Cancer*. Editor-in-Chief Joseph R. Bertino. Vol. II. New York: Academic Press, 1997. 1240–57.
97. Pettigrew, Norman M. "Techniques in Immunocytochemistry. Application to Diagnostic Pathology." *Archives of Pathology Laboratory Medicine*. 113 (1989): 641–644.
98. Finlay, C. A.,; Hinds, P. W.; Tan, T. h.; Eliyahu, D.; Oren, M; Levine, A. J. "Activating Mutations for Transformation by p53 Produce A Gene Product That Forms an HSC70-p53 Complex With an Altered Half-Life." *Molecular and Cell Biology*. 8 (1988): 532–39. See also: p53 Mutant Selective Quantitative ELISA Assay. Oncogene Science, Cambridge, Mass.: 1991. QIA03.
99. Galen, Robert S., and S. Raymond Gambino. *Beyond Normality: The Predictive Value and Efficiency of Medical Diagnoses*. New York: Wiley & Sons, 1975.
100. Baker, Suzanne J., Sanford Markovitz, Eric R. Fearon, James K. V. Wilson, and Bert Vogelstein. "Suppression of Human Colorectal Carcinoma Cell Growth by Wild-Type p53." *Science* 249 (1990): 912–15.
101. Park, Dorothy J., et al., "Transactivational and DNA Binding Abilities of Endogenous p53 in p53 Mutant Cell Lines." *Oncogene* 9.7 (1994): 1899–906.
102. Oncogene Science, Inc. "p53 (Ab-3)". 1994. OP29/OP29-2.
103. CALBIOCHEM/Oncogene Research Products. *Apoptosis*. Calbiochem-Novabiochem Corp., 1996. See pages 80–81.
104. Vojtêsek, B., J. Bartek, C. A. Midgley, and D. P. Lane. "An Immunochemical Analysis of the Human Nuclear Phosphoprotein p53." *J. Immunological Methods* 151 (1992): 237–44.
105. Rodrigues, Nanda R., Andrew Rowan, Mark E. F. Smith, Ian B. Kerr, Walter Bodmer, Julian Gannon, and David P. Lane. "p53 Mutations in Colorectal Cancer." *Proceedings of the National Academy of Sciences, U.S.A.* 87 (1990): 7555–59.
106. Soussi, T.; Legros, Y.; Lubin, R.; Ory, K.; and Schlichtholz, B. "Multifactorial Analysis of p53 Alteration in Human Cancer: A Review." *Int. J. Cancer*. 57 (1994): 1–9.
107. Fisher, C. J., C. E. Gillett, B. Vojtesek, D. M. Barnes, and R. R. Millis. "Problems With p53 Immunohistochemical Staining: the Effect of Fixation and Variation in the Methods of Evaluation." *British Journal of Cancer* 69.1 (1994): 26–31.
108. Grizzle, William E., Russell B. Myers, Muoi M. Arnold, and Sudhir Srivastava. "Evaluation of Biomarkers in Breast and Prostate Cancer." *Journal of Cellular Biochemistry* [Supplement] 19 (1994): 259–66.
109. Coventry, Brendon J., Sim H. Neoh, Basil X. Mantzioris, John M. Skinner, Heddy Zola, and John Bradley. "A Comparison of the Sensitivity of Immunoperoxidase Staining Methods With High-Sensitivity Fluorescence Flow Cytometry-Antibody Quantitation on the Cell Surface." *J. Histochem. Cytochem.* 42.8 (1994): 1143–47.
110. Bumsted, Howard E. "Spectrophotometry." *The Industrial Environment—Its Evaluation & Control*. Compiler, Public Health Service, Center for DiseaseControl, NIOSH, U.S. Department of Health and Human Services. 1973. 223–46.
111. Rostagno, Philippe, et al., "Immunohistochemical Determination of Nuclear Antigens by Colour Image Analysis: Application for Labelling Index, Estrogen and Progesterone Receptor Status in Breast Cancer." *Analytical Cellular Pathology* 7 (1994): 275–87.
112. Kent, thomas H., and Frank A. Mitros. "Polyps of the Colon and Small Intestine, Polyposis Syndromes, and the Polyp-Carcinoma Sequence." *Pathology of the Colon, Small Intestine and Anus*. Editor: H. Thomas, M. D. Norris. $2^{nd}$ ed. New York: Churchill Livingston, 1991. 189–224.
113. Meyskens, Frank L Jr., Stephen P. Thomson, and Thomas E. Moon. "Quantitation of the Number of Cells Within Tumor Colonies in Semi-solid Medium and Their Growth As Oblate Spheroids." *Cancer Research* 44 (1984): 271–77.114.
114. Marx, Jean. "CMV-p53 Interaction May Help Explain Clogged Arteries." *Science*. (1994): 320.
115. Morton, Donald L. and Barth, Andreas. "Vaccine Therapy for Malignant Melanoma". *CA—A Cancer Journal for Clinicians*. 46. 4 (July/August, 1996): 225–244.
116. Berd, D.; Kairys, J.; Dunton, C.; Mastrongelo, M J.; Sato, T.; Maguire, H C, Jr. "Autologous, hapten-modified vaccine as a treatment for human cancers". [Review] *Seminars in Oncology*. 25. 6. (December, 1998): 646–653.
117. Cao, Y. "Endogenous angiogenesis inhibitors: angiostatin, endostatin, and other proteolytic fragments". [Review] *Progress in Molecular & Subcellular Biology*. 20 (1998): 161–176.
118. Anonymous. "NCI statement on animal studies of endostatin and angiostatin." [In Japanese]. *Japanese Journal of Clinical Oncology*. 28, 7 (1998): 460.
119. Andre, T. et al., "[Tumoral angiogenesis: physiolpahtology, prognostic value and therapeutic perspectives" [In French]. *Revue Medecine Interne*. 19, 12 (1998): 904–913.
120. Brower, Vicki. "LXR needs an elixir to survive". *Nature Biotechnology*. 17(6) (1999): 524–525.
121. Bayley, Hagan. "Building Doors into Cells." *Scientific American*. 277.3 (1997): 62–67.
122. Bischoff, James R. et al., "An Adenovirus Mutant That Replicates Selectively in p53-Deficient Human Tumor Cells." *Science*. 274 (1996): 373–376.
123. Phelan, Anne; Gill, Elliot; O'Hare, Peter. "Intercellular Delivery of Functional p53 by the Herpes Virus Protein VP22." *Nature Biotechnology*. 16, 5 (1998): 440–443.
124. Battifora, Hector A. "Internal Control for Immunocytochemistry Assay" U.S. Pat. No. 5,610,022 (Mar. 11, 1997) (and all references cited therein).
125. Harlow, Ed and Lane David. *Antibodies: A Laboratory Manual*. Cold Spring Harbor, N.Y.: Cold Spring Harbor Laboratories; 1988.

126. "Immunofluorescent Staining and Flow Cytometry Procedures"; *Laboratory Procedures: Oncogene Science Inc.*; September 1990; pp. 1–2.

127. Bourne, Janice A. *Handbook of Immunoperoxidase Staining Methods* [Lab Procedures Manual]. DAKO Corporation, Immunochemistry Laboratory: DAKO Corporation; 1983; pp. 1–36.

128. Ranefall, P; Wester, K; Anderson, A C; Busch, C, and Bengtsson, E. "Automatic quantification of immunohistochemically stained cell nuclei based upon standard reference cells." *Anal. Cellular Pathology* 1998; 17(2):111–123.

129. Andersson, Wester K.; Ranefall, P.; Bengtsson, E., and Malmstrom, P. U. "Cultured human fibroblasts in agarose gel as a multi-functional control for immunohistochemistry. Standardization of Ki67 (MIB1) assessment in routinely processed urinary bladder carcinoma tissue." *Journal of Pathology*. 2000; 190(4):503–511.

130. Woods, Anthony, and Ellis, Roy, *Laboratory Histopathology: A Complete Reference*, 1994 Edinburgh: Churchill Livingstone.

I claim:

1. A method of preparing calibration slides for a cell imaging densitometer, comprising the steps of:

(a) immobilizing cultured cells in a hydrophilic matrix, wherein said hydrophilic matrix is an aqueous gel of a polymer selected from the group consisting of proteins (polypeptides), oligosaccharides, and poly (acrylamide);

(b) placing the matrix in molten paraffin;

(c) cooling the molten paraffin until it solidifies;

(d) exposing the solidified paraffin containing the immobilized cells to a degree of intervening fixation less than produced by fixation with 10% normal buffered for four hours; and (e) sectioning the solidified paraffin containing the immobilized cells into at least one thin slice suitable for optical microscopy.

2. The method of claim 1, wherein the cultured cells are contacted with a tissue fixative prior to immobilization in the hydrophilic matrix.

3. The method of claim 1, wherein the intervening fixation consists of a degree of fixation less than produced by exposure to 10% normal buffered formalin for about two hours or less.

4. The method of claim 3, wherein the intervening fixation consists of a degree of fixation less than produced by exposure to 10% normal buffered formalin for about one hour or less.

5. The method of claim 4, wherein the intervening fixation consists of a degree of fixation less than produced by exposure to 10% normal buffered formalin for about ten minutes or less.

6. The method of claim 1, further comprising the step of contacting the slice with a first antibody.

7. The method of claim 2, further comprising the step of contacting the slice with a first antibody.

8. The method of claim 6, wherein the first antibody is conjugated to a chromogenic or fluorogenic reagent.

9. The method of claim 7, wherein the first antibody is conjugated to a chromogenic or fluorogenic reagent.

10. The method of claim 6, further comprising the step of contacting the slice with a second antibody having binding affinity for the first antibody.

11. The method of claim 7, further comprising the step of contacting the slice with a second antibody having binding affinity for the first antibody.

12. The method of claim 10, wherein the second antibody is conjugated to a chromogenic or fluorogenic reagent.

13. The method of claim 11, wherein the second antibody is conjugated to a chromogenic or fluorogenic reagent.

14. The method of claim 6, wherein the first antibody is conjugated to biotin.

15. The method of claim 7, wherein the first antibody is conjugated to biotin.

16. The method of claim 14, further comprising the step of contacting the slice with a biotinylated chromogenic or fluorogenic reagent in the presence of avidin or streptavidin.

17. The method of claim 15, further comprising the step of contacting the slice with a biotinylated chromogenic or fluorogenic reagent in the presence of avid in or streptavidin.

18. A method of preparing calibration slides for a cell imaging densitometer, comprising the steps of:

(a) immobilizing cultured cells in a hydrophilic matrix, wherein said hydrophilic matrix is an aqueous gel of a polymer selected from the group consisting of proteins (polypeptides), oligosaccharides, and poly (acrylamide);

(b) placing the matrix in molten paraffin;

(c) cooling the molten paraffin until it solidifies; and (d) sectioning the solidified paraffin containing the immobilized cells into at least one thin slice suitable for optical microscopy.

19. The method of claim 1, wherein the hydrophilic matrix is an aqueous gel of a polymer selected from the group consisting of gelatin, agarose, and pectin.

20. The method of claim 19, wherein the hydrophilic matrix is an aqueous gel of agarose.

21. The method of claim 20, wherein the agarose is a low-temperature agarose.

* * * * *